US008765141B2

(12) United States Patent
Rieder et al.

(10) Patent No.: US 8,765,141 B2
(45) Date of Patent: Jul. 1, 2014

(54) DEVELOPMENT OF A MARKER FOOT AND MOUTH DISEASE VIRUS VACCINE CANDIDATE THAT IS ATTENUATED IN THE NATURAL HOST

(75) Inventors: Aida E. Rieder, Westbrook, CT (US); Luis L. Rodriguez, Old Saybrook, CT (US); Jason R. Hollister, Stevensville, MT (US); Sabena Uddowla, Ivoryton, CT (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 146 days.

(21) Appl. No.: 13/157,097

(22) Filed: Jun. 9, 2011

(65) Prior Publication Data

US 2012/0315295 A1    Dec. 13, 2012

Related U.S. Application Data

(60) Provisional application No. 61/360,719, filed on Jul. 1, 2010.

(51) Int. Cl.
*A61K 39/135* (2006.01)
*C12N 7/00* (2006.01)
*C12N 7/02* (2006.01)
*C12N 7/06* (2006.01)
*C12N 15/42* (2006.01)

(52) U.S. Cl.
USPC ............... 424/216.1; 435/235.1; 435/238; 435/239; 424/205.1; 536/23.72

(58) Field of Classification Search
None
See application file for complete search history.

(56) References Cited

PUBLICATIONS

Almeida et al (Virus Research 55:49-60, 1998).*
Fowler et al (Vaccine 26:1982-1989, 2008).*
Li et al (Canadian Journal of Microbiology 57:169-176, 2011).*
Holinka et al (Virology 384:106-113, 2009).*
Yang et al (Journal of Immunological Methods 321:174-181, 2007).*
Berger, H.G et al., Identification of Foot-and-Mouth Disease Virus Replication in Vaccinated Cattle by Antibodies to No-Structural Virus Proteins, Federal Research Centre for Virus Diseases of Animals, Sep. 12, 1989.
Brown, C.C. et al., Pathogenesis of Wild-Type and Leaderless Foot-and-Mouth Disease Virus in Cattle, Journal of Virology, Aug. 1996, p. 5638-5641, vol. 70, No. 8.
Hollister, J. et al., Molecular and Phylogenetic Analyses of Bovine Rhinovirus Type 2 Shows it is Closely Related to Foot-and-Mouth Disease Virus, Science Direct, Virology 373, 2008, pp. 411-425.

Mason, P. et al., RGD Sequence of Foot-and-Mouth Disease Virus is Essential for Infecting Cells via the Natural Receptor but can be Bypassed by an Antibody-Dependent Enhancement Pathway, Proc. Natl. Acad. Sci. USA, vol. 91, pp. 1932-1936, Mar. 1994.
Mason, P.W. et al., Evaluation of a Live-Attenuated Foot-and-Mouth Disease Virus as a Vaccine Candidate, Virology 227, pp. 96-102, 1997.
McKenna, T. et al., Receptor Binding Site-Deleted Foot-and-Mouth Disease (FMD) Virus Protects Cattle from FMD, Journal of Virology, Sep. 1995, pp. 5787-5790, vol. 69, No. 9.
Newman, J.F.E. et al., Foot-and-Mouth Disease Virus Particles Contain Replicase Protein 3D,Proc. Natl. Acad. Sci. USA, vol. 91, pp. 733-737, Jan. 1994.
Newman, J.F.E. et al., Foot-and-Mouth Disease Virus and Poliovirus Particles Contain Proteins of the Replication Complex, Journal of Virology, Oct. 1997, pp. 7657-7662, vol. 71, No. 10.
Piccone, M. et al., The Foot-and-Mouth Disease Virus Leader Proteinase Gene is Not Required for Viral Replication, Journal of Virology, Sep. 1995, p. 5376-5382, vol. 69, No. 9.
Rieder, E. et al., Propagation of an Attenuated Virus by Design: Engineering a Novel Receptor for a Noninfectious Foot-and-Mouth Disease Virus, Proc. Natl. Acad. Sci. USA, vol. 93, pp. 10428-10433, Sep. 1996.
Silberstein, E. et al., Foot-and-Mouth Disease Virus-Infected but not Vaccinated Cattle Develop Antibodies Against Recombinant 3AB1 Nonstructural Protein, Arch Virol, 1997, vol. 142, pp. 795-805.
Yang, M. et al., Identification of a Major Antibody Binding Epitope in the Non-Structural Protein 3D of Foot-and-Mouth Disease Virus in Cattle and the Development of a Monoclonal Antibody With Diagnostic Applications, Journal of Immunological Methods, vol. 321, 2007, pp. 174-181.
Yang, M. et al., Production and Characterization of Two Serotype Independent Monoclonal Antibodies Against Foot-and-Mouth Disease Virus, ScienceDirect, Veterinary Immunology and Immunopathy vol. 115, 2007, pp. 126-134.

* cited by examiner

*Primary Examiner* — Mary E Mosher
(74) *Attorney, Agent, or Firm* — John D. Fado; Evelyn M. Rabin

(57) ABSTRACT

We have generated novel molecularly marked FMDV $A_{24}LL3D_{YR}$ and $A_{24}LL3B_{PVKV}3D_{YR}$ vaccine candidates. The mutant viruses contain a deletion of the leader coding region (LL) rendering the virus attenuated in vivo and negative antigenic markers introduced in one or both of the viral non-structural $3D^{pol}$ and 3B proteins. The vaccine platform includes unique restriction endonuclease sites for easy swapping of capsid proteins for different FMDV subtypes and serotypes. The mutant viruses produced no signs of FMD and no shedding of virulent virus in cattle. No clinical signs of disease or fever were observed and no transmission to in-contact animals was detected in pigs inoculated with live $A_{24}LL3D_{YR}$. Cattle immunized with chemically inactivated vaccine candidates showed an efficacy comparable to a polyvalent commercial FMDV vaccine. These vaccine candidates used in conjunction with a cELISA provide a suitable target for DIVA companion tests.

27 Claims, 12 Drawing Sheets
(2 of 12 Drawing Sheet(s) Filed in Color)

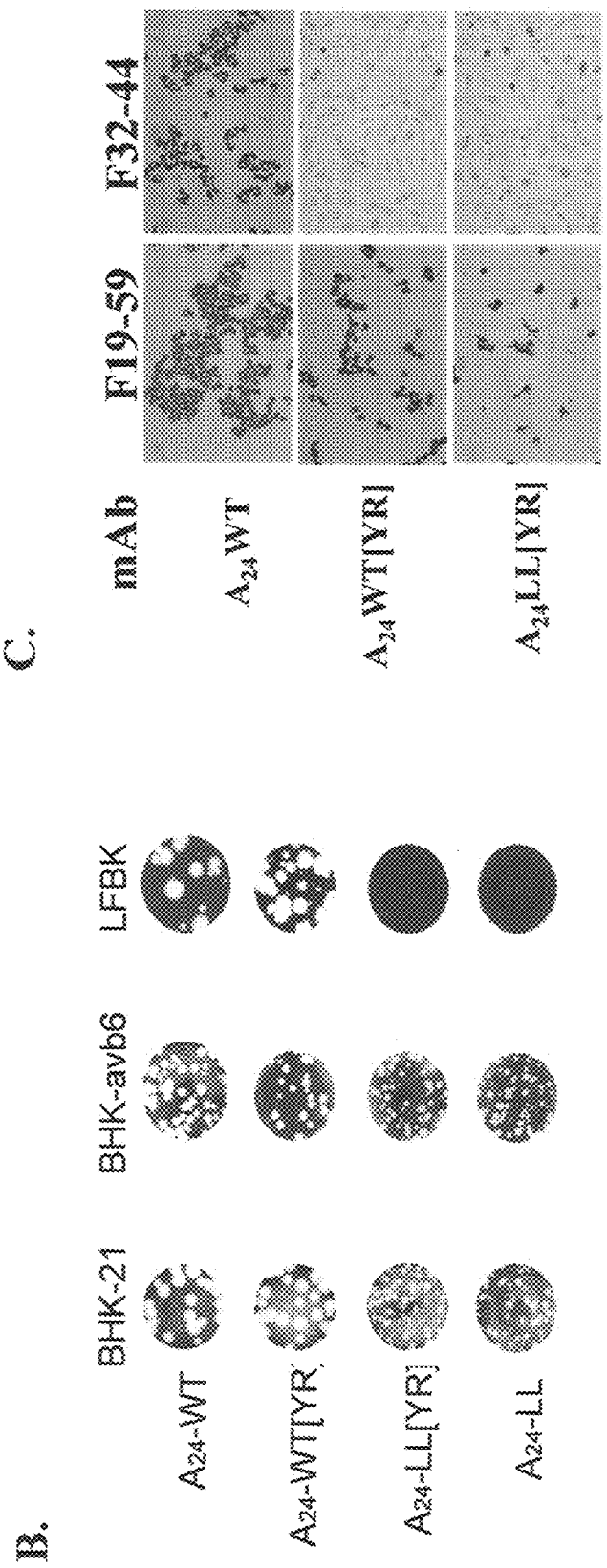
Fig. 3B-C

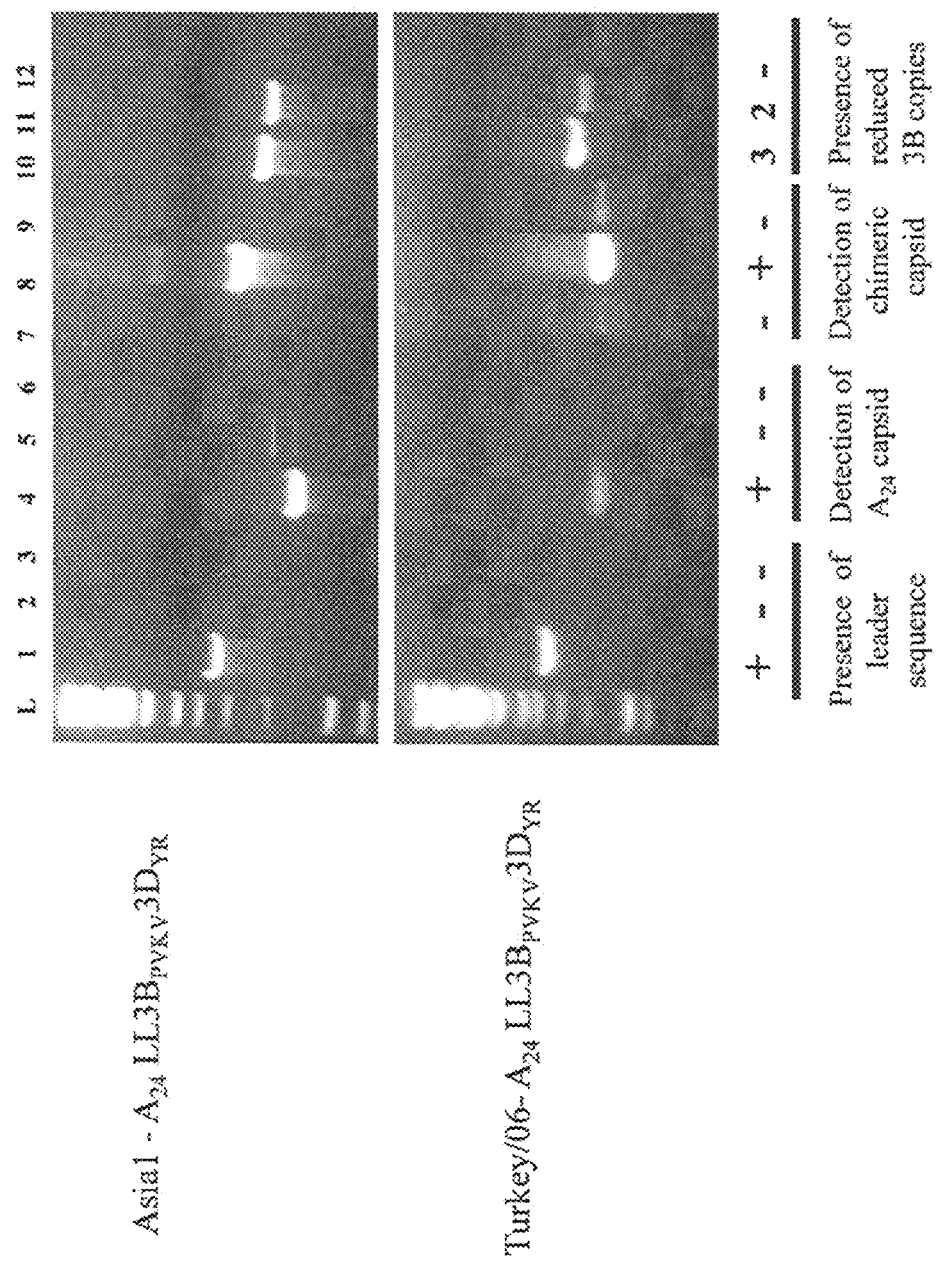

Fig. 9

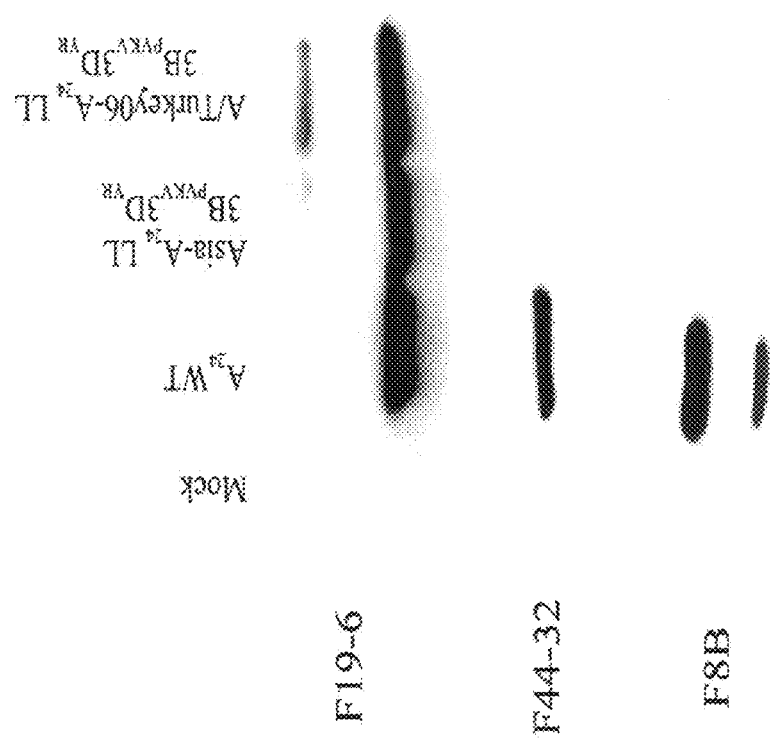

SEQUENCE LISTING

<160> NUMBER OF SEQ ID NOS: 39

<210> SEQ ID NO 1
<211> LENGTH: 10867
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 1

```
ggggccggcc aatccagtcc ggcgaccggc tcgcagaacc aatctggcaa cactggcagc      60
ataattaaca actactacat gcagcaatac cagaactcca tggacacaca gttgggagac     120
aatgccatca gtggaggctc caacgagggc tccacggaca caacttcaac acacacaacc     180
aacactcaaa acaatgactg gttctcgaag ctcgccagtt cagcttttac cggtctgttc     240
ggtgcactgc tcgccgacaa gaagacagag gaaacgacac ttcttgagga ccgcatcctc     300
accacccgca acgggcacac cacctcgacg acccaatcga gtgtgggtgt cacacacggg     360
tactccacag aggaggacca cgttgctggg cccaacacat cgggcctgga gacgcgagtg     420
```

```
gtgcaggcag agagattcta caaaaagtac ttgtttgact ggacaacgga caaggcattt    480
ggacacctgg aaaagctgga gctcccgtcc gaccaccacg gtgtctttgg acacttggtg    540
gactcgtacg cctatatgag aaatggctgg gatgttgagg tgtccgctgt tggcaaccag    600
ttcaacggcg ggtgcctcct ggtggccatg gtacctgaat ggaaggaatt tgacacacgg    660
gagaaatacc aactcaccct tttcccgcac cagtttatta gccccagaac taacatgact    720
gcccacatca cggtccccta ccttggtgtg aacaggtatg atcagtacaa gaagcataag    780
ccctggacat tggttgtcat ggtcgtgtcg ccacttacgg tcaacaacac tagtgcggca    840
caaatcaagg tctacgccaa catagctccg acctatgttc acgtggccgg tgaactcccc    900
tcgaaagagg ggattttccc ggttgcatgt gcggacggtt acggaggatt ggtgacgaca    960
gacccgaaga cagctgaccc tgcttatggc aaggtgtaca cccgcctag gactaactac   1020 cctgggcgct tcaccaacct gttggacgtg gccgaagcgt gtcccacttt cctctgcttt   1080
gacgacggga aaccgtacgt caccacgcgc acggatgaca cccgactttt ggccaagttt   1140
gaccttttcc ttgccgcaaa acatatgtcc aacacatacc tgtcagggat tgctcagtac   1200
tacacacagt actctggcac catcaatttg catttcatgt tcacaggttc cactgattca   1260
aaggcccgat acatggtggc ctacatccca cctggggtgg agacaccacc ggacacacct   1320
gaaagggctg cccactgcat tcacgctgaa tgggacactg gactaaactc caaattcact   1380
ttctcaatcc cgtacgtatc cgccgcggat tacgcgtaca cagcgtctga cacggcagaa   1440
acaatcaacg tacagggatg ggtctgcatc taccaaatta cacacgggaa ggctgaaaat   1500
gacaccttgg tcgtgtcggt tagcgccggc aaagactttg agttgcgcct cccgattgac   1560
ccccgccagc agaccaccgc taccggggaa tcagcagacc cggtcaccac caccgtggag   1620
aactacggcg gtgagacaca aatccagaga cgtcaccaca cggacattgg tttcatcatg   1680
gacagatttg tgaagatcca aagcttgagc ccaacacatg tcattgacct catgcagact   1740
caccaacacg gtctggtggg tgccttgctg cgtgcagcca cgtactactt ttctgacctg   1800
gaaattgttg tacggcacga aggcaatctg acctgggtgc caacggcgc ccctgaatca   1860 gccctgttga acaccagcaa ccccactgcc tacaacaagg caccattcac gagactcgct   1920
ctcccctaca ctgcgccgca ccgtgtgctg caacagtgt acaacgggac gagtaagtat   1980
gctgtgggtg gttcaggcag aagaggcgac atggggtctc tcgcggcgcg agtcgtgaaa   2040
cagcttcctg cttcatttaa ctacggtgca atcaaggccg acgccatcca cgaacttctc   2100
gtgcgcatga acgggccga gctctactgc cccagaccgc tgttggcaat agaggtgtct   2160
tcgcaagaca ggcacaagca aaagatcatt gcaccagcaa agcagcttct gaattttgac   2220
ctgcttaagc tagccggaga cgttgagtcc aaccctgggc ccttcttctt ctccgacgtt   2280 aggtcaaaact tttccaagct ggtagacaca atcaaccaga tgcaggaaga catgtccaca   2340
aagcacggac ctgactttaa ccggttggtg tccgcttttg aggagttggc cactggagtg   2400
aaagccatca ggaccggtct tgacgaggcc aagccctggt acaagcttat caagctcctg   2460
agccgcctgt cgtgcatggc cgctgtggca gcacggtcaa aggacccagt ccttgtggcc   2520
atcatgctgg ctgacaccgg tctcgagatt ctggacagcc ccttcgtcgt gaagaagatc   2580
tccgactcgc tctccagtct cttccacgtg ccggcccccg tcttcagttt cggagccccg   2640
attctgttag ccgggttggt caaggtcgcc tcgagtttct tccggtccac gcccgaagac   2700
cttgagagag cagagaaaca gctcaaagca cgtgacatca acgacatttt cgccattctc   2760
```

```
aagaacggcg agtggctggt caaattgatc cttgccatcc gcgactggat caaggcatgg    2820
atagcctcag aagaaaagtt tgtcaccacg acagacttgg tacctagcat ccttgaaaaa    2880
cagcaggacc tcaacgaccc aagcaagtac aaggaagcca aggagtggct cgacaacgcg    2940
cgccaagcgt gttttgaagag cgggaacgtc cacattgcca acctgtgcaa agtggtcgcc    3000
ccggcaccca gcaggtcgag acccgagccc gtggtcgttt gcctccgtgg caagtccggt    3060
cagggcaaga gtttccttgc aaacgtgctc gcacaagcaa tctctaccca tttcactggc    3120
aggaccgatt cagtttggta ctgcccgcct gaccctgacc acttcgacgg ttacaaccaa    3180
cagactgtcg ttgtgatgga cgatttgggc cagaaccccg acggcaaaga cttcaagtac    3240
ttcgcccaaa tggttttcaac aacggggttc atcccgccca tggcatcgct tgaggataaa    3300
ggcaaaccct tcaacagtaa ggtcatcata gcaaccacca acctgtactc gggcttcacc    3360
ccgaggacta tggtgtgccc tgatgccctg aaccggaggt ttcactttga catcgacgtg    3420
agcgccaagg acgggtacaa aattaacaac aaattggaca tcatcaaagc acttgaagat    3480
actcacacca acccagtggc aatgtttcag tacgactgtg cccttctcaa cggcatggct    3540
gttgaaatga agagaatgca acaagatatg ttcaagcctc aaccacccct tcagaacgtg    3600
taccaactgg ttcaagaggt gattgagcgg gtggagctcc acgagaaggt gtcgagccac    3660
ccgattttca aacagatctc aattccttcc caaaaatccg tgttgtactt cctcattgag    3720
aaaggacagc acgaggcagc aattgaattc tttgagggca tggtgcacga ctccatcaag    3780
gaggagctcc ggccgctcat ccaacaaacc tcatttgtga aacgcgcttt taagcgcctg    3840
aaggaaaact ttgagattgt tgccctatgt ctgaccctcc tggccaacat agtgatcatg    3900
atccgcgaaa ctcgcaagag acagaagatg gtggacgatg cagtgagtga gtacattgag    3960
agagcaaaca tcaccaccga cgacaagact cttgatgagg cggaaaagaa ccctctggaa    4020
accagcggtg ccagcaccgt cggcttcaga gagagacctc tcccaggcca aaaggcgcgt    4080
aatgacgaga actccgagcc cgcccagcct gctgaagagc aaccacaagc tgaaggaccc    4140
tacgctggcc cgatggagag accagttaaa gttaaagtga agcaaaaagc cccggtcgtt    4200
aaggaaggac cttacgaggg accggtgaag aagcctgttg ctttgaaagt gaaagctaag    4260
aacttgatcg tcactgagag tggtgcccca ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag acaggacat gctctcagac gctgcgctca ggggccggcc aatccagtcc    4560
ggcgaccggc tcgcagaacc aatctggcaa cactggcagc ataattaaca actactacat    4620
gcagcaatac cagaactcca tggacacaca gttgggagac aatgccatca gtggaggctc    4680
caacgagggc tccacggaca caacttcaac acacacaacc aacactcaaa caatgactg    4740 gttctcgaag ctcgccagtt cagctttac cggtctgttc ggtgcactgc tcgccgacaa    4800
gaagacagag gaaacgacac ttcttgagga ccgcatcctc accacccgca acgggcacac    4860
cacctcgacg acccaatcga gtgtgggtgt cacacacggg tactccacag aggaggacca    4920
cgttgctggg cccaacacat cgggcctgga gacgcgagtg gtgcaggcag agagattcta    4980
caaaaagtac ttgtttgact ggacaacgga caaggcattt ggacacctgg aaaagctgga    5040
gctcccgtcc gaccaccacg gtgtctttgg acacttggtg gactcgtacg cctatatgag    5100
aaatggctgg gatgttgagg tgtccgctgt tggcaaccag ttcaacggcg ggtgcctcct    5160
```

```
ggtggccatg gtacctgaat ggaaggaatt tgacacacgg gagaaatacc aactcaccct    5220
tttcccgcac cagtttatta gccccagaac taacatgact gcccacatca cggtccccta    5280
ccttggtgtg aacaggtatg atcagtacaa gaagcataag ccctggacat tggttgtcat    5340
ggtcgtgtcg ccacttacgg tcaacaacac tagtgcggca caaatcaagg tctacgccaa    5400
catagctccg acctatgttc acgtggccgg tgaactcccc tcgaaagagg gattttccc    5460 ggttgcatgt gcggacggtt acggaggatt ggtgacgaca gacccgaaga cagctgaccc    5520
tgcttatggc aaggtgtaca acccgcctag gactaactac cctgggcgct tcaccaacct    5580
gttggacgtg gccgaagcgt gtcccacttt cctctgcttt gacgacggga aaccgtacgt    5640
caccacgcgg acggatgaca cccgactttt ggccaagttt gacctttccc ttgccgcaaa    5700
acatatgtcc aacacatacc tgtcagggat tgctcagtac tacacacagt actctggcac    5760
catcaatttg catttcatgt tcacaggttc cactgattca aaggcccgat acatggtggc    5820
ctacatccca cctggggtgg agacaccacc ggacacacct gaaagggctg cccactgcat    5880
tcacgctgaa tgggacactg gactaaactc caaattcact ttctcaatcc cgtacgtatc    5940
cgccgcggat tacgcgtaca cagcgtctga cacggcagaa acaatcaacg tacagggatg    6000
ggtctgcatc taccaaatta cacacgggaa ggctgaaaat gacaccttgg tcgtgtcggt    6060
tagcgccggc aaagactttg agttgcgcct cccgattgac cccgccagc agaccaccgc    6120 taccggggaa tcagcagacc cggtcaccac caccgtggag aactacggcg gtgagacaca    6180
aatccagaga cgtcaccaca cggacattgg tttcatcatg gacagatttg tgaagatcca    6240
aagcttgagc ccaacacatg tcattgacct catgcagact caccaacacg gtctggtggg    6300
tgccttgctg cgtgcagcca cgtactactt ttctgacctg gaaattgttg tacggcacga    6360
aggcaatctg acctgggtgc ccaacggcgc ccctgaatca gccctgttga acaccagcaa    6420 cccccactgcc tacaacaagg caccattcac gagactcgct ctcccctaca ctgcgccgca    6480
ccgtgtgctg gcaacagtgt acaacgggac gagtaagtat gctgtgggtg gttcaggcag    6540
aagaggcgac atgggtgtctc tcgcggcgcg agtcgtgaaa cagcttcctg cttcatttaa    6600
ctacggtgca atcaaggccg acgccatcca cgaacttctc gtgcgcatga acgggccga    6660 gctctactgc cccagaccgc tgttggcaat agaggtgtct tcgcaagaca ggcacaagca    6720
aaagatcatt gcaccagcaa agcagcttct gaattttgac ctgcttaagc tagccggaga    6780
cgttgagtcc aaccctgggc ccttcttctt ctccgacgtt aggtcaaaact tttccaagct    6840 ggtagacaca atcaaccaga tgcaggaaga catgtccaca aagcacggac ctgactttaa    6900
ccggttggtg tccgcttttg aggagttggc cactggagtg aaagccatca ggaccggtct    6960
tgacgaggcc aagccctggt acaagcttat caagctcctg agccgccgt cgtgcatggc    7020 cgctgtggca gcacggtcaa aggacccagt ccttgtggcc atcatgctgg ctgacaccgg    7080
tctcgagatt ctggacagca ccttcgtcgt gaagaagatc tccgactcgc tctccagtct    7140
cttccacgtg ccggccccccg tcttcagttt cggagccccg attctgttag ccgggttggt    7200
caaggtcgcc tcgagtttct tccggtccac gcccgaagac cttgagagag cagagaaaca    7260
gctcaaagca cgtgacatca cgacattttt cgccattctc aagaacggcg agtggctggt    7320
caaattgatc cttgccatcc gcgactggat caaggcatgg atagcctcag aagaaaagtt    7380
tgtcaccacg acagacttgg tacctagcat ccttgaaaaa cagcaggacc tcaacgaccc    7440
aagcaagtac aaggaagcca aggagtggct cgacaacgcg cgccaagcgt gtttgaagag    7500
```

```
cgggaacgtc cacattgcca acctgtgcaa agtggtcgcc ccggcaccca gcaggtcgag     7560
acccgagccc gtggtcgttt gcctccgtgg caagtccggt cagggcaaga gtttccttgc     7620
aaacgtgctc gcacaagcaa tctctaccca tttcactggc aggaccgatt cagtttggta     7680
ctgcccgcct gaccctgacc acttcgacgg ttacaaccaa cagactgtcg ttgtgatgga     7740
cgatttgggc cagaaccccg acggcaaaga cttcaagtac ttcgcccaaa tggtttcaac     7800
aacggggttc atcccgccca tggcatcgct tgaggataaa ggcaaaccct tcaacagtaa     7860
ggtcatcata gcaaccacca acctgtactc gggcttcacc ccgaggacta tggtgtgccc     7920
tgatgccctg aaccggaggt ttcactttga catcgacgtg agcgccaagg acgggtacaa     7980
aattaacaac aaattggaca tcatcaaagc acttgaagat actcacacca acccagtggc     8040
aatgtttcag tacgactgtg cccttctcaa cggcatggct gttgaaatga agagaatgca     8100
acaagatatg ttcaagcctc aaccaccct tcagaacgtg taccaactgg ttcaagaggt     8160
gattgagcgg gtggagctcc acgagaaggt gtcgagccac ccgattttca aacagatctc     8220
aattccttcc caaaaatccg tgttgtactt cctcattgag aaaggacagc acgaggcagc     8280
aattgaattc tttgagggca tggtgcacga ctccatcaag gaggagctcc ggccgctcat     8340
ccaacaaacc tcatttgtga aacgcgcttt taagcgcctg aaggaaaact ttgagattgt     8400
tgccctatgt ctgaccctcc tggccaacat agtgatcatg atccgcgaaa ctcgcaagag     8460
acagaagatg gtggacgatg cagtgagtga gtacattgag agagcaaaca tcaccaccga     8520
cgacaagact cttgatgagg cggaaaagaa ccctctggaa ccagcggtg ccagcaccgt     8580 cggcttcaga gagagacctc tcccaggcca aaaggcgcgt aatgacgaga actccgagcc     8640
cgcccagcct gctgaagagc aaccacaagc tgaaggaccc tacgctggcc cgatggagag     8700
accagttaaa gttaaagtga agcaaaagc cccggtcgtt aaggaaggac cttacgaggg     8760
accggtgaag aagcctgttg ctttgaaagt gaaagctaag aacttgatcg tcactgagag     8820
tggtgcccca ccgaccgact tgcaaaagtt ggtcatgggc aacaccaagc ccgttgagct     8880
catccttgac gggaagacgg tagccatttg ctgtgctact ggagttttcg gcactgctta     8940
cctcgtgcct cgtcatcttt tcgcagaaaa gtacgacaag atcatgttgg acggcagagc     9000
catgacagat agtgactaca gagtgtttga gtttgagatt aaagtaaaag gacaggacat     9060
gctctcagac gctgcgctca tggtgctcca ccgtgggaat cgcgtgagag acatcacgaa     9120
acactttcgt gacacagcaa gaatgaagaa aggcaccccc gtcgttggtg tgatcaacaa     9180
cgccgatgtc gggagactga ttttctctgg tgaagccctt acctacaagg acattgtagt     9240
gtgcatggat ggagacacca tgcctgggct cttttgcctac aaagccgcaa ccaaggctgg     9300
ttattgcgga ggagccgtcc tcgctaagga cggggctgac acgttcatcg ttggcaccca     9360
ctccgctgga ggcaatggcg ttggatactg ctcttgcgtt tccaggtcca tgcttctcaa     9420
gatgaaggca cacgttgacc ccgaaccaca ccacgagggg ttgattgttg acaccagaga     9480
tgtggaagag cgcgttcacg tgatgcgcaa aaccaagctt gcacccaccg ttgcgtacgg     9540
tgtgttccgt cctgagttcg ggcctgccgc cttgtccaac aaggaccccgc gcctgaacga     9600 cggtgttgtc ctcgacgaag tcatcttctc caaacacaag ggagacacaa agatgtctga     9660
ggaagacaaa gcgctgttcc gccgctgtgc tgctgactac gcgtcacgcc tgcacagcgt     9720
gttgggtacg gcaaatgccc cactgagcat ctacgaggca attaaggcg ttgatggact     9780 cgacgcaatg gaaccagaca ccgcacccgg cctcccctgg gcactccagg ggaagcgccg     9840
tggcgcgctc atcgacttcg agaacggcac tgttggaccc gaagttgagg ctgccttgaa     9900
```

-continued

```
gctcatggag aaaagagaat acaagtttgc ttgccaaacc ttcctgaagg acgagattcg      9960
cccgatggag aaagtacgtg ccggtaagac tcgcattgtc gacgtcctac ctgttgaaca     10020
catcctctac accaggatga tgattggcag attttgtgca caaatgcact caaacaacgg     10080
accccaaatt ggctcggcgg tcggttgtaa ccctgatgtt gattggcaaa gatttggcac     10140
acacttcgcc caatacagaa acgtgtggga tgtggactat cggccttcg atgctaacca      10200
ctgcagtgac gccatgaaca tcatgtttga ggaagtgttt cgcacagaat cgggttcca      10260
cccaaacgct gagtggatcc tgaagactct cgtgaacacg gaacacgcct atgagaacaa     10320
acgcatcact gttgaaggcg ggatgccatc tggttgttcc gcaacaagca tcatcaacac     10380
aattttgaac aacatctacg tgctctacgc tttgcgtaga cactatgagg gagttgagct     10440
ggacacttac accatgatct cttacggaga cgatatcgtg gtggcaagtg attacgattt     10500
ggactttgag gctctcaagc cccacttcaa atcccttggt caaaccatca ctccagctga     10560
caaaagcgac aaaggttttg ttcttggtca ctccattact gatgtcactt tcctcaaaag     10620
acacttccac atggattatg aactgggtt ttacaaacct gtgatggcct caaagaccct      10680
tgaggctatc ctctcctttg cacgccgtgg gaccatacag gagaagttga tctccgtggc     10740
aggactcgct gttcactctg gaccagacga gtaccggcgt ctcttcgagc cctttcaagg     10800
cctcttcgag attccaagct acagatcact ttacctgcgt tgggtgaacg ccgtgtgcgg     10860
cgacgca                                                              10867
```

<210> SEQ ID NO 2
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus
      (FMDV) and Bovine Rhinovirus Type 2 (BRV2)

<400> SEQUENCE: 2

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr His Gly Tyr Ser Thr Glu Glu Asp His Val
        115                 120                 125

Ala Gly Pro Asn Thr Ser Gly Leu Glu Thr Arg Val Val Gln Ala Glu
    130                 135                 140

Arg Phe Tyr Lys Lys Tyr Leu Phe Asp Trp Thr Thr Asp Lys Ala Phe
145                 150                 155                 160

Gly His Leu Glu Lys Leu Glu Leu Pro Ser Asp His His Gly Val Phe
                165                 170                 175
```

Gly His Leu Val Asp Ser Tyr Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Glu Phe Asp Thr Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270

Thr Val Asn Asn Thr Ser Ala Ala Gln Ile Lys Val Tyr Ala Asn Ile
        275                 280                 285

Ala Pro Thr Tyr Val His Val Ala Gly Glu Leu Pro Ser Lys Glu Gly
    290                 295                 300

Ile Phe Pro Val Ala Cys Ala Asp Gly Tyr Gly Gly Leu Val Thr Thr
305                 310                 315                 320

Asp Pro Lys Thr Ala Asp Pro Ala Tyr Gly Lys Val Tyr Asn Pro Pro
                325                 330                 335

Arg Thr Asn Tyr Pro Gly Arg Phe Thr Asn Leu Leu Asp Val Ala Glu
            340                 345                 350

Ala Cys Pro Thr Phe Leu Cys Phe Asp Asp Gly Lys Pro Tyr Val Thr
        355                 360                 365

Thr Arg Thr Asp Asp Thr Arg Leu Leu Ala Lys Phe Asp Leu Ser Leu
    370                 375                 380

Ala Ala Lys His Met Ser Asn Thr Tyr Leu Ser Gly Ile Ala Gln Tyr
385                 390                 395                 400

Tyr Thr Gln Tyr Ser Gly Thr Ile Asn Leu His Phe Met Phe Thr Gly
                405                 410                 415

Ser Thr Asp Ser Lys Ala Arg Tyr Met Val Ala Tyr Ile Pro Pro Gly
            420                 425                 430

Val Glu Thr Pro Pro Asp Thr Pro Glu Arg Ala Ala His Cys Ile His
        435                 440                 445

Ala Glu Trp Asp Thr Gly Leu Asn Ser Lys Phe Thr Phe Ser Ile Pro
    450                 455                 460

Tyr Val Ser Ala Ala Asp Tyr Ala Tyr Thr Ala Ser Asp Thr Ala Glu
465                 470                 475                 480

Thr Ile Asn Val Gln Gly Trp Val Cys Ile Tyr Gln Ile Thr His Gly
                485                 490                 495

Lys Ala Glu Asn Asp Thr Leu Val Val Ser Val Ser Ala Gly Lys Asp
            500                 505                 510

Phe Glu Leu Arg Leu Pro Ile Asp Pro Arg Gln Gln Thr Thr Ala Thr
        515                 520                 525

Gly Glu Ser Ala Asp Pro Val Thr Thr Val Glu Asn Tyr Gly Gly
    530                 535                 540

Glu Thr Gln Ile Gln Arg Arg His His Thr Asp Ile Gly Phe Ile Met
545                 550                 555                 560

Asp Arg Phe Val Lys Ile Gln Ser Leu Ser Pro Thr His Val Ile Asp
                565                 570                 575

Leu Met Gln Thr His Gln His Gly Leu Val Gly Ala Leu Leu Arg Ala
            580                 585                 590

Ala Thr Tyr Tyr Phe Ser Asp Leu Glu Ile Val Val Arg His Glu Gly

```
                595                 600                 605
Asn Leu Thr Trp Val Pro Asn Gly Ala Pro Glu Ser Ala Leu Leu Asn
610                 615                 620

Thr Ser Asn Pro Thr Ala Tyr Asn Lys Ala Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Ser Lys Tyr Ala Val Gly Gly Ser Gly Arg Arg Gly Asp Met Gly
                660                 665                 670

Ser Leu Ala Ala Arg Val Val Lys Gln Leu Pro Ala Ser Phe Asn Tyr
                675                 680                 685

Gly Ala Ile Lys Ala Asp Ala Ile His Glu Leu Leu Val Arg Met Lys
690                 695                 700

Arg Ala Glu Leu Tyr Cys Pro Arg Pro Leu Leu Ala Ile Glu Val Ser
705                 710                 715                 720

Ser Gln Asp Arg His Lys Gln Lys Ile Ile Ala Pro Ala Lys Gln Leu
                725                 730                 735

Leu Asn Phe Asp Leu Leu Lys Leu Ala Gly Asp Val Glu Ser Asn Pro
                740                 745                 750

Gly Pro Phe Phe Phe Ser Asp Val Arg Ser Asn Phe Ser Lys Leu Val
                755                 760                 765

Asp Thr Ile Asn Gln Met Gln Glu Asp Met Ser Thr Lys His Gly Pro
770                 775                 780

Asp Phe Asn Arg Leu Val Ser Ala Phe Glu Glu Leu Ala Thr Gly Val
785                 790                 795                 800

Lys Ala Ile Arg Thr Gly Leu Asp Glu Ala Lys Pro Trp Tyr Lys Leu
                805                 810                 815

Ile Lys Leu Leu Ser Arg Leu Ser Cys Met Ala Ala Val Ala Ala Arg
                820                 825                 830

Ser Lys Asp Pro Val Leu Val Ala Ile Met Leu Ala Asp Thr Gly Leu
                835                 840                 845

Glu Ile Leu Asp Ser Thr Phe Val Val Lys Lys Ile Ser Asp Ser Leu
850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
                900                 905                 910

Ile Asn Asp Ile Phe Ala Ile Leu Lys Asn Gly Glu Trp Leu Val Lys
                915                 920                 925

Leu Ile Leu Ala Ile Arg Asp Trp Ile Lys Ala Trp Ile Ala Ser Glu
930                 935                 940

Glu Lys Phe Val Thr Thr Thr Asp Leu Val Pro Ser Ile Leu Glu Lys
945                 950                 955                 960

Gln Gln Asp Leu Asn Asp Pro Ser Lys Tyr Lys Glu Ala Lys Glu Trp
                965                 970                 975

Leu Asp Asn Ala Arg Gln Ala Cys Leu Lys Ser Gly Asn Val His Ile
                980                 985                 990

Ala Asn Leu Cys Lys Val Val Ala  Pro Ala Pro Ser Arg  Ser Arg Pro
                995                1000                1005

Glu Pro Val Val Val Cys Leu  Arg Gly Lys Ser Gly  Gln Gly Lys
           1010                1015                1020
```

```
Ser Phe Leu Ala Asn Val Leu Ala Gln Ala Ile Ser Thr His Phe
    1025                1030                1035

Thr Gly Arg Thr Asp Ser Val Trp Tyr Cys Pro Pro Asp Pro Asp
    1040                1045                1050

His Phe Asp Gly Tyr Asn Gln Gln Thr Val Val Val Met Asp Asp
    1055                1060                1065

Leu Gly Gln Asn Pro Asp Gly Lys Asp Phe Lys Tyr Phe Ala Gln
    1070                1075                1080

Met Val Ser Thr Thr Gly Phe Ile Pro Pro Met Ala Ser Leu Glu
    1085                1090                1095

Asp Lys Gly Lys Pro Phe Asn Ser Lys Val Ile Ile Ala Thr Thr
    1100                1105                1110

Asn Leu Tyr Ser Gly Phe Thr Pro Arg Thr Met Val Cys Pro Asp
    1115                1120                1125

Ala Leu Asn Arg Arg Phe His Phe Asp Ile Asp Val Ser Ala Lys
    1130                1135                1140

Asp Gly Tyr Lys Ile Asn Asn Lys Leu Asp Ile Ile Lys Ala Leu
    1145                1150                1155

Glu Asp Thr His Thr Asn Pro Val Ala Met Phe Gln Tyr Asp Cys
    1160                1165                1170

Ala Leu Leu Asn Gly Met Ala Val Glu Met Lys Arg Met Gln Gln
    1175                1180                1185

Asp Met Phe Lys Pro Gln Pro Pro Leu Gln Asn Val Tyr Gln Leu
    1190                1195                1200

Val Gln Glu Val Ile Glu Arg Val Glu Leu His Glu Lys Val Ser
    1205                1210                1215

Ser His Pro Ile Phe Lys Gln Ile Ser Ile Pro Ser Gln Lys Ser
    1220                1225                1230

Val Leu Tyr Phe Leu Ile Glu Lys Gly Gln His Glu Ala Ala Ile
    1235                1240                1245

Glu Phe Phe Glu Gly Met Val His Asp Ser Ile Lys Glu Glu Leu
    1250                1255                1260

Arg Pro Leu Ile Gln Gln Thr Ser Phe Val Lys Arg Ala Phe Lys
    1265                1270                1275

Arg Leu Lys Glu Asn Phe Glu Ile Val Ala Leu Cys Leu Thr Leu
    1280                1285                1290

Leu Ala Asn Ile Val Ile Met Ile Arg Glu Thr Arg Lys Arg Gln
    1295                1300                1305

Lys Met Val Asp Asp Ala Val Ser Glu Tyr Ile Glu Arg Ala Asn
    1310                1315                1320

Ile Thr Thr Asp Asp Lys Thr Leu Asp Glu Ala Glu Lys Asn Pro
    1325                1330                1335

Leu Glu Thr Ser Gly Ala Ser Thr Val Gly Phe Arg Glu Arg Pro
    1340                1345                1350

Leu Pro Gly Gln Lys Ala Arg Asn Asp Glu Asn Ser Glu Pro Ala
    1355                1360                1365

Gln Pro Ala Glu Glu Gln Pro Gln Ala Glu Gly Pro Tyr Ala Gly
    1370                1375                1380

Pro Met Glu Arg Pro Val Lys Val Lys Val Lys Ala Lys Ala Pro
    1385                1390                1395

Val Val Lys Glu Gly Pro Tyr Glu Gly Pro Val Lys Lys Pro Val
    1400                1405                1410
```

-continued

```
Ala Leu Lys Val Lys Ala Lys Asn Leu Ile Val Thr Glu Ser Gly
    1415                1420                1425

Ala Pro Pro Thr Asp Leu Gln Lys Leu Val Met Gly Asn Thr Lys
    1430                1435                1440

Pro Val Glu Leu Ile Leu Asp Gly Lys Thr Val Ala Ile Cys Cys
    1445                1450                1455

Ala Thr Gly Val Phe Gly Thr Ala Tyr Leu Val Pro Arg His Leu
    1460                1465                1470

Phe Ala Glu Lys Tyr Asp Lys Ile Met Leu Asp Gly Arg Ala Met
    1475                1480                1485

Thr Asp Ser Asp Tyr Arg Val Phe Glu Phe Glu Ile Lys Val Lys
    1490                1495                1500

Gly Gln Asp Met Leu Ser Asp Ala Ala Leu Met Val Leu His Arg
    1505                1510                1515

Gly Asn Arg Val Arg Asp Ile Thr Lys His Phe Arg Asp Thr Ala
    1520                1525                1530

Arg Met Lys Lys Gly Thr Pro Val Val Gly Val Ile Asn Asn Ala
    1535                1540                1545

Asp Val Gly Arg Leu Ile Phe Ser Gly Glu Ala Leu Thr Tyr Lys
    1550                1555                1560

Asp Ile Val Val Cys Met Asp Gly Asp Thr Met Pro Gly Leu Phe
    1565                1570                1575

Ala Tyr Lys Ala Ala Thr Lys Ala Gly Tyr Cys Gly Gly Ala Val
    1580                1585                1590

Leu Ala Lys Asp Gly Ala Asp Thr Phe Ile Val Gly Thr His Ser
    1595                1600                1605

Ala Gly Gly Asn Gly Val Gly Tyr Cys Ser Cys Val Ser Arg Ser
    1610                1615                1620

Met Leu Leu Lys Met Lys Ala His Val Asp Pro Glu Pro His His
    1625                1630                1635

Glu Gly Leu Ile Val Asp Thr Arg Asp Val Glu Glu Arg Val His
    1640                1645                1650

Val Met Arg Lys Thr Lys Leu Ala Pro Thr Val Ala Tyr Gly Val
    1655                1660                1665

Phe Arg Pro Glu Phe Gly Pro Ala Ala Leu Ser Asn Lys Asp Pro
    1670                1675                1680

Arg Leu Asn Asp Gly Val Val Leu Asp Glu Val Ile Phe Ser Lys
    1685                1690                1695

His Lys Gly Asp Thr Lys Met Ser Glu Glu Asp Lys Ala Leu Phe
    1700                1705                1710

Arg Arg Cys Ala Ala Asp Tyr Ala Ser Arg Leu His Ser Val Leu
    1715                1720                1725

Gly Thr Ala Asn Ala Pro Leu Ser Ile Tyr Glu Ala Ile Lys Gly
    1730                1735                1740

Val Asp Gly Leu Asp Ala Met Glu Pro Asp Thr Ala Pro Gly Leu
    1745                1750                1755

Pro Trp Ala Leu Gln Gly Lys Arg Arg Gly Ala Leu Ile Asp Phe
    1760                1765                1770

Glu Asn Gly Thr Val Gly Pro Glu Val Glu Ala Ala Leu Lys Leu
    1775                1780                1785

Met Glu Lys Arg Glu Tyr Lys Phe Ala Cys Gln Thr Phe Leu Lys
    1790                1795                1800

Asp Glu Ile Arg Pro Met Glu Lys Val Arg Ala Gly Lys Thr Arg
```

```
                  1805                    1810                    1815
Ile Val  Asp Val Leu Pro Val Glu His Ile Leu Tyr Thr Arg Met
    1820                    1825                    1830

Met Ile Gly Arg Phe Cys Ala Gln Met His Ser Asn Asn Gly Pro
    1835                    1840                    1845

Gln Ile Gly Ser Ala Val Gly Cys Asn Pro Asp Val Asp Trp Gln
    1850                    1855                    1860

Arg Phe Gly Thr His Phe Ala Gln Tyr Arg Asn Val Trp Asp Val
    1865                    1870                    1875

Asp Tyr Ser Ala Phe Asp Ala Asn His Cys Ser Asp Ala Met Asn
    1880                    1885                    1890

Ile Met Phe Glu Glu Val Phe Arg Thr Glu Phe Gly Phe His Pro
    1895                    1900                    1905

Asn Ala Glu Trp Ile Leu Lys Thr Leu Val Asn Thr Glu His Ala
    1910                    1915                    1920

Tyr Glu Asn Lys Arg Ile Thr Val Glu Gly Gly Met Pro Ser Gly
    1925                    1930                    1935

Cys Ser Ala Thr Ser Ile Ile Asn Thr Ile Leu Asn Asn Ile Tyr
    1940                    1945                    1950

Val Leu Tyr Ala Leu Arg Arg His Tyr Glu Gly Val Glu Leu Asp
    1955                    1960                    1965

Thr Tyr Thr Met Ile Ser Tyr Gly Asp Asp Ile Val Val Ala Ser
    1970                    1975                    1980

Asp Tyr Asp Leu Asp Phe Glu Ala Leu Lys Pro His Phe Lys Ser
    1985                    1990                    1995

Leu Gly Gln Thr Ile Thr Pro Ala Asp Lys Ser Asp Lys Gly Phe
    2000                    2005                    2010

Val Leu Gly His Ser Ile Thr Asp Val Thr Phe Leu Lys Arg His
    2015                    2020                    2025

Phe His Met Asp Tyr Gly Thr Gly Phe Tyr Lys Pro Val Met Ala
    2030                    2035                    2040

Ser Lys Thr Leu Glu Ala Ile Leu Ser Phe Ala Arg Arg Gly Thr
    2045                    2050                    2055

Ile Gln Glu Lys Leu Ile Ser Val Ala Gly Leu Ala Val His Ser
    2060                    2065                    2070

Gly Pro Asp Glu Tyr Arg Arg Leu Phe Glu Pro Phe Gln Gly Leu
    2075                    2080                    2085

Phe Glu Ile Pro Ser Tyr Arg Ser Leu Tyr Leu Arg Trp Val Asn
    2090                    2095                    2100

Ala Val Cys Gly Asp Ala
    2105

<210> SEQ ID NO 3
<211> LENGTH: 6327
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 3
ggggccggcc aatccagtcc ggcgaccggc tcgcagaacc aatctggcaa cactggcagc     60
ataattaaca actactacat gcagcaatac cagaactcca tggacacaca gttgggagac    120
aatgccatca gtggaggctc caacgagggc tccacggaca caacttcaac acacacaacc    180
```

```
aacactcaaa caatgactg gttctcgaag ctcgccagtt cagcttttac cggtctgttc    240
ggtgcactgc tcgccgacaa gaagacagag gaaacgacac ttcttgagga ccgcatcctc    300
accacccgca acgggcacac cacctcgacg acccaatcga gtgtgggtgt cacacacggg    360
tactccacag aggaggacca cgttgctggg cccaacacat cgggcctgga gacgcgagtg    420
gtgcaggcag agagattcta caaaaagtac ttgtttgact ggacaacgga caaggcattt    480
ggacacctgg aaaagctgga gctcccgtcc gaccaccacg tgtctttgg acacttggtg     540 gactcgtacg cctatatgag aaatggctgg gatgttgagg tgtccgctgt tggcaaccag    600
ttcaacggcg ggtgcctcct ggtggccatg gtacctgaat ggaaggaatt tgacacacgg    660
gagaaatacc aactcaccct tttcccgcac cagtttatta gccccagaac taacatgact    720
gcccacatca cggtcccta ccttggtgtg aacaggtatg atcagtacaa gaagcataag     780
ccctggacat tggttgtcat ggtcgtgtcg ccacttacgg tcaacaacac tagtgcggca    840
caaatcaagg tctacgccaa catagctccg acctatgttc acgtggccgg tgaactcccc    900
tcgaaagagg ggattttccc ggttgcatgt gcggacggtt acgaggatt ggtgacgaca      960 gacccgaaga cagctgaccc tgcttatggc aaggtgtaca acccgcctag gactaactac    1020
cctgggcgct tcaccaacct gttggacgtg gccgaagcgt gtcccacttt cctctgcttt    1080
gacgacggga aaccgtacgt caccacgcgg acggatgaca cccgactttt ggccaagttt    1140
gacctttccc ttgccgcaaa acatatgtcc aacacatacc tgtcagggat tgctcagtac    1200
tacacacagt actctggcac catcaatttg catttcatgt tcacaggttc cactgattca    1260
aaggcccgat acatggtggc ctacatccca cctggggtgg agacaccacc ggacacacct    1320
gaaagggctg cccactgcat tcacgctgaa tgggacactg gactaaactc caaattcact    1380
ttctcaatcc cgtacgtatc cgccgcggat tacgcgtaca cagcgtctga cacggcagaa    1440
acaatcaacg tacagggatg ggtctgcatc taccaaatta cacacgggaa ggctgaaaat    1500
gacaccttgg tcgtgtcggt tagcgccggc aaagactttg agttgcgcct cccgattgac    1560
ccccgccagc agaccaccgc taccggggaa tcagcagacc cggtcaccac caccgtggag    1620
aactacggcg gtgagacaca aatccagaga cgtcaccaca cggacattgg tttcatcatg    1680
gacagatttg tgaagatcca aagcttgagc ccaacacatg tcattgacct catgcagact    1740
caccaacacg gtctggtggg tgccttgctg cgtgcagcca cgtactactt ttctgacctg    1800
gaaattgttg tacggcacga aggcaatctg acctgggtgc ccaacggcgc ccctgaatca    1860
gccctgttga acaccagcaa ccccactgcc tacaacaagg caccattcac gagactcgct    1920
ctcccctaca ctgcgccgca ccgtgtgctg gcaacagtgt acaacgggac gagtaagtat    1980
gctgtgggtg gttcaggcag aagaggcgac atggggtctc tcgcggcgcg agtcgtgaaa    2040
cagcttcctg cttcatttaa ctacggtgca atcaaggccg acgccatcca cgaacttctc    2100
gtgcgcatga acgggccga gctctactgc cccagaccgc tgttggcaat agaggtgtct    2160
tcgcaagaca ggcacaagca aaagatcatt gcaccagcaa agcagcttct gaatttgac     2220 ctgcttaagc tagccggaga cgttgagtcc aaccctgggc ccttcttctt ctccgacgtt    2280
aggtcaaact tttccaagct ggtagacaca atcaaccaga tgcaggaaga catgtccaca    2340
aagcacggac ctgactttaa ccggttggtg tccgcttttg aggagttggc cactggagtg    2400
aaagccatca ggaccggtct tgacgaggcc aagccctggt acaagcttat caagctcctg    2460
agccgcctgt cgtgcatggc cgctgtgcca gcacggtcaa aggacccagt ccttgtggcc    2520
atcatgctgg ctgacaccgg tctcgagatt ctggacagca ccttcgtcgt gaagaagatc    2580
```

```
tccgactcgc tctccagtct cttccacgtg ccggcccccg tcttcagttt cggagccccg   2640
attctgttag ccgggttggt caaggtcgcc tcgagtttct tccggtccac gcccgaagac   2700
cttgagagag cagagaaaca gctcaaagca cgtgacatca cgacatttt cgccattctc    2760
aagaacggcg agtggctggt caaattgatc cttgccatcc gcgactggat caaggcatgg   2820
atagcctcag aagaaaagtt tgtcaccacg acagacttgg tacctagcat ccttgaaaaa   2880
cagcaggacc tcaacgaccc aagcaagtac aaggaagcca aggagtggct cgacaacgcg   2940
cgccaagcgt gtttgaagag cgggaacgtc cacattgcca acctgtgcaa agtggtcgcc   3000
ccggcaccca gcaggtcgag acccgagccc gtggtcgttt gcctccgtgg caagtccggt   3060
cagggcaaga gtttccttgc aaacgtgctc gcacaagcaa tctctaccca tttcactggc   3120
aggaccgatt cagtttggta ctgcccgcct gaccctgacc acttcgacgg ttacaaccaa   3180
cagactgtcg ttgtgatgga cgatttgggc cagaaccccg acggcaaaga cttcaagtac   3240
ttcgcccaaa tggtttcaac aacggggttc atcccgccca tggcatcgct tgaggataaa   3300
ggcaaaccct tcaacagtaa ggtcatcata gcaaccacca acctgtactc gggcttcacc   3360
ccgaggacta tggtgtgccc tgatgccctg aaccggaggt ttcactttga catcgacgtg   3420
agcgccaagg acgggtacaa aattaacaac aaattggaca tcatcaaagc acttgaagat   3480
actcacacca acccagtggc aatgtttcag tacgactgtg cccttctcaa cggcatggct   3540
gttgaaatga agagaatgca acaagatatg ttcaagcctc aaccacccct tcagaacgtg   3600
taccaactgg ttcaagaggt gattgagcgg gtggagctcc acgagaaggt gtcgagccac   3660
ccgattttca aacagatctc aattccttcc caaaaatccg tgttgtactt cctcattgag   3720
aaaggacagc acgaggcagc aattgaattc tttgagggca tggtgcacga ctccatcaag   3780
gaggagctcc ggccgctcat ccaacaaacc tcatttgtga aacgcgcttt taagcgcctg   3840
aaggaaaact ttgagattgt tgccctatgt ctgaccctcc tggccaacat agtgatcatg   3900
atccgcgaaa ctcgcaagag acagaagatg gtggacgatg cagtgagtga gtacattgag   3960
agagcaaaca tcaccaccga cgacaagact cttgatgagg cggaaaagaa ccctctggaa   4020
accagcggtg ccagcaccgt cggcttcaga gagagacctc tcccaggcca aaaggcgcgt   4080
aatgacgaga actccgagcc cgcccagcct gctgaagagc aaccacaagc tgaaggaccc   4140
tacgctggcc cgatggagag acagaaacca ctgaaagtga agcaaaagc cccggtcgtt   4200
aaggaaggac cttacgaggg accggtgaag aagcctgttg ctttgaaagt gaaagctaag   4260
aacttgatcg tcactgagag tggtgcccca ccgaccgact gcaaaagtt ggtcatgggc   4320
aacaccaagc ccgttgagct catccttgac gggaagacgg tagccatttg ctgtgctact   4380
ggagttttcg gcactgctta cctcgtgcct cgtcatcttt tcgcagaaaa gtacgacaag   4440
atcatgttgg acggcagagc catgacagat agtgactaca gagtgtttga gtttgagatt   4500
aaagtaaaag gacaggacat gctctcagac gctgcgctca tggtgctcca ccgtgggaat   4560
cgcgtgagag acatcacgaa acactttcgt gacacagcaa gaatgaagaa aggcaccccc   4620
gtcgttggtg tgatcaacaa cgccgatgtc gggagactga ttttctctgg tgaagccctt   4680
acctacaagg acattgtagt gtgcatggat ggagacacca tgcctgggct cttttgcctac  4740
aaagccgcaa ccaaggctgg ttattgcgga ggagccgtcc tcgctaagga cggggctgac   4800
acgttcatcg ttggcaccca ctccgctgga ggcaatggcg ttggatactg ctcttgcgtt   4860
tccaggtcca tgcttctcaa gatgaaggca cacgttgacc ccgaaccaca ccacgagggg   4920
```

```
ttgattgttg acaccagaga tgtggaagag cgcgttcacg tgatgcgcaa aaccaagctt    4980
gcacccaccg ttgcgtacgg tgtgttccgt cctgagttcg ggcctgccgc cttgtccaac    5040
aaggacccgc gcctgaacga cggtgttgtc ctcgacgaag tcatcttctc caaacacaag    5100
ggagacacaa agatgtctga ggaagacaaa gcgctgttcc gccgctgtgc tgctgactac    5160
gcgtcacgcc tgcacagcgt gttgggtacg gcaaatgccc cactgagcat ctacgaggca    5220
attaaaggcg ttgatggact cgacgcaatg gaaccagaca ccgcacccgg cctcccctgg    5280
gcactccagg ggaagcgccg tggcgcgctc atcgacttcg agaacggcac tgttggaccc    5340
gaagttgagg ctgccttgaa gctcatggag aaaagagaat acaagtttgc ttgccaaacc    5400
ttcctgaagg acgagattcg cccgatggag aaagtacgtg ccggtaagac tcgcattgtc    5460
gacgtcctac ctgttgaaca catcctctac accaggatga tgattggcag atttgtgca    5520 caaatgcact caaacaacgg accccaaatt ggctcggcgg tcggttgtaa ccctgatgtt    5580
gattggcaaa gatttggcac acacttcgcc caatacagaa acgtgtggga tgtggactat    5640
tcggccttcg atgctaacca ctgcagtgac gccatgaaca tcatgtttga ggaagtgttt    5700
cgcacagaat tcgggttcca cccaaacgct gagtggatcc tgaagactct cgtgaacacg    5760
gaacacgcct atgagaacaa acgcatcact gttgaaggcg ggatgccatc tggttgttcc    5820
gcaacaagca tcatcaacac aattttgaac aacatctacg tgctctacgc tttgcgtaga    5880
cactatgagg gagttgagct ggacacttac accatgatct cttacggaga cgatatcgtg    5940
gtggcaagtg attacgattt ggactttgag gctctcaagc cccacttcaa atcccttggt    6000
caaaccatca ctccagctga caaaagcgac aaaggttttg ttcttggtca ctccattact    6060
gatgtcactt tcctcaaaag acacttccac atggattatg gaactgggtt ttacaaacct    6120
gtgatggcct caaagaccct tgaggctatc ctctcctttg cacgccgtgg gaccatacag    6180
gagaagttga tctccgtggc aggactcgct gttcactctg accagacga gtaccggcgt    6240 ctcttcgagc cctttcaagg cctcttcgag attccaagct acagatcact ttacctgcgt    6300
tgggtgaacg ccgtgtgcgg cgacgca                                       6327
```

<210> SEQ ID NO 4
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus
      (FMDV) and Bovine Rhinovirus Type 2 (BRV2)

<400> SEQUENCE: 4

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110
```

```
Ser Ser Val Gly Val Thr His Gly Tyr Ser Thr Glu Glu Asp His Val
        115                 120                 125

Ala Gly Pro Asn Thr Ser Gly Leu Glu Thr Arg Val Val Gln Ala Glu
        130                 135                 140

Arg Phe Tyr Lys Lys Tyr Leu Phe Asp Trp Thr Thr Asp Lys Ala Phe
145                 150                 155                 160

Gly His Leu Glu Lys Leu Glu Leu Pro Ser Asp His His Gly Val Phe
                165                 170                 175

Gly His Leu Val Asp Ser Tyr Ala Tyr Met Arg Asn Gly Trp Asp Val
                180                 185                 190

Glu Val Ser Ala Val Gly Asn Gln Phe Asn Gly Gly Cys Leu Leu Val
        195                 200                 205

Ala Met Val Pro Glu Trp Lys Glu Phe Asp Thr Arg Glu Lys Tyr Gln
        210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
                260                 265                 270

Thr Val Asn Asn Thr Ser Ala Ala Gln Ile Lys Val Tyr Ala Asn Ile
        275                 280                 285

Ala Pro Thr Tyr Val His Val Ala Gly Glu Leu Pro Ser Lys Glu Gly
        290                 295                 300

Ile Phe Pro Val Ala Cys Ala Asp Gly Tyr Gly Gly Leu Val Thr Thr
305                 310                 315                 320

Asp Pro Lys Thr Ala Asp Pro Ala Tyr Gly Lys Val Tyr Asn Pro Pro
                325                 330                 335

Arg Thr Asn Tyr Pro Gly Arg Phe Thr Asn Leu Leu Asp Val Ala Glu
                340                 345                 350

Ala Cys Pro Thr Phe Leu Cys Phe Asp Asp Gly Lys Pro Tyr Val Thr
        355                 360                 365

Thr Arg Thr Asp Asp Thr Arg Leu Leu Ala Lys Phe Asp Leu Ser Leu
        370                 375                 380

Ala Ala Lys His Met Ser Asn Thr Tyr Leu Ser Gly Ile Ala Gln Tyr
385                 390                 395                 400

Tyr Thr Gln Tyr Ser Gly Thr Ile Asn Leu His Phe Met Phe Thr Gly
                405                 410                 415

Ser Thr Asp Ser Lys Ala Arg Tyr Met Val Ala Tyr Ile Pro Pro Gly
                420                 425                 430

Val Glu Thr Pro Pro Asp Thr Pro Glu Arg Ala Ala His Cys Ile His
        435                 440                 445

Ala Glu Trp Asp Thr Gly Leu Asn Ser Lys Phe Thr Phe Ser Ile Pro
        450                 455                 460

Tyr Val Ser Ala Ala Asp Tyr Ala Tyr Thr Ala Ser Asp Thr Ala Glu
465                 470                 475                 480

Thr Ile Asn Val Gln Gly Trp Val Cys Ile Tyr Gln Ile Thr His Gly
                485                 490                 495

Lys Ala Glu Asn Asp Thr Leu Val Val Ser Val Ser Ala Gly Lys Asp
                500                 505                 510

Phe Glu Leu Arg Leu Pro Ile Asp Pro Arg Gln Gln Thr Thr Ala Thr
        515                 520                 525
```

```
Gly Glu Ser Ala Asp Pro Val Thr Thr Thr Val Glu Asn Tyr Gly Gly
            530                 535                 540

Glu Thr Gln Ile Gln Arg Arg His His Thr Asp Ile Gly Phe Ile Met
545                 550                 555                 560

Asp Arg Phe Val Lys Ile Gln Ser Leu Ser Pro Thr His Val Ile Asp
                565                 570                 575

Leu Met Gln Thr His Gln His Gly Leu Val Gly Ala Leu Leu Arg Ala
            580                 585                 590

Ala Thr Tyr Tyr Phe Ser Asp Leu Glu Ile Val Arg His Glu Gly
        595                 600                 605

Asn Leu Thr Trp Val Pro Asn Gly Ala Pro Glu Ser Ala Leu Leu Asn
            610                 615                 620

Thr Ser Asn Pro Thr Ala Tyr Asn Lys Ala Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Ser Lys Tyr Ala Val Gly Gly Ser Gly Arg Arg Gly Asp Met Gly
            660                 665                 670

Ser Leu Ala Ala Arg Val Val Lys Gln Leu Pro Ala Ser Phe Asn Tyr
        675                 680                 685

Gly Ala Ile Lys Ala Asp Ala Ile His Glu Leu Leu Val Arg Met Lys
    690                 695                 700

Arg Ala Glu Leu Tyr Cys Pro Arg Pro Leu Leu Ala Ile Glu Val Ser
705                 710                 715                 720

Ser Gln Asp Arg His Lys Gln Lys Ile Ile Ala Pro Ala Lys Gln Leu
                725                 730                 735

Leu Asn Phe Asp Leu Leu Lys Leu Ala Gly Asp Val Glu Ser Asn Pro
            740                 745                 750

Gly Pro Phe Phe Phe Ser Asp Val Arg Ser Asn Phe Ser Lys Leu Val
        755                 760                 765

Asp Thr Ile Asn Gln Met Gln Glu Asp Met Ser Thr Lys His Gly Pro
770                 775                 780

Asp Phe Asn Arg Leu Val Ser Ala Phe Glu Glu Leu Ala Thr Gly Val
785                 790                 795                 800

Lys Ala Ile Arg Thr Gly Leu Asp Glu Ala Lys Pro Trp Tyr Lys Leu
                805                 810                 815

Ile Lys Leu Leu Ser Arg Leu Ser Cys Met Ala Val Ala Ala Arg
            820                 825                 830

Ser Lys Asp Pro Val Leu Val Ala Ile Met Leu Ala Asp Thr Gly Leu
        835                 840                 845

Glu Ile Leu Asp Ser Thr Phe Val Val Lys Ile Ser Asp Ser Leu
    850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
            900                 905                 910

Ile Asn Asp Ile Phe Ala Ile Leu Lys Asn Gly Glu Trp Leu Val Lys
        915                 920                 925

Leu Ile Leu Ala Ile Arg Asp Trp Ile Lys Ala Trp Ile Ala Ser Glu
    930                 935                 940

Glu Lys Phe Val Thr Thr Thr Asp Leu Val Pro Ser Ile Leu Glu Lys
```

```
945                 950                 955                 960
Gln Gln Asp Leu Asn Asp Pro Ser Lys Tyr Lys Glu Ala Lys Glu Trp
                965                 970                 975
Leu Asp Asn Ala Arg Gln Ala Cys Leu Lys Ser Gly Asn Val His Ile
                980                 985                 990
Ala Asn Leu Cys Lys Val Val Ala Pro Ala Pro Ser Arg Ser Arg Pro
                995                 1000                1005
Glu Pro Val Val Val Cys Leu Arg Gly Lys Ser Gly Gln Gly Lys
    1010                1015                1020
Ser Phe Leu Ala Asn Val Leu Ala Gln Ala Ile Ser Thr His Phe
    1025                1030                1035
Thr Gly Arg Thr Asp Ser Val Trp Tyr Cys Pro Pro Asp Pro Asp
    1040                1045                1050
His Phe Asp Gly Tyr Asn Gln Gln Thr Val Val Val Met Asp Asp
    1055                1060                1065
Leu Gly Gln Asn Pro Asp Gly Lys Asp Phe Lys Tyr Phe Ala Gln
    1070                1075                1080
Met Val Ser Thr Thr Gly Phe Ile Pro Pro Met Ala Ser Leu Glu
    1085                1090                1095
Asp Lys Gly Lys Pro Phe Asn Ser Lys Val Ile Ile Ala Thr Thr
    1100                1105                1110
Asn Leu Tyr Ser Gly Phe Thr Pro Arg Thr Met Val Cys Pro Asp
    1115                1120                1125
Ala Leu Asn Arg Arg Phe His Phe Asp Ile Asp Val Ser Ala Lys
    1130                1135                1140
Asp Gly Tyr Lys Ile Asn Asn Lys Leu Asp Ile Ile Lys Ala Leu
    1145                1150                1155
Glu Asp Thr His Thr Asn Pro Val Ala Met Phe Gln Tyr Asp Cys
    1160                1165                1170
Ala Leu Leu Asn Gly Met Ala Val Glu Met Lys Arg Met Gln Gln
    1175                1180                1185
Asp Met Phe Lys Pro Gln Pro Pro Leu Gln Asn Val Tyr Gln Leu
    1190                1195                1200
Val Gln Glu Val Ile Glu Arg Val Glu Leu His Glu Lys Val Ser
    1205                1210                1215
Ser His Pro Ile Phe Lys Gln Ile Ser Ile Pro Ser Gln Lys Ser
    1220                1225                1230
Val Leu Tyr Phe Leu Ile Glu Lys Gly Gln His Glu Ala Ala Ile
    1235                1240                1245
Glu Phe Phe Glu Gly Met Val His Asp Ser Ile Lys Glu Glu Leu
    1250                1255                1260
Arg Pro Leu Ile Gln Gln Thr Ser Phe Val Lys Arg Ala Phe Lys
    1265                1270                1275
Arg Leu Lys Glu Asn Phe Glu Ile Val Ala Leu Cys Leu Thr Leu
    1280                1285                1290
Leu Ala Asn Ile Val Ile Met Ile Arg Glu Thr Arg Lys Arg Gln
    1295                1300                1305
Lys Met Val Asp Asp Ala Val Ser Glu Tyr Ile Glu Arg Ala Asn
    1310                1315                1320
Ile Thr Thr Asp Asp Lys Thr Leu Asp Glu Ala Glu Lys Asn Pro
    1325                1330                1335
Leu Glu Thr Ser Gly Ala Ser Thr Val Gly Phe Arg Glu Arg Pro
    1340                1345                1350
```

```
Leu Pro Gly Gln Lys Ala Arg Asn Asp Glu Asn Ser Glu Pro Ala
    1355                1360                1365
Gln Pro Ala Glu Glu Gln Pro Gln Ala Glu Gly Pro Tyr Ala Gly
    1370                1375                1380
Pro Met Glu Arg Gln Lys Pro Leu Lys Val Lys Ala Lys Ala Pro
    1385                1390                1395
Val Val Lys Glu Gly Pro Tyr Glu Gly Pro Val Lys Lys Pro Val
    1400                1405                1410
Ala Leu Lys Val Lys Ala Lys Asn Leu Ile Val Thr Glu Ser Gly
    1415                1420                1425
Ala Pro Pro Thr Asp Leu Gln Lys Leu Val Met Gly Asn Thr Lys
    1430                1435                1440
Pro Val Glu Leu Ile Leu Asp Gly Lys Thr Val Ala Ile Cys Cys
    1445                1450                1455
Ala Thr Gly Val Phe Gly Thr Ala Tyr Leu Val Pro Arg His Leu
    1460                1465                1470
Phe Ala Glu Lys Tyr Asp Lys Ile Met Leu Asp Gly Arg Ala Met
    1475                1480                1485
Thr Asp Ser Asp Tyr Arg Val Phe Glu Phe Glu Ile Lys Val Lys
    1490                1495                1500
Gly Gln Asp Met Leu Ser Asp Ala Ala Leu Met Val Leu His Arg
    1505                1510                1515
Gly Asn Arg Val Arg Asp Ile Thr Lys His Phe Arg Asp Thr Ala
    1520                1525                1530
Arg Met Lys Lys Gly Thr Pro Val Val Gly Val Ile Asn Asn Ala
    1535                1540                1545
Asp Val Gly Arg Leu Ile Phe Ser Gly Glu Ala Leu Thr Tyr Lys
    1550                1555                1560
Asp Ile Val Val Cys Met Asp Gly Asp Thr Met Pro Gly Leu Phe
    1565                1570                1575
Ala Tyr Lys Ala Ala Thr Lys Ala Gly Tyr Cys Gly Gly Ala Val
    1580                1585                1590
Leu Ala Lys Asp Gly Ala Asp Thr Phe Ile Val Gly Thr His Ser
    1595                1600                1605
Ala Gly Gly Asn Gly Val Gly Tyr Cys Ser Cys Val Ser Arg Ser
    1610                1615                1620
Met Leu Leu Lys Met Lys Ala His Val Asp Pro Glu Pro His His
    1625                1630                1635
Glu Gly Leu Ile Val Asp Thr Arg Asp Val Glu Glu Arg Val His
    1640                1645                1650
Val Met Arg Lys Thr Lys Leu Ala Pro Thr Val Ala Tyr Gly Val
    1655                1660                1665
Phe Arg Pro Glu Phe Gly Pro Ala Ala Leu Ser Asn Lys Asp Pro
    1670                1675                1680
Arg Leu Asn Asp Gly Val Val Leu Asp Glu Val Ile Phe Ser Lys
    1685                1690                1695
His Lys Gly Asp Thr Lys Met Ser Glu Glu Asp Lys Ala Leu Phe
    1700                1705                1710
Arg Arg Cys Ala Ala Asp Tyr Ala Ser Arg Leu His Ser Val Leu
    1715                1720                1725
Gly Thr Ala Asn Ala Pro Leu Ser Ile Tyr Glu Ala Ile Lys Gly
    1730                1735                1740
```

Val Asp Gly Leu Asp Ala Met Glu Pro Asp Thr Ala Pro Gly Leu
1745                1750                1755

Pro Trp Ala Leu Gln Gly Lys Arg Arg Gly Ala Leu Ile Asp Phe
1760                1765                1770

Glu Asn Gly Thr Val Gly Pro Glu Val Glu Ala Ala Leu Lys Leu
1775                1780                1785

Met Glu Lys Arg Glu Tyr Lys Phe Ala Cys Gln Thr Phe Leu Lys
1790                1795                1800

Asp Glu Ile Arg Pro Met Glu Lys Val Arg Ala Gly Lys Thr Arg
1805                1810                1815

Ile Val Asp Val Leu Pro Val Glu His Ile Leu Tyr Thr Arg Met
1820                1825                1830

Met Ile Gly Arg Phe Cys Ala Gln Met His Ser Asn Asn Gly Pro
1835                1840                1845

Gln Ile Gly Ser Ala Val Gly Cys Asn Pro Asp Val Asp Trp Gln
1850                1855                1860

Arg Phe Gly Thr His Phe Ala Gln Tyr Arg Asn Val Trp Asp Val
1865                1870                1875

Asp Tyr Ser Ala Phe Asp Ala Asn His Cys Ser Asp Ala Met Asn
1880                1885                1890

Ile Met Phe Glu Glu Val Phe Arg Thr Glu Phe Gly Phe His Pro
1895                1900                1905

Asn Ala Glu Trp Ile Leu Lys Thr Leu Val Asn Thr Glu His Ala
1910                1915                1920

Tyr Glu Asn Lys Arg Ile Thr Val Glu Gly Gly Met Pro Ser Gly
1925                1930                1935

Cys Ser Ala Thr Ser Ile Ile Asn Thr Ile Leu Asn Asn Ile Tyr
1940                1945                1950

Val Leu Tyr Ala Leu Arg Arg His Tyr Glu Gly Val Glu Leu Asp
1955                1960                1965

Thr Tyr Thr Met Ile Ser Tyr Gly Asp Asp Ile Val Val Ala Ser
1970                1975                1980

Asp Tyr Asp Leu Asp Phe Glu Ala Leu Lys Pro His Phe Lys Ser
1985                1990                1995

Leu Gly Gln Thr Ile Thr Pro Ala Asp Lys Ser Asp Lys Gly Phe
2000                2005                2010

Val Leu Gly His Ser Ile Thr Asp Val Thr Phe Leu Lys Arg His
2015                2020                2025

Phe His Met Asp Tyr Gly Thr Gly Phe Tyr Lys Pro Val Met Ala
2030                2035                2040

Ser Lys Thr Leu Glu Ala Ile Leu Ser Phe Ala Arg Arg Gly Thr
2045                2050                2055

Ile Gln Glu Lys Leu Ile Ser Val Ala Gly Leu Ala Val His Ser
2060                2065                2070

Gly Pro Asp Glu Tyr Arg Arg Leu Phe Glu Pro Phe Gln Gly Leu
2075                2080                2085

Phe Glu Ile Pro Ser Tyr Arg Ser Leu Tyr Leu Arg Trp Val Asn
2090                2095                2100

Ala Val Cys Gly Asp Ala
2105

<210> SEQ ID NO 5
<211> LENGTH: 40
<212> TYPE: PRT

```
<213> ORGANISM: Foot-and-mouth disease virus

<400> SEQUENCE: 5

Gly Leu Ile Val Asp Thr Arg Asp Val Glu Arg Val His Val Met
1               5                   10                  15
Arg Lys Thr Lys Leu Ala Pro Thr Val Ala His Gly Val Phe Asn Pro
            20                  25                  30
Glu Phe Gly Pro Ala Ala Leu Ser
        35                  40

<210> SEQ ID NO 6
<211> LENGTH: 40
<212> TYPE: PRT
<213> ORGANISM: Foot-and-mouth disease virus

<400> SEQUENCE: 6

Gly Leu Ile Val Asp Thr Arg Asp Val Glu Arg Val His Val Met
1               5                   10                  15
Arg Lys Thr Lys Leu Ala Pro Thr Val Ala Tyr Gly Val Phe Arg Pro
            20                  25                  30
Glu Phe Gly Pro Ala Ala Leu Ser
        35                  40

<210> SEQ ID NO 7
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 7
accgttgcgt acggtgtgtt ccgtcctgag ttcggg                          36

<210> SEQ ID NO 8
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 8
cccgaactca ggacggaaca caccgtacgc aacggt                          36

<210> SEQ ID NO 9
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 9
cgagccacag gaaggatggg ggccggccaa tccag                           35

<210> SEQ ID NO 10
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 10
ctggattggc cggccccat ccttcctgtg gctcg                            35
```

<210> SEQ ID NO 11
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 11
gacctgctta agctagccgg agacgttga                              29

<210> SEQ ID NO 12
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 12
tcaacgtctc cggctagctt aagcaggtc                              29

<210> SEQ ID NO 13
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 13
gcccgatgga gagaccagtt aaagttaaag tgaaagcaaa agcc             44

<210> SEQ ID NO 14
<211> LENGTH: 44
<212> TYPE: DNA
<213> ORGANISM: Artificial Sequence
<220> FEATURE:
<223> OTHER INFORMATION: Chemically Synthesized

<400> SEQUENCE: 14
ggcttttgct ttcactttaa ctttaactgg tctctccatc gggc             44

<210> SEQ ID NO 15
<211> LENGTH: 24
<212> TYPE: PRT
<213> ORGANISM: Foot-and-mouth disease virus

<400> SEQUENCE: 15

Gly Pro Tyr Ala Gly Pro Met Glu Arg Gln Lys Pro Leu Lys Val Arg
1               5                   10                  15

Ala Lys Ala Pro Val Val Lys Glu
            20

<210> SEQ ID NO 16
<211> LENGTH: 24
<212> TYPE: PRT
<213> ORGANISM: Foot-and-mouth disease virus

<400> SEQUENCE: 16

Gly Pro Tyr Ala Gly Pro Met Glu Pro Val Lys Val Leu Lys Val Arg
1               5                   10                  15

Ala Lys Ala Pro Val Val Lys Glu
            20

<210> SEQ ID NO 17
<211> LENGTH: 36
<212> TYPE: DNA

```
<213> ORGANISM: Artificial Sequence
<220> FEATURE:
<223> OTHER INFORMATION: Chemically Synthesized

<400> SEQUENCE: 17
gcggaattcc cgcggtggag ggttaatcgt tgatac                                36

<210> SEQ ID NO 18
<211> LENGTH: 41
<212> TYPE: DNA
<213> ORGANISM: Artificial Sequence
<220> FEATURE:
<223> OTHER INFORMATION: Chemically Synthesized

<400> SEQUENCE: 18
gcggaattcg gatcctgcgt caccgcacac ggcgttcacc c                          41

<210> SEQ ID NO 19
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 19
gaatgggggc cggccaatcc agt                                              23

<210> SEQ ID NO 20
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 20
gacctgctta agctagccgg agacgttgag                                       30

<210> SEQ ID NO 21
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 21
ccacaggaat gggggccggc caatccag                                         28

<210> SEQ ID NO 22
<211> LENGTH: 55
<212> TYPE: DNA
<213> ORGANISM: Artificial Sequence
<220> FEATURE:
<223> OTHER INFORMATION: Chemically Synthesized

<400> SEQUENCE: 22
tctccggcta gcttaagcag gtcaaaattc agaagctgct tctcaggtgc aatga           55

<210> SEQ ID NO 23
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 23
gcctggcaag ttctgcattc agtgg                                            25
```

<210> SEQ ID NO 24
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 24

```
ccactgaatg cagaacttgc caggc                                          25
```

<210> SEQ ID NO 25
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 25

```
tctccggcta gcttaagcag gtcaaaattc agaagttgtt ttgcaggtgc a             51
```

<210> SEQ ID NO 26
<211> LENGTH: 7589
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 26

```
ttgaaagggg gcgctagggt ctcaccccta gcatgccaac gacagtcccc gcgttgcact    60
ccacactcac gttgtgcgtg cgcggagctc gatggactat cgttcaccca cctacagctg   120
gactcacggc accgtgtggc acttggctg a ttgtgcgg acgaacaccg cttgcgcttc    180
tcgcgtgacc ggttagtact ctcaccacct tccgcccact tggttgttag cgctgtcttg   240
ggcactcctg ttgggggccg ttcgacgctc cgcgagtttc cccgcacggc aactacggtg   300
atggggccgt accgcgcggg ctgatcgcct ggtgtgcttc ggctgtcacc cgaagcctac   360
cttttcaccc ccccccccccc cccccccccc cccccccccc cccccccta a gttctaccgt   420
cgttcccgac gtaaagggat gtaaccacaa gcttactacc gcctttcccg gcgttaaagg    480
gatgtaacca aagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa accgtgcaat ttgaaactcc    660
gcctgggctt tccaggtcta gagggtgac gctttgtact gtgtttgact ccacgttcga    720
tccactggcg agtgttagta acaacactgc tgcttcgtag cggagcatga cggccgtggg    780
accccccccc ttggtaacaa ggaccacgg ggccaaaagc cacgtccgaa tggacccgtc     840
atgtgtgcaa acccagcaca gtagctttgt tgtgaaactc actttaaagt gacattgata    900
ctggtactca agcactggtg acaggctaag gatgcccttc aggtacccg aggtaacacg     960
tgacactcgg gatctgagaa gggaccggg gcttctataa aagcgcccgg tttaaaaagc    1020
ttctatgtct gaataggtga ccggaggccg gcacctttct tttaattaca ctggacttat   1080
gaacacaact gattgtttta tcgctttggt acacgctatc agagagatca gagcattttt   1140
cctaccacga gccacaggaa tggggccgg ccaatccagt ccggcaaccg ggtcacagaa    1200
ccaatctggc aacactggaa gcatcattaa caactactac atgcaacagt accagaattc    1260
catggacaca cagcttggtg acaacgctat tagcggaggt tccaacgaag gttccacgga   1320
```

```
taccacttcc acacacacaa acaacaccca aaacaacgac tggttctcgc gcctggcaag   1380
ttctgcattc agtggtctct ttggtgcact tttggctgac aagaagacag aagagacaac   1440
tctgcttgaa gaccgcattc tcaccaccag gaacggccac acaacatcga cgacacagtc   1500
gagcgttggc gtaacatacg gttacgctgt ggccgaggac gcggtgtctg gacccaatac   1560
ctcgggtcta gagactcgtg ttcaacaggc agaacggttt ttcaagaaac acctgtttga   1620
ctggacaccg aacttggcat ttggacactg ttactacctg gaacttccca ctgaacacaa   1680
aggcgtgtac ggcagtctca tgggctcgta cgcctacatg agaaatggat gggacataga   1740
ggtgactgct gttggaaacc aattcaacgg tggttgtctc cttgtcgcgc tcgtgccaga   1800
gctgaaggaa ctcgacacgc gacagaagta ccagctgacc ctctttcccc accagttcat   1860
caacccacgc accaacatga cggcccacat caacgtgccg tacgtgggta tcaacaggta   1920
cgaccagtac gccctccaca agccgtggac gcttgttgtg atggtggtag ccccactcac   1980
cgtcaaaact ggtggttctg aacagatcaa ggtttacatg aatgcagcgc caacctacgt   2040
gcatgtggcg ggagagctgc cctcgaaaga gggaatagtt cccgtcgcgt gtgcggacgg   2100
ttacggcaac atggtgacca cggacccgaa gacggccgat ccagtttacg ggaaagtgtt   2160
caacccccc aggacaaacc tccctgggcg cttcacgaac ttccttgatg ttgcggaggc   2220
atgtccaact ttcctccgct ttggagaagt accatttgtg aagacggtga actctggtga   2280
ccgcttgctg gccaagttcg acgtgtccct cgctgcaggg cacatgtcca acacctactt   2340
ggctggcctg gcgcagtact acacacagta cagcggcacc atgaacgtcc acttcatgtt   2400
caccgggccc acggatgcta agcccgata catggtggct tatgtccccc ctggcatgac   2460
accgccacg gaccctgagc acgccgcaca ctgcattcac tctgagtggg atactggtct   2520
taactctaag tttaccttttt ccatacctta cctctctgct gctgactatg cctacactgc   2580
ttctgacgtg gcggagacca cgagtgtgca gggatgggtg tgtatctatc agatcaccca   2640
cggcaaggct gagggagacg cactggtcgt ttctgtcagc gccggcaaag actttgagtt   2700
tcgcttgcct gttgacgcac gccagcaaac caccaccact ggcgaatcag cagatccagt   2760
cacaaccacg gttgagaact atggaggaga gactcagaca gccagacggc ttcacactga   2820
cgtcgccttc attcttgaca ggtttgtgaa actcactgct cccaagaaca tccaaaccct   2880
cgatctcatg cagatcccct cacacacgct ggttggagca ctacttcgtt ctgcgacgta   2940
ctacttctca gacctggagg tcgcgcttgt ccacacaggc ccggtcacct gggtgcccaa   3000
cggcgcgccc aaggatgctc taaacaacca gaccaaccca actgcctatc agaagcaacc   3060
catcacccgc ctggcactcc cctacaccgc ccccatcgt gtgctggcaa cagtgtacaa   3120
cgggaagacg gcgtacgggg aaacgacctc aaggcgcggc gacatggcgg ccctcgcaca   3180
aaggttgagc gctcggctgc ccacctcctt caactacggc gccgtgaagg ccgacaccat   3240
cactgagctt ttgatccgca tgaagcgcgc ggagacatat tgccctaggc ctttactagc   3300
ccttgacacc actcaggacc gccgcaaaca ggagatcatt gcacctgaga agcagcttct   3360
gaattttgac ctgcttaagc tagccggaga cgttgagtcc aaccctgggc ccttcttctt   3420
ctccgacgtt aggtcaaaact tttccaagct ggtagacaca atcaaccaga tgcaggaaga   3480
catgtccaca aagcacggac ctgactttaa ccggttggtg tccgcttttg aggagttggc   3540
cactggagtg aaagccatca ggaccggtct tgacgaggcc aagccctggt acaagcttat   3600
caagctcctg agccgcctgt cgtgcatggc cgctgtggca gcacggtcaa aggacccagt   3660
```

```
ccttgtggcc atcatgctgg ctgacaccgg tctcgagatt ctggacagca ccttcgtcgt    3720
gaagaagatc tccgactcgc tctccagtct cttccacgtg ccggcccccg tcttcagttt    3780
cggagccccg attctgttag ccgggttggt caaggtcgcc tcgagtttct tccggtccac    3840
gcccgaagac cttgagagag cagagaaaca gctcaaagca cgtgacatca acgacatttt    3900
cgccattctc aagaacggcg agtggctggt caaattgatc cttgccatcc gcgactggat    3960
caaggcatgg atagcctcag aagaaaagtt tgtcaccacg acagacttgg tacctagcat    4020
ccttgaaaaa cagcaggacc tcaacgaccc aagcaagtac aaggaagcca aggagtggct    4080
cgacaacgcg cgccaagcgt gtttgaagag cgggaacgtc cacattgcca acctgtgcaa    4140
agtggtcgcc ccggcaccca gcaggtcgag acccgagccc gtggtcgttt gcctccgtgg    4200
caagtccggt cagggcaaga gtttccttgc aaacgtgctc gcacaagcaa tctctaccca    4260
tttcactggc aggaccgatt cagtttggta ctgcccgcct gaccctgacc acttcgacgg    4320
ttacaaccaa cagactgtcg ttgtgatgga cgatttgggc cagaaccccg acggcaaaga    4380
cttcaagtac ttcgcccaaa tggtttcaac aacggggttc atcccgccca tggcatcgct    4440
tgaggataaa ggcaaaccct caacagtaa ggtcatcata gcaaccacca acctgtactc    4500
gggcttcacc ccgaggacta tggtgtgccc tgatgccctg aaccggaggt ttcactttga    4560
catcgacgtg agcgccaagg acgggtacaa aattaacaac aaattggaca tcatcaaagc    4620
acttgaagat actcacacca acccagtggc aatgtttcag tacgactgtg cccttctcaa    4680
cggcatggct gttgaaatga agagaatgca acaagatatg ttcaagcctc aaccacccct    4740
tcagaacgtg taccaactgg ttcaagaggt gattgagcgg gtggagctcc acgagaaggt    4800
gtcgagccac ccgattttca aacagatctc aattccttcc caaaaatccg tgttgtactt    4860
cctcattgag aaaggacagc acgaggcagc aattgaattc tttgagggca tggtgcacga    4920
ctccatcaag gaggagctcc ggccgctcat ccaacaaacc tcatttgtga aacgcgcttt    4980
taagcgcctg aaggaaaact ttgagattgt tgccctatgt ctgaccctcc tggccaacat    5040
agtgatcatg atccgcgaaa ctcgcaagag acagaagatg gtggacgatg cagtgagtga    5100
gtacattgag agagcaaaca tcaccaccga cgacaagact cttgatgagg cggaaaagaa    5160
ccctctggaa accagcggtg ccagcaccgt cggcttcaga gagagacctc tcccaggcca    5220
aaaggcgcgt aatgacgaga actccgagcc cgcccagcct gctgaagagc aaccacaagc    5280
tgaaggaccc tacgctggcc cgatggagag accagttaaa gttaaagtga agcaaaagc    5340
cccggtcgtt aaggaaggac cttacgaggg accggtgaag aagcctgttg ctttgaaagt    5400
gaaagctaag aacttgatcg tcactgagag tggtgccccca ccgaccgact tgcaaaagtt    5460
ggtcatgggc aacaccaagc ccgttgagct catccttgac gggaagacgg tagccatttg    5520
ctgtgctact ggagttttcg gcactgctta cctcgtgcct cgtcatcttt tcgcagaaaa    5580
gtacgacaag atcatgttgg acggcagagc catgacagat agtgactaca gagtgtttga    5640
gtttgagatt aaagtaaaag gacaggacat gctctcagac gctgcgctca tggtgctcca    5700
ccgtgggaat cgcgtgagag acatcacgaa acactttcgt gacacagcaa gaatgaagaa    5760
aggcaccccc gtcgttggtg tgatcaacaa cgccgatgtc gggagactga ttttctctgg    5820
tgaagccctt acctacaagg acattgtagt gtgcatggat ggagacacca tgcctgggct    5880
ctttgcctac aaagccgcaa ccaaggctgg ttattgcgga ggagccgtcc tcgctaagga    5940
cggggctgac acgttcatcg ttggcaccca ctccgctgga ggcaatggcg ttggatactg    6000
ctcttgcgtt tccaggtcca tgcttctcaa gatgaaggca cacgttgacc ccgaaccaca    6060
```

```
ccacgagggg ttgattgttg acaccagaga tgtggaagag cgcgttcacg tgatgcgcaa    6120
aaccaagctt gcacccaccg ttgcgtacgg tgtgttccgt cctgagttcg ggcctgccgc    6180
cttgtccaac aaggacccgc gcctgaacga cggtgttgtc ctcgacgaag tcatcttctc    6240
caaacacaag ggagacacaa agatgtctga ggaagacaaa gcgctgttcc gccgctgtgc    6300
tgctgactac gcgtcacgcc tgcacagcgt gttgggtacg gcaaatgccc cactgagcat    6360
ctacgaggca attaaaggcg ttgatggact cgacgcaatg gaaccagaca ccgcacccgg    6420
cctcccctgg gcactccagg ggaagcgccg tggcgcgctc atcgacttcg agaacggcac    6480
tgttggaccc gaagttgagg ctgccttgaa gctcatggag aaaagagaat acaagtttgc    6540
ttgccaaacc ttcctgaagg acgagattcg cccgatggag aaagtacgtg ccggtaagac    6600
tcgcattgtc gacgtcctac ctgttgaaca catcctctac accaggatga tgattggcag    6660
attttgtgca caaatgcact caaacaacgg accccaaatt ggctcggcgg tcggttgtaa    6720
ccctgatgtt gattgcaaa gatttggcac acacttcgcc caatacagaa acgtgtggga    6780
tgtggactat tcggccttcg atgctaacca ctgcagtgac gccatgaaca tcatgtttga    6840
ggaagtgttt cgcacagaat tcgggttcca cccaaacgct gagtggatcc tgaagactct    6900
cgtgaacacg gaacacgcct atgagaacaa acgcatcact gttgaaggcg ggatgccatc    6960
tggttgttcc gcaacaagca tcatcaacac aatttttgaac aacatctacg tgctctacgc    7020
tttgcgtaga cactatgagg gagttgagct ggacacttac accatgatct cttacggaga    7080
cgatatcgtg gtggcaagtg attacgattt ggactttgag gctctcaagc cccacttcaa    7140
atcccttggt caaaccatca ctccagctga caaaagcgac aaaggttttg ttcttggtca    7200
ctccattact gatgtcactt tcctcaaaag acacttccac atggattatg aactgggtt    7260 ttacaaacct gtgatggcct caaagaccct tgaggctatc ctctcctttg cacgccgtgg    7320
gaccatacag gagaagttga tctccgtggc aggactcgct gttcactctg accagacga    7380 gtaccggcgt ctcttcgagc ccttcaagg cctcttcgag attccaagct acagatcact    7440
ttacctgcgt tgggtgaacg ccgtgtgcgg cgacgcataa tccctcagag actacattgg    7500
catactgttt ctgaggcgcg cgacgccgta ggagtgaaaa gcctgaaagg cttttcccg    7560 cttcctattc caaaaaaaaa aaaaaaaa                                      7589
```

<210> SEQ ID NO 27
<211> LENGTH: 7600
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 27

```
ttgaaggggg cgctagggt ctcacccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggtagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360 cttttcacccc cccccccccc cccccccccc cccccctaa gttctaccgt                420 cgttcccgac gtaaagggat gtaaccacaa gcttactacc gcctttcccg gcgttaaagg    480
```

```
gatgtaaccaa caagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa accgtgcaat ttgaaactcc    660
gcctgggctt tccaggtcta gaggggtgac gctttgtact gtgtttgact ccacgttcga    720
tccactggcg agtgttagta acaacactgc tgcttcgtag cggagcatga cggccgtggg    780
accccccccc ttggtaacaa ggacccacgg ggccaaaagc cacgtccgaa tggacccgtc    840
atgtgtgcaa acccagcaca gtagctttgt tgtgaaactc actttaaagt gacattgata    900
ctggtactca agcactggtg acaggctaag gatgcccttc aggtaccccg aggtaacacg    960
tgacactcgg gatctgagaa ggggaccggg gcttctataa aagcgcccgg tttaaaaagc   1020
ttctatgtct gaataggtga ccggaggccg gcacctttct tttaattaca ctggacttat   1080
gaacacaact gattgtttta tcgctttggt acacgctatc agagagatca gagcattttt   1140
cctaccacga gccacaggaa tgggggccgg ccaatccagt ccggcaaccg ggtcacaaaa   1200
ccaatcaggc aacactggta gtatcatcaa caactactac atgcagcagt accagaactc   1260
catggataca caacttggcg acaacgccat tagcggtggt tccaacgagg gctccactga   1320
cactacctcc acacacacaa ccaacacaca gaacaatgac tggttttcaa agctggccag   1380
ttctgccttc agcggtctct tcggcgctct tctcgctgac aaaaagacag aggagactac   1440
cctcctggag gaccgcatcc ttaccacccg caacggacac accacctcga caacccagtc   1500
gagtgtgggt gtcacctacg ggtactccac tggtgaagac cacgtctctg gacctaacac   1560
atctggcctg gagacgcgag tggtacaggc agagagattc ttcaagaaac acttgtttga   1620
ttggacaact gataaagctt ttggacacct ggaaaaactg gaactcccca ccgaacacaa   1680
gggtgtctac gggcacttgg tggactcttt cgcatacatg agaaatggct gggacgtgga   1740
ggtgaccgcc gttggcaacc agttcaacgg tgggtgtctc ctggtggcca tggtacctga   1800
gtggaaagag tttacccctc gtgagaaata ccagctcacc ctgtttccac accaatttat   1860
caacccagga accaacatga cagcccacat cacggtcccg taccttggtg tcaataggta   1920
tgaccagtac aaacagcaca aaccctggac actggtcgtg atggtggttt cgccactgac   1980
caccagcagc attggggcct cacagattaa ggtctacgcc aacattgccc aaccttcgt   2040 tcacgtggcc ggcgagctcc catcgaaaga agggatcgtg ccggttgctt gtacagacgg   2100
gtacggtggc ctggtgacaa cagacccgaa aacagctgac cctgtttatg gtatggtgta   2160
caacccgccc agaaccaact accctgggcg ctttacaaac ttgttggacg tggccgaggc   2220
ttgcccgacc ttcctctgtt ttgacgacgg gaaaccgtac gttgtgacaa ggacggacga   2280
ccaacgcctc ctgccaagt ttgacgtttc ccttgctgca aagcacatgt caaacaccta   2340
cctctcaggg atagcacagt actacacgca gtactctggc actatcaatc tgcatttcat   2400
gttcactggc tctactgaat caaaggcccg gtacatggtg gcgtacattc cacctggcat   2460
ggacaaccca ccggacacac ctgagaaggc tgcacattgc atccacgccg agtgggacac   2520
cgggctgaac tccaaattta cttttctat cccgtacgtg tctgctgcag actacgcata   2580
cactgcgtct gacgtggcag aaacaacaaa cgtacagggg tgggtctgca tataccaaat   2640
cactcacggg aaggctgaac aggacactct ggtcgtgtcg gtcagcgccg gcaaggactt   2700
tgaactgcgc ctcccaattg accccgcac gcaaaccacc actgccgggg agtcagcaga   2760
ccctgtcacc accaccgttg agaactacgg tggtgagaca caggctcagc gacgtcagca   2820
```

```
cactgacgtc ggcttcatca tggacaggtt tgcgaaaatc agccccgtga gccccacgca    2880
cgtcattgac ctcatgcaaa cacaccaaca cgcgttggtg ggtgcccttt tgcgtgcagc    2940
cacgtactac ttctccgatc tggagattgt ggtgcgtcat gatggcaact tgacgtgggt    3000
gcccaatgga gcacctgtag aagccttggc caacacaagc aacccaccg cctaccacaa     3060
gcagccattt acgagacttg cgctccctta caccgcgccg caccgagtgt tggcaacagt    3120
gtataacgga gtaagcaagt actctacaac tggtaatggc agaaggggtg acctggggcc    3180
tcttgcggcg cgggtcgccg cacagctccc cagctctttc aattttggtg caattcgggc    3240
cacgaccgtc cacgagcttc tcgtgcgcat gaaacgtgcc gagctctact gtcccaggcc    3300
tctgctggca gtggaagtgt tgtcgcagga cagacacaag caaaagatca ttgcacctgc    3360
aaagcaactt ctgaattttg acctgcttaa gctagccgga gacgttgagt ccaaccctgg    3420
gcccttcttc ttctccgacg ttaggtcaaa cttttccaag ctggtagaca caatcaacca    3480
gatgcaggaa gacatgtcca caaagcacg acctgacttt aaccggttgg tgtccgcttt     3540
tgaggagttg gccactggag tgaaagccat caggaccggt cttgacgagg ccaagccctg    3600
gtacaagctt atcaagctcc tgagccgcct gtcgtgcatg ccgctgtgg cagcacggtc     3660
aaaggaccca gtccttgtgg ccatcatgct ggctgacacc ggtctcgaga ttctggacag    3720
caccttcgtc gtgaagaaga tctccgactc gctctccagt ctcttccacg tgccggcccc    3780
cgtcttcagt ttcggagccc cgattctgtt agccgggttg gtcaaggtcg cctcgagttt    3840
cttccggtcc acgcccgaag accttgagag agcagagaaa cagctcaaag cacgtgacat    3900
caacgacatt ttcgccattc tcaagaacgg cgagtggctg gtcaaattga tccttgccat    3960
ccgcgactgg atcaaggcat ggatagcctc agaagaaaag tttgtcacca cgacagactt    4020
ggtacctagc atccttgaaa acagcagga cctcaacgac ccaagcaagt acaaggaagc     4080
caaggagtgg ctcgacaacg cgcgccaagc gtgtttgaag agcgggaacg tccacattgc    4140
caacctgtgc aaagtggtcg ccccggcacc cagcaggtcg agacccgagc ccgtggtcgt    4200
ttgcctccgt ggcaagtccg gtcagggcaa gagtttcctt gcaaacgtgc tcgcacaagc    4260
aatctctacc catttcactg gcaggaccga ttcagtttgg tactgcccgc ctgaccctga    4320
ccacttcgac ggttacaacc aacagactgt cgttgtgatg gacgatttgg ccagaaccc     4380
cgacggcaaa gacttcaagt acttcgccca aatggtttca acaacggggt tcatcccgcc    4440
catggcatcg cttgaggata aaggcaaacc cttcaacagt aaggtcatca tagcaaccac    4500
caacctgtac tcgggcttca ccccgaggac tatggtgtgc cctgatgccc tgaaccggag    4560
gtttcacttt gacatcgacg tgagcgccaa ggacgggtac aaaattaaca acaaattgga    4620
catcatcaaa gcacttgaag atactcacac caacccagtg gcaatgtttc agtacgactg    4680
tgcccttctc aacggcatgg ctgttgaaat gaagagaatg caacaagata tgttcaagcc    4740
tcaaccaccc cttcagaacg tgtaccaact ggttcaagag gtgattgagc gggtggagct    4800
ccacgagaag gtgtcgagcc acccgatttt caaacagatc tcaattcctt cccaaaaatc    4860
cgtgttgtac ttcctcattg agaaaggaca gcacgaggca gcaattgaat ctttgaggg     4920
catggtgcac gactccatca aggaggagct ccggccgctc atccaacaaa cctcatttgt    4980
gaaacgcgct tttaagcgcc tgaaggaaaa ctttgagatt gttgccctat gtctgaccct    5040
cctggccaac atagtgatca tgatccgcga aactcgcaag agacagcaga tggtggacga    5100
tgcagtgagt gagtacattg agagagcaaa catcaccacc gacgacaaga ctcttgatga    5160
ggcggaaaag aaccctctgg aaaccagcgg tgccagcacc gtcggcttca gagagagacc    5220
```

```
tctcccaggc caaaaggcgc gtaatgacga gaactccgag cccgcccagc ctgctgaaga   5280
gcaaccacaa gctgaaggac cctacgctgg cccgatggaa agaccagtta aagttaaagt   5340
gaaagcaaaa gccccggtcg ttaaggaagg accttacgag ggaccggtga agaagcctgt   5400
tgctttgaaa gtgaaagcta agaacttgat cgtcactgag agtggtgccc caccgaccga   5460
cttgcaaaag ttggtcatgg gcaacaccaa gcccgttgag ctcatccttg acgggaagac   5520
ggtagccatt tgctgtgcta ctggagtttt cggcactgct tacctcgtgc ctcgtcatct   5580
tttcgcagaa aagtacgaca agatcatgtt ggacggcaga gccatgacag atagtgacta   5640
cagagtgttt gagtttgaga ttaaagtaaa aggacaggac atgctctcag acgctgcgct   5700
catggtgctc caccgtggga atcgcgtgag agacatcacg aaacactttc gtgacacagc   5760
aagaatgaag aaaggcaccc ccgtcgttgg tgtgatcaac aacgccgatg tcgggagact   5820
gattttctct ggtgaagccc ttacctacaa ggacattgta gtgtgcatgg atggagacac   5880
catgcctggg ctcttttgcct acaaagccgc aaccaaggct ggttattgcg gaggagccgt   5940
cctcgctaag gacggggctg acacgttcat cgttggcacc cactccgctg gaggcaatgg   6000
cgttggatac tgctcttgcg tttccaggtc catgcttctc aagatgaagg cacacgttga   6060
ccccgaacca caccacgagg ggttgattgt tgacaccaga gatgtggaag agcgcgttca   6120
cgtgatgcgc aaaaccaagc ttgcacccac cgttgcgtac ggtgtgttcc gtcctgagtt   6180
cgggcctgcc gccttgtcca acaaggaccc gcgcctgaac gacggtgttg tcctcgacga   6240
agtcatcttc tccaaacaca agggagacac aaagatgtct gaggaagaca aagcgctgtt   6300
ccgccgctgt gctgctgact acgcgtcacg cctgcacagc gtgttgggta cggcaaatgc   6360
cccactgagc atctacgagg caattaaagg cgttgatgga ctcgacgcaa tggaaccaga   6420
caccgcaccc ggcctcccct gggcactcca ggggaagcgc cgtggcgcgc tcatcgactt   6480
cgagaacggc actgttggac ccgaagttga ggctgccttg aagctcatgg agaaaagaga   6540
atacaagttt gcttgccaaa ccttcctgaa ggacgagatt cgcccgatgg agaaagtacg   6600
tgccggtaag actcgcattg tcgacgtcct acctgttgaa cacatcctct acaccaggat   6660
gatgattggc agattttgtg cacaaatgca ctcaaacaac ggaccccaaa ttggctcggc   6720
ggtcggttgt aaccctgatg ttgattggca aagatttggc acacacttcg cccaatacag   6780
aaacgtgtgg gatgtggact attcggcctt cgatgctaac cactgcagtg acgccatgaa   6840
catcatgttt gaggaagtgt ttcgcacaga attcgggttc cacccaaacg ctgagtggat   6900
cctgaagact ctcgtgaaca cggaacacgc ctatgagaac aaacgcatca ctgttgaagg   6960
cgggatgcca tctggttgtt ccgcaacaag catcatcaac acaattttga caacatcta   7020 cgtgctctac gctttgcgta gacactatga gggagttgag ctggacactt acaccatgat   7080
ctcttacgga gacgatatcg tggtggcaag tgattacgat ttggactttg aggctctcaa   7140
gccccacttc aaatcccttg gtcaaaccat cactccagct gacaaaagcg acaaaggttt   7200
tgttcttggt cactccatta ctgatgtcac tttcctcaaa agacacttcc acatggatta   7260
tggaactggg tttacaaaac ctgtgatggc ctcaaagacc cttgaggcta tcctctcctt   7320
tgcacgccgt gggaccatac aggagaagtt gatctccgtg gcaggactcg ctgttcactc   7380
tggaccagac gagtaccggc gtctcttcga gccctttcaa ggcctcttcg agattccaag   7440
ctacagatca ctttacctgc gttgggtgaa cgccgtgtgc ggcgacgcat aatccctcag   7500
agactacatt ggcatactgt ttctgaggcg cgcgacgccg taggagtgaa aagcctgaaa   7560
```

```
gggcttttcc cgcttcctat tccaaaaaaa aaaaaaaaa                              7600
```

<210> SEQ ID NO 28
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 28

```
gctgccctcg aaagagggaa tag                                              23
```

<210> SEQ ID NO 29
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 29

```
aaactttttct tctgaggcta tccat                                           25
```

<210> SEQ ID NO 30
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 30

```
agcacagtag ctttgttgtg aaact                                            25
```

<210> SEQ ID NO 31
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 31

```
cgcgccgcaa gaggccccag gt                                               22
```

<210> SEQ ID NO 32
<211> LENGTH: 23
<212> TYPE: DNA
<213> ORGANISM: Foot-and-mouth disease virus

<400> SEQUENCE: 32

```
tgacttccac gcaggcattt tcc                                              23
```

<210> SEQ ID NO 33
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 33

```
tagttaaatg aagcaggaag ctgt                                             24
```

<210> SEQ ID NO 34
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 34
acaactacta catgcagcaa tacca                                    25

<210> SEQ ID NO 35
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 35
agtgaatttg gagtttagtc cagtg                                    25

<210> SEQ ID NO 36
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 36
gctccactga cactacctcc ac                                       22

<210> SEQ ID NO 37
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 37
gccggcgctg accgacacga cc                                       22

<210> SEQ ID NO 38
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 38
ttttcaaaca gatctcaatt ccttc                                    25

<210> SEQ ID NO 39
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 39
gcaagcaaac ttgtattctc ttttc                                    25

DEVELOPMENT OF A MARKER FOOT AND MOUTH DISEASE VIRUS VACCINE CANDIDATE THAT IS ATTENUATED IN THE NATURAL HOST

This application claims the benefit of U.S. Provisional Application No. 61/360,719 filed Jul. 1, 2010, which is incorporated herein by reference in its entirety.

BACKGROUND OF THE INVENTION

1. Field of the Invention

This invention relates to a rationally designed engineered attenuated antigenic marker vaccine-virus production platform comprising a deletion of the $L^{pro}$ coding sequence resulting in complete attenuation and mutations (negative markers) introduced in two non-structural viral proteins resulting in the elimination of two antigenic epitopes recognized by specific antibodies, one located in 3B and the other in 3D, thus providing a target for DIVA (Differentiation of naturally Infected from Vaccinated Animals) serological tests. The attenuated marker vaccine production virus also comprises unique restriction endonuclease sites flanking the capsid-coding region to facilitate the replacement of the capsid region making possible the exchange of cassettes representing relevant capsid coding regions of different serotypes and subtypes of FMDV field isolates for the design of custom vaccines.

2. Description of the Relevant Art

Foot and mouth disease (FMD) is an extremely contagious viral disease of cloven-hoofed ungulates which include domestic animals (cattle, pigs, sheep, goats, and others) and a variety of wild animals. The most prominent disease symptoms in FMDV-infected cattle include vesicular lesions of the epithelium of the mouth, tongue, teats and feet. Although some countries, among them United States, Canada, Mexico, Australia and most of Europe, are considered to be free of FMD, the disease is distributed worldwide and has a great economic impact on the export industry. Indeed, several economically devastating outbreaks have occurred over the past decade on almost every continent.

Control methods to eradicate FMD depend upon the prevalence of the disease in particular geographical regions/states and often include mass annual prophylactic vaccination campaigns and the application of stringent zooprophylactic measures following outbreaks. A chemically inactivated whole virus vaccine has been used to contain the disease, but it is slow acting and does not always permit distinction between infected and vaccinated animals. Indeed, in recent years the differentiation of infected animals from those that have been vaccinated is of paramount importance as a protective activity following emergency vaccination. Historically, the use of non-structural viral protein as serological indicators of viral replication has been widely applied. Among these proteins, the highly conserved FMDV 3D polymerase ($3D^{pol}$) of 52-KDa has been identified as the main determinant of infection and has been called the FMD-Virus Infection-Associated Antigen (FMD-VIAA; Berger et al. 1990. *Vaccine* 8:213-216; Bergmann et al. 1993. *Am. J. Vet. Res.* 54:825-831; Cowan and Graves. 1966. *Virology* 30:528-540; McVicar and Sutmoller. 1970. *Am. J. Epidemiol.* 92:273-278; Sorensen et al. 1998. *Arch. Virol.* 143:1461-1476). Studies by Newman and Brown (1997. *J. Virol.* 71: 7657-7662; Newman et al. 1994. *Proc. Natl. Acad. Sci. USA* 91:733-737) suggested that purified 140S FMDV preparations contain small quantities of $3D^{pol}$ and therefore, could account for seroconversion to $3D^{pol}$ in animals that have received inactivated FMDV vaccines.

Previous strategies to select highly attenuated vaccines for FMDV have relied on the selection of less-pathogenic variants produced by serial passages of the virus in non-natural hosts such as embryonated chicken eggs and rabbits (Giraudo et al. 1990. *Virology* 177:780-783; Xin et al. 2009. *Vet. Microbiol.*). Those empirical strategies failed when tested in susceptible species due to reversion to virulence by the mutant viruses harboring point-mutations and therefore, were not pursued for being too risky (Sutmoller, P. 2001. *Rev. Sci. Tech.* 20:715-722; Sutmoller et al. 2003. *Virus Res.* 91:101-144). Modern approaches to produce genetically engineered FMDV with altered virulence have relied on the deletion of the cell-receptor binding site (Mason et al. 1994. *Proc. Natl. Acad. Sci. USA* 91:1932-1936; McKenna et al. 1995. *J. Virol.* 69:5787-5790; Rieder et al. 1996. *Proc. Natl. Acad. Sci. USA* 93:10428-33), the viral leader coding sequence ($L^{pro}$, Piccone et al. 1995. *J. Virol.* 69:5376-82) or elements within the non-translated region (NTR) (Rodriguez et al. 2009. *J. Virol.* 83:3475-3485). The FMDV $L^{pro}$ together with the $3C^{pro}$ and 2A proteinases play an important role in processing of the viral polyprotein. In addition to cleaving itself from the nascent polyprotein, $L^{pro}$ cleaves the eukaryotic initiation factor 4G (eIF4G) causing inhibition of the cellular translation machinery. $L^{pro}$ is also known to relocate to the nucleus in the FMDV-infected cells and to induce degradation of nuclear factor kappa B (NF-κB) with the consequent inhibition of the innate immune response (de Los Santos et al. 2006. *J. Virol.* 80:1906-1914). FMDVs of serotype A lacking $L^{pro}$ have been shown to be infectious, to grow more slowly in BHK-21 cells ($A_{12}$-LLV2, (Piccone et al., supra) and be attenuated for pigs (Brown et al. 1996. *J. Virol.* 70:5638-5641; Chinsangaram et al. 1998. *Vaccine* 16:1516-1522; Mason et al. 1997. *Virology* 227:96-102).

Currently killed-antigen FMDV vaccines are produced in expensive biological containment facilities, by growing large volumes (thousands of liters) of virulent FMDV that has been adapted to grow in cells, which can be sometimes difficult. This process has resulted in escape of virulent virus from the manufacturing facility causing costly outbreaks in livestock (see Cottam et al. 2008. *PLoS Pathogen* 4:1-8). After growth, virus is then inactivated using chemicals and antigen concentrates are prepared, followed by purification steps required to remove contaminant proteins, making it difficult to differentiate infected from vaccinated animals (DIVA) through serological diagnostic tests. There is little to no cross protection across serotypes and subtypes requiring the appropriate matching between vaccine and circulating field strains to achieve protection. Despite these shortcomings of the vaccines, billions of doses are manufactured every year around the world. Their use has been the basis for eradicating FMDV from Europe and for controlling the disease in many parts of the world through mass vaccination campaigns. Thus, there is an urgent need for the development of effective marker FMDV vaccine candidates with DIVA capabilities.

SUMMARY OF THE INVENTION

We have discovered a novel, safe, molecular-based attenuated FMD virus vaccine platform for FMD control and eradication; the vaccine has negative markers that allows the differentiation of naturally infected animals from vaccinated animals.

In accordance with this discovery, it is an object of the invention to provide a recombinant viral-vectored vaccine platform comprising DNA encoding a genetically modified FMDV vector that is attenuated in the natural host by design comprising mutations (negative markers) introduced in two non-structural viral proteins resulting in the elimination of two antigenic epitopes recognized by specific antibodies, one located in protein 3B and the other in protein 3D, thus providing two possible targets for DIVA (Differentiation of naturally Infected from Vaccinated Animals) serological tests. The vaccine platform also comprises unique restriction endonuclease sites to facilitate the replacement of the capsid region making possible the exchange of cassettes representing relevant capsid coding regions of different serotypes and subtypes of FMDV field isolates.

It is thus an object of the invention to provide an isolated polynucleotide molecule comprising a genetically modified DNA sequence encoding a genetically modified FMDV. The FMDV is genetically modified, i.e., it is a leaderless virus containing a deletion of the leader ($L^{pro}$) protein coding region such that FMD viruses lacking this protein are attenuated in cattle and pigs.

It is additionally an object of the invention to provide a genetically modified FMDV encoded by the isolated polynucleotide molecule recited above and further containing an alteration in the sequence of one or more of the non-structural viral proteins where there is an insertion of a conserved B cell immunodominant epitope in a virus non-structural protein(s) providing a negative marker vaccine that is attenuated in the natural host by design and that can elicit an immune response that can be distinguished from the immune response induced by the field virus.

It is a further object of the invention to provide a genetically modified FMDV encoded by the isolated polynucleotide molecule recited above where the alteration is in the sequence of one of the non-structural viral proteins, $3D^{pol}$, and where the alteration is a substitution at position H27Y and N31R, resulting in the genetically modified FMDV LL[YR].

An added object of the invention is to provide a genetically modified FMDV encoded by the isolated polynucleotide molecule recited above where the alteration is in the sequence of one of the non-structural viral proteins, $3D^{pol}$, and also a mutation in 3B (RQKP→PVKV, found in BRV-2) that abolishes reactivity with MAb F8B.

Another object of the invention is to provide a marker FMDV cDNA clone that is further modified for inclusion of unique restriction endonuclease sites to facilitate the replacement of the capsid region, thus making possible a cassette design allowing for rapid replacement of parental capsid sequences with donor capsid sequences from different FMDV subtypes and serotypes.

An additional object of the invention is to provide a recombinant viral-vectored vaccine platform for production of chemically-inactivated FMD vaccine comprising a genetically modified FMDV comprising deletion of the $L^{pro}$ coding sequence, a mutation in a B cell immunodominant epitope in the virus non-structural protein $3D^{pol}$ or mutations in B cell immunodominant epitopes of both $3D^{pol}$ and 3B viral non-structural proteins, inclusion of unique restriction endonuclease sites to facilitate the replacement of the capsid region of new viral strains.

Another object of the invention is to provide a rationally designed attenuated FMDV vaccine that used in a chemically-inactivated form is effective to protect an animal from clinical FMD when challenged with virulent FMDV wherein said vaccine comprises a FMD leaderless virus having unique restriction endonuclease sites to facilitate the replacement of the capsid region.

A further object of the invention is to provide a marker vaccine which allows a serological distinction between vaccinated animals and animals infected with FMDV.

A still further object of the invention is to provide a strategy for making a FMDV-vectored vaccine platform, which method comprises a genetically engineered attenuated FMDV backbone, molecularly marked by insertion of one or more conserved B cell immunodominant epitopes from a virus different from, but related to, FMDV, and further modified by the inclusion of unique restriction endonuclease sites.

Yet another object of the invention is to provide a method for protecting an animal against FMD by administering an effective amount of rationally designed and chemically-inactivated marker FMDV vaccine.

An additional object of the invention is to provide a method for delaying onset or severity of FMD in an animal by administering an effective amount of rationally designed and chemically-inactivated marker FMDV vaccine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 3B shows the plaque phenotypes of $A_{24}WT$ and mutant FMDVs on BHK-21. BHK-$\alpha_v\beta_6$ or LFBK cell monolayers are also shown. FIG. 3C depicts the analysis of the expression of foreign epitope by mutant FMDVs. BHK-21 cells were infected with the parent recombinant virus $A_{24}WT$, $A_{24}WT3D_{YR}$ or $A_{24}LL3D_{YR}$. At 8 hpi, cells were fixed and processed for IHC using MAbs specific for $3D^{pol}$ protein (F19-59, F32-44). As expected, MAb F32-44 reacted only with WT $3D^{pol}$ protein, and the F19-59 MAb recognized an epitope contained on both virus proteins.

FIG. 4 shows the results of a Competitive Enzyme-Linked Immunoabsorbent Assay (cELISA) measuring the differential antibody response in animals infected with $A_{24}WT$ and $A_{24}WT3D_{YR}$ using MAb F32-44 which specifically binds to an epitope of $3D^{pol}$. Each group shows the average ±1 SD of 2-3 cows infected with either virus. Samples were collected before inoculation and at necropsy. Normal bovine serum (NBS) was used as negative control (no inhibition). #DPI: days post inoculation. * IDL: intradermolingual.

Figure 5:
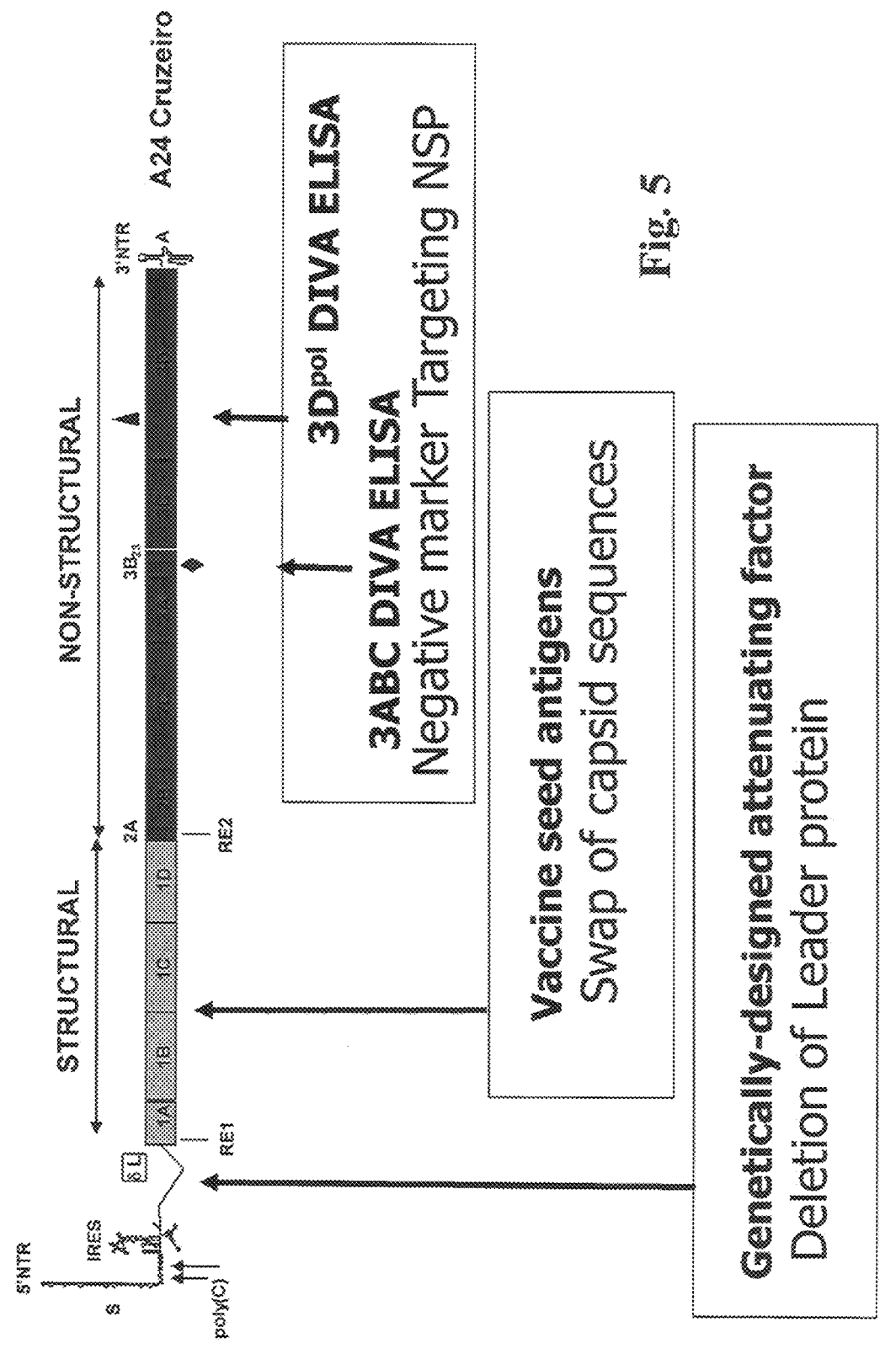

FIG. 5 is a schematic representation of the FMDV genome and features of the marker FMDV vaccine platform.

FIG. 7 shows the results of a Competitive ELISA (cELISA) measuring the differential antibody response in animals infected with $A_{24}WT3B_{PVKV}3D_{YR}$ and $A_{24}LL3B_{PVKV}3D_{YR}$ viruses using MAb F8B which specifically binds to an epitope of 3B. Each graph shows the results of individual cow sera collected at days 0 (before inoculation, no inhibition) and 21 dpi. #DPI: days post inoculation.

FIG. 8B depicts a diagnostic assay for detection of chimera FMDV viruses. $A_{24}WT$, $A_{24}LL$ Asia1-$A_{24}LL3B_{PVKV}3D_{YR}$ and A/Turkey/06-$A_{24}LL3B_{PVKV}3D_{YR}$ viruses were passed in BHK-21 cells four times and viral RNAs were extracted. RT-PCR reactions were performed as outlined in Example 6 using primers to detect presence and/or absence of specific mutations in chimeric viruses.

FIG. 9 shows 48 h single growth curves of $A_{24}WT$ and chimera FMDVs. Cell monolayers were mock- or infected with $A_{24}WT$, $A_{24}LL$ Asia1-$A_{24}LL3B_{PVKV}3D_{YR}$ and A/Turkey/06-$A_{24}LL3B_{PVKV}3D_{YR}$ viruses at a MOI of 5 PFU/cells. Procedures used for viral infection are described in Example 6.

FIG. 10 depicts the analysis of the expression of foreign epitopes by chimera FMDVs. BHK-21 cells were mock- or infected with the parent recombinant virus $A_{24}WT$, $A_{24}LL$ Asia1-$A_{24}LL3B_{PVKV}3D_{YR}$ and A/Turkey/06-$A_{24}LL3B_{PVKV}3D_{YR}$ at a MOI of 5 PFU/cells. At 5 hpi, cell lysates were collected and run under denaturing conditions in a 12% SDS-PAGE gel as described in Example 6. The nitrocellulose blots were probed with MAbs F8B for FMDV 3B protein and F19-6 and F32-44 for FMDV $3D^{pol}$ protein.

DETAILED DESCRIPTION OF THE INVENTION

Figure 1:
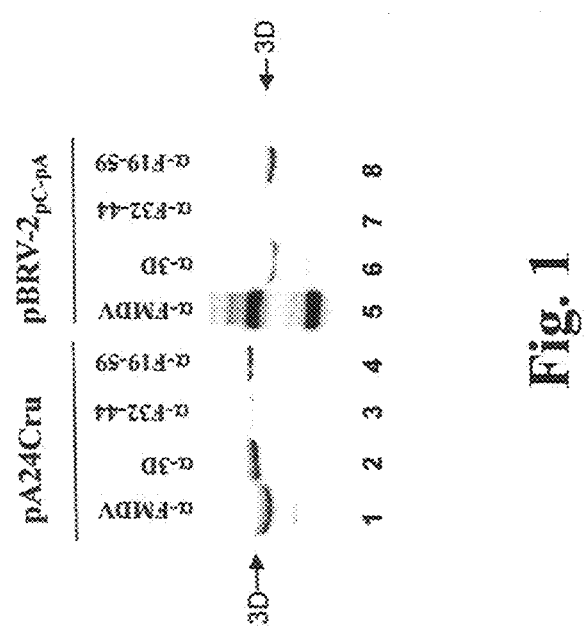
FIG. 1 depicts the polyacrylamide gel electrophoresis (PAGE) of the radioimmunoprecipitation reactions of $^{35}$[S] methionine-labeled FMDV or Bovine Rhinovirus type 2 (BRV2) viral proteins with rabbit antisera or monoclonal antibodies (MAbs) F32-44 or F19-59 raised against FMDV-$3D^{pol}$. The 3D protein was separated by 12% SDS polyacrylamide gel electrophoresis. The gel was fixed, dried, and exposed to X-ray film.

To enable the implementation and successful outcome of FMD control and eradication campaigns, new vaccines should ideally possess a product profile with several key attributes: (1) confers rapid (<7 days) protection against generalized disease following single dose immunization, (2) prevents viral shed, disease transmission and carrier state following direct contact exposure, (3) provides at least 12 months protective immunity following a 2-dose regimen, (4) maintains thermostability for at least 3 months in the cold liquid state, (5) provides broad intra-serotype protection, (6) provides a manufacturing process that eliminates the need for high containment facilities, and (7) contains a negative marker that is DIVA compatible.

This study describes the experimental development of a marker FMDV vaccine production platform candidate, which creates new potentialities for the control of FMD. The negative antigenic marker viruses $A_{24}LL3D_{YR}$ and $A_{24}LL3B_{PVKV}3D_{YR}$ derived by infectious cDNA technology, lack the region coding for $L^{x0}$ and contains a replacement of an immunodominant epitope in 3B and $3D^{pol}$ by the corresponding sequence of bovine rhinovirus that serves as negative antigenic epitope in these proteins. Aerosol inoculation of the live virus in cattle show limited growth and absence of FMD signs in the inoculated animals and no transmission to naïve animals in direct contact. Moreover, the animals did not shed significant amount of virus to the environment. Likewise, swine inoculated in the heal-bulb with $A_{24}LL3D_{YR}$ virus, showed no clinical signs of FMD. Furthermore, the inoculated animal did not transmit the disease to contact animals. The $A_{24}LL3D_{YR}$ vaccine candidate used to produce inactivated antigen by chemical binary ethylenimine (BEI) inactivation proved to be as effective as a commercially available inactivated antigen FMDV vaccine in protecting cattle and swine from challenge with the parental FMD virus.

Picornaviruses contain a positive sense single-strand RNA genome that encodes a single polyprotein that is processed to produce both non-structural (NSP, replicating) and structural (SP, capsid) proteins. In FMD control and livestock surveillance programs, the use of expressed recombinant NSP products (baculovirus, E. coli) coupled with diagnostic assays such as ELISA (competitive, indirect) enzyme-linked immuno-electrotransfer blot (EITB), VIAA have been extensively exploited to allow discrimination between animals which have been vaccinated against FMD from those that have recovered from infection (Fernándes et al. 1990. Prev. Vet. Med. 9:233-240; Bergmann et al. 2000. Arch. Virol. 145: 473-489; Brocchi et al. 2006. Vaccine 24:6966-6979; Clavijo et al. 2004. J. Virol. Methods 120:217-227; Dekker et al. 2008. Vaccine 26:2723-2732; McVicar and Sutmoller, supra; Sorensen et al. 2005. Arch. Virol. 150:805-814; Sorensen et al. 1998, supra; Yang et al. 2007b. Vet. Immunol. Immunopathol. 115:126-134). Vaccinated animals that are exposed to virus might be infected without clinical manifestations of FMD and subsequently become chronic carriers representing potential sources for new outbreaks of the disease. Therefore, there is a need to develop more effective vaccines that block virus infection and that do not induce antibodies against some of the immunogenic non-structural viral proteins produced during FMDV replication in the host in order to differentiate the response of naturally infected animals from vaccinated animals.

In this study we present an approach to rationally design novel negative marker FMDV vaccine viruses. The vaccine candidate viruses $A_{24}LL3D_{YR}$ and $A_{24}LL3B_{PVKV}3D_{YR}$ harbor negative antigenic markers for potential DIVA capabilities, encoded in either the $3D^{pol}$ alone or 3B and $3D^{pol}$ combined, respectively. Additional modification of the vaccine virus consisted of the deletion of the non-essential $L^{pro}$ coding sequence that rendered these viruses attenuated in vivo. Therefore, it could reduce the risk for escape of virulent FMDV during large scale during vaccine production. The vaccine platform also includes strategically-located restriction-enzyme sites that allow easy swapping of the relevant antigenic region for different serotypes and subtypes.

Comparison of the $3D^{pol}$ sequence for FMDV and BRV-2 viruses revealed 64% identity (Hollister et al. 2008. *Virology* 373:411-425) at the amino acid level. Amino acids 16-32 comprise an important antigenic site in the FMDV $3D^{pol}$ protein (Yang et al. 2007a. *J. Immunol. Methods* 321:174-181) and this peptide is 76% identical among these closely-related viruses. MAb F32-44, which was raised against native FMDV $3D^{pol}$ and specifically binds an epitope of FMDV $3D^{pol}$, and MAb F8B, which was raised against FMDV 3B protein and specifically binds an epitope of FMDV 3B, each showed high reactivity against $A_{24}$WT protein. However, MAb F32-44 and MAb F8B did not react with the BRV2 $3D^{pol}$ or the mutant $A_{24}LL3D_{YR}$, and $A_{24}LL3B_{PVKV}3D_{YR}$ viral counterparts, i.e., these antibodies did not specifically bind to epitopes of BRV2 $3D^{pol}$ or BRV2 3B or mutant counterparts of $3D^{pol}$ or 3B, suggesting that these antigenic markers might be of significant value as a DIVA diagnostic tool.

Mutations introduced in the coding regions for 3B and $3D^{pol}$ using the $pA_{24}Cru$ full-length plasmid produced viruses ($A_{24}WT3B_{PVKV}3D_{YR}$) that did not react with MAbs F32-44 and F8B but showed similar plaque phenotypes and tissue culture propagation properties as the parental $A_{24}WT$ virus. Moreover studies in cattle and swine demonstrated that $A_{24}WT3D_{YR}$ and $A_{24}WT3B_{PVKV}3D_{YR}$ mutants are highly pathogenic and able to spread the disease to contact animals as the $A_{24}WT$, further suggesting that the introduced mutation themselves, did not significantly affect virulence. The mutations introduced into the 3B and $3D^{pol}$ appeared to be stable not only in tissue culture (unchanged even after 15 serial passage sin BHK-21) but also in animals.

Reduced virulence is a critical aspect to be addressed in developing a safe vaccine to be produced in an area free of the disease. Attenuation of the double negative marker virus was achieved by manipulating the genome to eliminate the $L^{pro}$ coding sequence, which is known to be involved in FMDV pathogenesis in vivo (see the Introduction). Here ($A_{24}LL$, $A_{24}LL3D_{YR}$, $A_{24}LL3B_{PVKV}3D_{YR}$) and in previous studies ($A_{12}LLV2$), it has been shown that deletion of the FMDV leader proteinase coding sequence created viruses that maintained the ability to infect BHK-21 cells but display low virulence for cattle or pigs (Almeida et al. 1998. *Virus Res.* 55:49-60; Brown et al., supra; Chinsangaram et al., supra; Mason et al. 1997, supra). Animals infected with $A_{24}LL3D_{YR}$ by the aerosol route (cattle) or by direct inoculation of $A_{24}LL3D_{YR}$, $A_{24}LL3B_{PVKV}3D_{YR}$, A-Turkey/06-$A_{24}LL3B_{PVKV}3D_{YR}$ or Asia 1-$A_{24}LL3B_{PVKV}3D_{YR}$ viruses in the feet (swine) demonstrated that the prototype virus candidates are highly attenuated for clinical disease and unable to spread virus to contact animals on both susceptible livestock models. Thus, given the reduced replication of $A_{24}LL3D_{YR}$ and $A_{24}LL3B_{PVKV}3D_{YR}$ as well as with chimeric A-Turkey/06-$A_{24}LL3B_{PVKV}3D_{YR}$ or Asia 1-$A_{24}LL3B_{PVKV}3D_{YR}$ viruses in the natural host and the lack of transmission to in-contact animals, it would appear highly unlikely that virus transmission that leads to clinical disease could occur under field conditions as a results of incomplete inactivation of this marker vaccine or due to virus leaking from the manufacturing laboratory.

Figure 4:
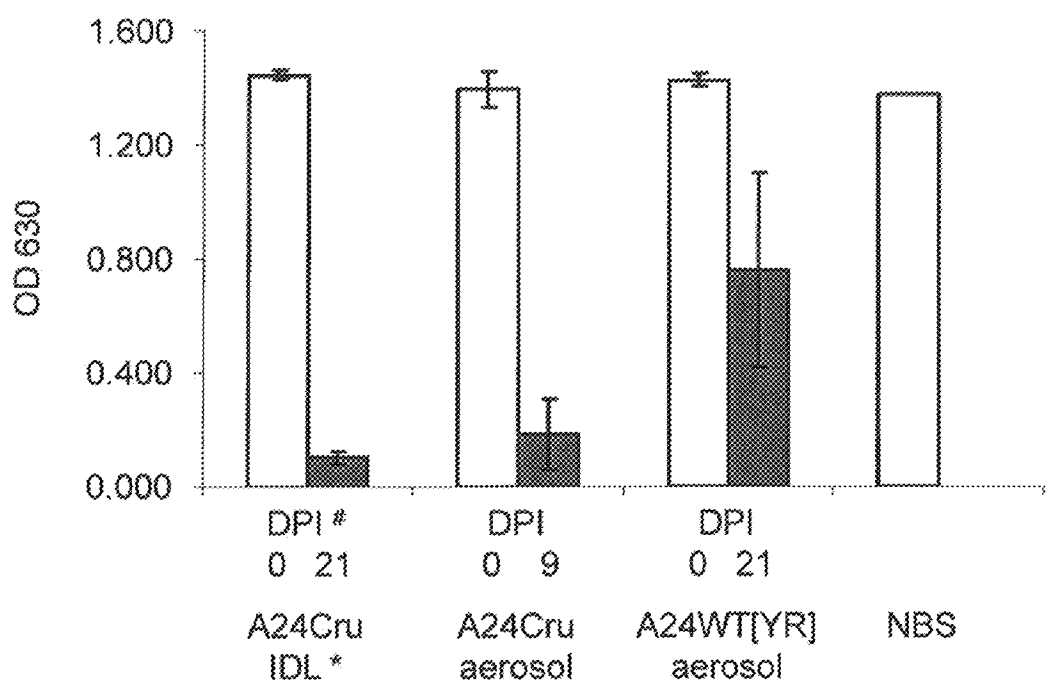

Animals infected with the single and double marker FMDV produced in the backbone of a leader-containing genome ($A_{24}WT3D_{YR}$ and $A_{24}WT3B_{PVKV}3D_{YR}$) developed a serological antibody response that, when analyzed at 21 dpi, allow a differentiation relative to the serologic profile observed for wild-type infected animals. This is particularly important since the FMDV $3D^{pol}$ protein is known to stimulate a strong humoral and cellular immune response in the host at early times (Collen et al. 1998. *Virus Res.* 56:125-133; Cowan and Graves, supra). In the cELISA utilized in this study, the $3D^{pol}$ antigen is captured to the solid phase, then, the ability of test sera to inhibit the binding of the MAb F32-44 to the antigen is evaluated. The procedure, originally developed by Yang et al. (2007a, supra) is used for the detection of antibodies against different serotypes of FMDV. Likewise, an in house cELISA based on competition with MAb F8B (raised against 3B protein) was used to detect serological responses to the epitope contained in the 3B viral protein. Because mutant $A_{24}LL3D_{YR}$ and $A_{24}LL3B_{PVKV}3D_{YR}$ viruses lack epitopes that are present in the parental virus (on the basis of which cELISA were established; for $3D^{pol}$, see FIG. 4 and for 3B, see FIG. 7), our work provides a potential DIVA companion test to be used in conjunction with these marker FMDV vaccine candidates. Our data support the importance of the antigenic site contained in the FMDV $3D^{pol}/16$-32 peptide and demonstrate that this immunodominant epitope was effectively removed in the mutant viruses.

Killed-FMDV vaccines are presently commercially available and have been shown to be safe and effective for the control of FMD. The killed-virus vaccine is prepared from virus grown in BHK-21 cells, is chemically-inactivated (BEI), and adjuvant is added to the viral product. We have demonstrated that the BEI-inactivated marker $A_{24}LL3D_{YR}$ vaccine elicited an immune response that completely protected cattle from clinical disease after direct inoculation. These results are similar to those observed when animals were immunized with a commercial polyvalent FMD vaccine with a standard antigen payload. The high level of protection against live virus challenge was achieved in animals that received one dose of either the experimental or commercial vaccines. The analysis of the humoral response against FMDV revealed that both vaccine formulations were able to induce detectable levels of neutralizing antibodies before challenge. Although we did not detect a significant antibody response against NSPs after single dose of vaccination (data not shown), animals infected with the $A_{24}WT3D_{YR}$ virus developed good antibody responses to NSPs lacking recognition to the marker epitope (see FIG. 4). In the field practice, multiple doses of inactivated FMDV vaccines are applied for the control and prevention of FMD, and under this regimen, antibodies against $3D^{pol}$ are commonly detected (Silberstein et al. 1997. *Arch. Virol.* 142:795-805). Since the target epitopes are absent from the $A_{24}LL3B_{PVKV}3D_{YR}$ platform, antibodies against these epitopes will not develop in vaccinated animals despite multiple immunizations (every 6 months), a common field practice. Therefore, this strategy will be feasible in the field practice. In addition to the above demonstrated characteristics that are desirable for any vaccine candidate, the $A_{24}LL3D_{YR}$ and $A_{24}LL3B_{PVKV}3D_{YR}$ marker viruses were also shown to be attenuated in the natural host, but they grow well in BHK-21 cells. This virus property offers the advantage to reduce the risk of outbreaks originated by escape of highly virulent FMDVs from vaccine manufacturing facilities, where high load of viruses are handled. In addition to the distinctive serological profile elicited by the marker viruses, the mutant viruses can be differentiated from field FMDVs by genetic methods.

Considering the high economic damage that FMD can elicit on livestock (see review by Sutmoller and Olascoaga (Sutmoller et al. 2003, supra), current vaccination programs are now supporting the "vaccinate-to-live" policy for FMD outbreaks. In this scenario, the rational design of negative marker ($A_{24}LL3D_{YR}$, and $A_{24}LL3B_{PVKV}3D_{YR}$ or chimeric viruses such as A-Turkey/06-$A_{24}LL3B_{PVKV}3D_{YR}$ or Asia1-$A_{24}LL3B_{PVKV}3D_{YR}$) vaccine candidates, capable to elicit an antibody response that can be differentiated from the response induced by the wild-type virus, and used in conjunction with a companion DIVA test (cELISA), could assist in FMD control measurements and support the differentiation of infected versus vaccinated animals.

Production and manipulation of the isolated polynucleotide molecules described herein are within the skill in the art and can be carried out according to recombinant techniques described, among other places, in Sambrook et al. 1989. *Molecular Cloning: A Laboratory Manual*, 2d ed., Cold Spring Harbor Laboratory Press, Cold Spring Harbor, N.Y. and Innis et al. (eds). 1995. *PCR Strategies*, Academic Press, Inc., San Diego, which are incorporated herein by reference.

The subject invention provides vectors comprising genetically modified nucleic acid sequences that encode genetically modified infectious RNA molecules that encode genetically modified Foot and Mouth Disease Viruses.

In particular, the subject invention provides isolated polynucleotide molecules encoding genetically modified infectious RNA molecules that encode genetically modified FMD viruses; namely, the vaccine candidate viruses $A_{24}LL3D_{YR}$, and $A_{24}LL3B_{PVKV}3D_{YR}$ which harbor negative antigenic markers for potential DIVA capabilities, encoded in either the $3D^{pol}$ alone or 3B and $3D^{pol}$ combined, respectively.

It is understood that terms herein referring to nucleic acid molecules such as "isolated polynucleotide molecule" and "nucleotide sequence include both DNA and RNA molecules and include both single-stranded and double-stranded molecules whether it is natural or synthetic origin.

For example, SEQ ID NO:1 is a DNA sequence corresponding to the genetically modified RNA genome of a genetically modified FMDV. Thus, a DNA sequence complementary to the DNA sequence set forth in SEQ ID NO:1 is a template for, i.e. is complementary to or "encodes", the RNA genome of the FMDV virus (i.e., RNA that encodes the FMDV).

Furthermore, when reference is made herein to sequences homologous to a sequence in the Sequence Listing, it is to be understood that sequences are homologous to a sequence corresponding to the sequence in the Sequence Listing and to a sequence complementary to the sequence in the Sequence Listing.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, two nucleotide (RNA or DNA) sequences are substantially homologous when at least 80% (preferably at least 85% and most preferably 90%) of the nucleotides match over the defined length of the sequence using algorithms such as CLUSTRAL or PHILIP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by DNA-DNA, DNA-RNA, or RNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a modified FMDV, i.e., $A_{24}LL3D_{YR}$ (SEQ ID NO:1) and/or $A_{24}LL3B_{PVKV}3D_{YR}$ (SEQ ID NO:3), and which hybridize under stringent conditions, as described herein, to the modified FMDVs, the $A_{24}LL3D_{YR}$ and $A_{24}LL3B_{PVKV}3D_{YR}$ sequences disclosed herein, i.e., SEQ ID NO:1, SEQ ID NO:3, or to fragments thereof, are encompassed by the present invention. Fragments of a nucleotide sequences that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the $A_{24}LL3D_{YR}$ and $A_{24}LL3B_{PVKV}3D_{YR}$ sequences, the amino acid sequences of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, a modified $A_{24}LL3D_{YR}$ and/or $A_{24}LL3B_{PVKV}3D_{YR}$ activity. Such variants may result from, for example, genetic polymorphism or from human manipulation. Biologically active variants of modified $A_{24}LL3D_{YR}$ and $A_{24}LL3B_{PVKV}3D_{YR}$ activities of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified FMDV $A_{24}LL3D_{YR}$ and/or $A_{24}LL3B_{PVKV}3D_{YR}$ activities. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of modified FMDV $A_{24}LL3D_{YR}$ and/or $A_{24}LL3B_{PVKV}3D_{YR}$ can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "FMD" encompasses disease symptoms in cattle and swine caused by a FMDV infection. Examples of such symptoms include, but are not limited to, vesicles in the mouth, and on the feet. As used herein, a FMDV that is "unable to produce FMD" refers to a virus that can infect a pig, but which does not produce any disease symptoms normally associated with a FMD infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The terms "foot and mouth disease virus" and "FMDV", as used herein, unless otherwise indicated, mean any strain of FMD viruses.

The term "open reading frame", or "ORF", as used herein, means the minimal nucleotide sequence required to encode a particular FMDV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly bovine and porcine cells, and are described in further detail below.

A "functional virion" is a virus particle that is able to enter a cell capable of hosting a FMDV, and express genes of its particular RNA genome (either an unmodified genome or a genetically modified genome as described herein) within the cell. Cells capable of hosting a FMDV include baby hamster kidney, strain 21, cells (BHK-21) and BHK-$\alpha_v\beta_6$ cells expressing bovine $\alpha_v\beta_6$ integrin. Other mammalian cells, especially other bovine and porcine cells, may also serve as suitable host cells for FMDV virions.

The isolated polynucleotide molecules of the present invention encode FMD viruses that can be used to prepare live attenuated vaccines using art-recognized methods for protecting cattle and swine from infection by a FMDV, as described in further detail below. Furthermore, these isolated polynucleotide molecules are useful because they can be mutated using molecular biology techniques to encode genetically-modified FMD viruses useful, inter alia, as vaccines for protecting cattle and swine from FMD infection. Such genetically-modified FMD viruses, as well as vaccines comprising them, are described in further detail below.

Accordingly, the subject invention further provides a method for making a genetically modified FMDV, which method comprises mutating the DNA sequence encoding an infectious RNA molecule which encodes the FMDV as described above, and expressing the genetically modified FMDV using a suitable expression system. A FMDV, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art.

The subject invention further provides an isolated polynucleotide molecule comprising a DNA sequence encoding an infectious RNA molecule which encodes a genetically modified FMDV that is unable to produce FMD in cattle and/or swine, wherein the DNA sequence encoding the infectious RNA molecule encoding said modified FMDV $A_{24}LL3D_{YR}$ comprises SEQ ID NO:1, said modified FMDV $A_{24}LL3B_{PVKV}3D_{YR}$ comprises SEQ ID NO:3 or sequences homologous thereto, contain one or more mutations that genetically disable the encoded FMDV in its ability to produce FMD. "Genetically disabled" means that the FMDV is unable to produce FMD in a bovine or swine animal infected therewith.

In one embodiment, the genetically modified FMDV disabled in its ability to cause FMD is able to elicit an effective immunoprotective response against infection by FMDV in cattle or swine. Accordingly, the subject invention also provides an isolated polynucleotide molecule comprising a DNA sequence encoding an infectious RNA molecule which encodes a FMDV that is genetically modified such that when it infects cattle and/or swine it: a) is unable to produce FMD in the animal, and b) is able to elicit an effective immunoprotective response against infection by a FMDV in the animal, wherein the DNA sequence encoding said modified FMDV $A_{24}LL3D_{YR}$ comprises SEQ ID NO:1, said modified FMDV $A_{24}LL3B_{PVKV}3D_{YR}$ comprises SEQ ID NO:3, or sequences homologous thereto, contain one or more mutations that genetically disable the encoded FMDV in its ability to produce FMD.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

The genetically modified FMD viruses encoded by the above-described isolated polynucleotide molecules are, in one embodiment, able to elicit an effective immunoprotective response against infection by a FMDV. Such genetically modified FMD viruses are preferably able to elicit an effective immunoprotective response against any strain of FMD viruses.

In one embodiment, the mutation or mutations in the isolated polynucleotide molecule encoding the genetically disabled FMDV are non-silent and occur in one or more open reading frames of the nucleotide sequence encoding the FMDV.

As used herein, unless otherwise indicated, "coding regions" refer to those sequences of RNA from which FMDV proteins are expressed, and also refer to cDNA that encodes such RNA sequences. Likewise, "ORFs" refer both to RNA sequences that encode FMDV proteins and to cDNA sequences encoding such RNA sequences.

Determining suitable locations for a mutation or mutations that will encode a FMDV that is genetically disabled so that it is unable to produce FMD yet remains able to elicit an effective immunoprotective response against infection by a FMDV and which can differentiate a naturally infected animal from a vaccinated animal can be made based on SEQ ID NO:1 and/or SEQ ID NO:3 provided herein. One of ordinary skill can refer to the sequence of the infectious cDNA clone of FMDV provided by this invention, make sequence changes which will result in a mutation altering the leader sequence as well as sequences within $3D^{pol}$ and 3B, and test the viruses encoded thereby for their abilities to produce FMD in swine, to elicit an effective immunoprotective response against infection by a FMDV, and to make possible the differentiation of infected vs. vaccinated animals. In so doing, one of ordinary skill can refer to techniques known in the art and also those described and/or exemplified herein.

For example, an ORF of the sequence encoding the infectious RNA molecule encoding the FMDV can be mutated and the resulting genetically modified FMDV tested for its ability to cause FMD.

In a further preferred embodiment, an antigenic epitope of the genetically modified FMDV of the present invention results in a negative marker. Such isolated polynucleotide molecules and the FMD viruses they encode are useful, inter alia, for studying FMD infections in cattle and swine, determining successfully vaccinated cattle and swine, and/or for distinguishing vaccinated cattle and swine from cattle and swine infected by a wild-type FMDV. Preferably, such isolated polynucleotide molecules further contain one or more mutations that genetically disable the encoded FMDV in its ability to produce FMD, and more preferably are able to elicit an effective immunoprotective response in bovine and porcine animals against infection by a FMDV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified FMDV that detectably lacks FMDV antigenic epitope, wherein the DNA sequence encoding the RNA molecule encoding the modified FMDV is SEQ ID NO:1, SEQ ID NO:3, or sequences homologous thereto, except that it lacks one or more nucleotide sequences encoding a detectable FMDV antigenic epitope. Such isolated polynucleotide molecules are useful for distinguishing between cattle and/or swine infected with a recombinant FMDV of the present invention and cattle and/or swine infected with a wild-type FMDV. For example, animals vaccinated with killed, live or attenuated FMDV encoded by such an isolated polynucleotide molecule can be distinguished from animals infected with wild-type FMDV based on the absence of antibodies specific to the missing antigenic epitope, or based on the absence of the antigenic epitope itself: If antibodies specific to the missing antigenic epitope, or if the antigenic epitope itself, are detected in the animal, then the animal was exposed to and infected by a wild-type FMDV. Means for detecting antigenic epitopes and antibodies specific thereto are known in the art, as discussed above. Preferably, such an isolated polynucleotide molecule further contains one or more mutations that genetically disable the encoded FMDV in its ability to produce FMD. More preferably, the encoded virus remains able to elicit an effective immunoprotective response against infection by a FMDV.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween® 80 detergent, 2.5% (v/v) ethanol, 100 µl/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including Domb et al. 1992. *Polymers for Advanced Technologies* 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences, Vol.* 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 g to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

In summary, our studies provide a recombinant viral-vectored vaccine platform comprising a genetically modified FMDV comprising deletion of the $L^{pro}$ coding sequence, mutations (negative markers) introduced in two non-structural viral proteins resulting in the elimination of two antigenic epitopes recognized by specific antibodies, one located in 3B and the other in 3D, thus providing targets for DIVA (Differentiation of naturally Infected from Vaccinated Animals) serological tests, and inclusion of unique restriction endonuclease sites to facilitate the replacement of the capsid region; and the genetically modified FMDV has been chemically-inactivated. The rationally designed attenuated FMDV vaccine production platform can be used to manufacture inactivated antigen vaccine that is effective to protect an animal from clinical FMD when challenged with virulent FMDV and is a marker vaccine which allows a serological distinction between vaccinated animals and animals infected with FMDV.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

FMDV type $A_{24}$ Cruzeiro was derived from the infectious cDNA clone $pA_{24}$Cru (called here for simplicity $A_{24}$WT, (Rieder et al. 2005. *J. Virol.* 79:12989-12998). A plasmid containing the bovine rhinovirus type 2 (pBRV2, accession number EU236594) sequence from poly[C] to poly[A] described previously (Hollister et al., supra) was used as a source of bovine rhinovirus genetic material. Baby hamster kidney strain 21, clone 13, cell line (BHK-21) was maintained in Eagle's basal medium (BME) (Life Technologies, Gaithersburg, Md.) supplemented with 10% bovine calf serum (BCS) (Hyclone, South Logan, Utah), 10% Tryptose phosphate broth, and antibiotic/antimycotic. Monolayers of a continuous bovine kidney cell line (LFBK, (Swaney, L. M. 1988. *Vet. Microbiol.* 18:1-14) were grown in Eagle's minimal essential medium (MEM) containing 10% fetal calf serum (Hyclone, South Logan, Utah) and antibiotic/antimycotic. Swine kidney cells (de Castro, M. P. 1964. *Arq. Inst. Biol.* (Sao Paulo) 31:63-78.) were propagated in Dulbecco's modified Eagle's medium (D-MEM) supplemented with 10% FBS and antibiotic/antimycotic. BHK-$\alpha_v\beta_6$ is a stable cell line expressing the bovine $\alpha_v\beta_6$ integrin, propagated in BME containing 10% bovine calf serum (Hyclone, South Logan, Utah), with the addition of G418 and Zeocin (Invitrogen), and has been previously described (Duque et al. 2004. *J. Virol.* 78:9773-9781). Cells were grown at 37° C. in a humidified with 5% $CO_2$ atmosphere.

Example 2

Non-structural Protein $3D^{pol}$: Immunohistochemistry and Radioimmunoprecipitation Assays Our previous studies have identified several invariant amino acids in the $3D^{pol}$ protein of the closely-related FMDV and BRV2 $3D^{pol}$ viruses (Hollister et al., supra). To further determine if these sequence similarities result in the display of similar (shared) epitopes between the corresponding $3D^{pol}$ of these viruses, we carried out a radioimmuoprecipitation (RIP) assay using specific polyclonal or monoclonal antibodies (MAb) specific for FMDV $3D^{pol}$. To this end, FMDV or BRV2 transcript RNAs derived from $pA_{24}$Cru and pBRV2 were translated in vitro in the presence of $^{35}$S-methonine and then the extracts were subjected to RIP using FMDV-specific anti-$3D^{pol}$ rabbit polyclonal sera or the MAbs F19-59 and F32-44 directed against the FMDV non-structural protein $3D^{pol}$ and partially characterized by Yang et al. (2007a, supra).

Cell monolayers grown in 6-well plates were infected with virus at an MOI=1 and 6 h later the infected cells were fixed with cold acetone:methanol (50/50) mix for 20 min followed by two washes with PBS. Fixed cells were immunoperoxidase-stained using FMDV-specific MAb following the manufacturer's instructions of the Vectastain ABC Alkaline Phosphatase Kit from Vector labs. Reactivity of antibodies to $3D^{pol}$ was also measured using radioimmunoprecipitation (RIP) assays performed as described by Rieder et al. (1994. *J. Virol.* 68:7092-7098).

As shown in FIG. 1, SDS-PAGE analysis of the radioimmunoprecipitates revealed a strong reaction for MAb F19-59 and the anti $3D^{pol}$ rabbit polyclonal sera with both sources (FMDV and BRV2) of viral $3D^{pol}$ proteins. In contrast, MAb F32-44 reacted only with FMDV $3D^{pol}$ and in repeated RIPs attempts it failed to recognize the BRV-2 protein (FIG. 1). These results indicate that BRV2 $3D^{pol}$ lacks the epitope found on the FMDV $3D^{pol}$ protein that is recognized by MAb F32-44.

Example 3

Derivation of $A_{24}$LL Negative Marker FMDV Viruses

Figure 2:
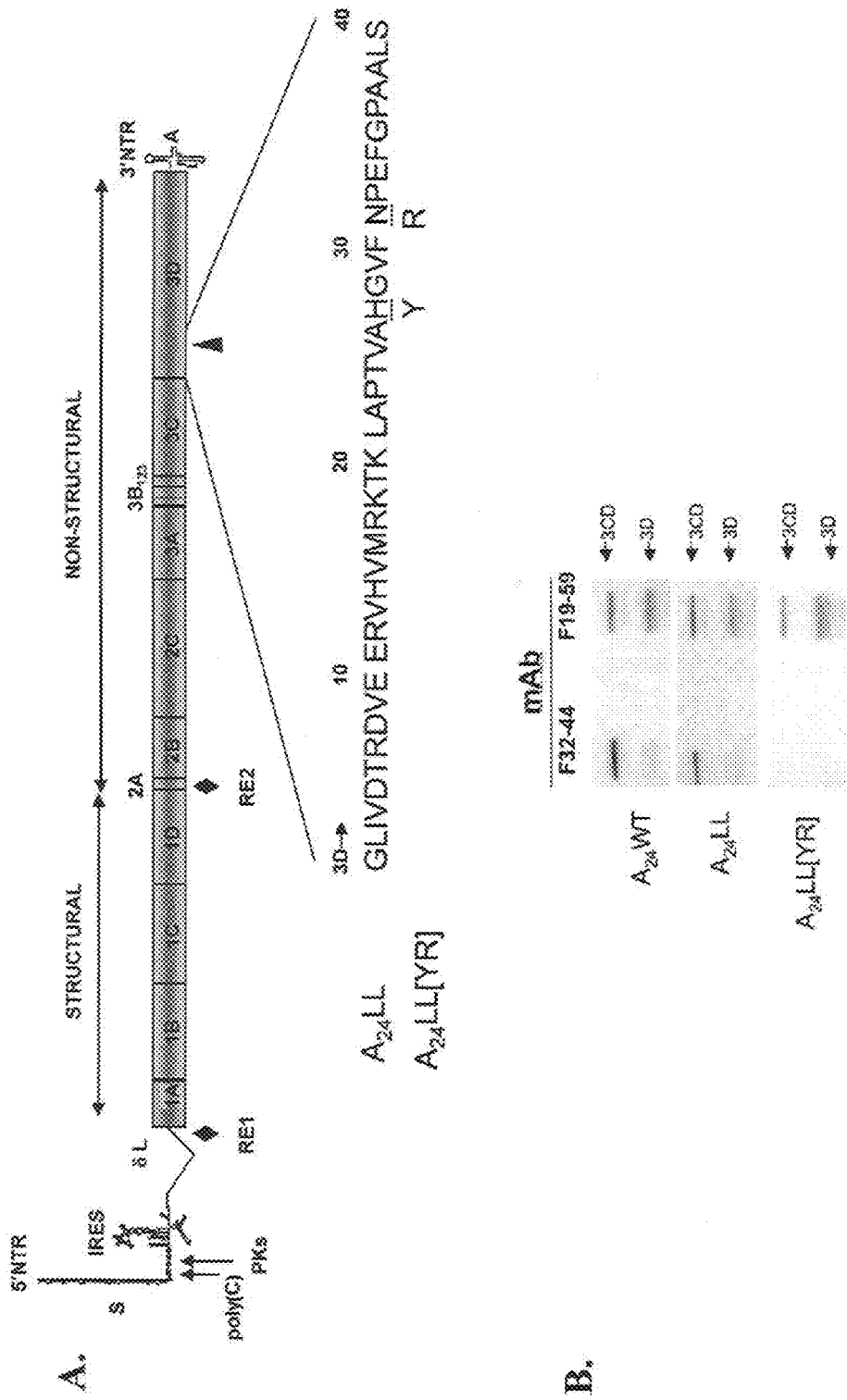
FIG. 2A depicts a schematic representation of the FMDV genome and relative locations of the modifications introduced in the viruses used in this study. $A_{24}LL3D_{YR}$ virus was generated by site directed mutagenesis of a full-length clone $pA_{24}Cru$ of the FMDV outbreak strain $A_{24}$ Cruzeiro. Additional modifications introduced in the mutant plasmid included: δL: deletion of the leader gene; underlined are two amino acid substitutions at position $H_{27}Y$ and $N_{31}R$ of the FMDV $3D^{pol}$ ($A_{24}LL$ sequence comprising $H_{27}$ and $N_{31}$ [SEQ ID NO:5]; $A_{24}LL[YR]$ mutant sequence comprising $Y_{27}$ and $R_{31}$ [SEQ ID NO:6]; two unique restriction endonuclease enzyme cloning sites 1 and 2 (♦, RE1, RE2); Deleted antigenic determinant in the genome (3DYR; Δ).
FIG. 2B depicts the radioimmuno-precipitation of $^{35}$S-radiolabled viral $3D^{pol}$ protein with selected MAbs. Extracts were prepared from cell lysates obtained from BHK-21 cells infected or not with $A_{24}WT$, $A_{24}LL$ or $A_{24}LL3D_{YR}$ viruses at a MOI of 5 PFU/cell. The cell extracts were run under denaturing conditions in a 12% SDS-PAGE gel as described in Example 4. The nitrocellulose blots were probed with MAb F19-59 and F32-44 for FMDV $3D^{pol}$ protein.

Two mutant plasmids designated $pA_{24}WT3D_{YR}$ and $pA_{24}LL3D_{YR}$ were derived by site-directed mutagenesis using either full-length infectious clone of FMDV $pA_{24}$Cru (Rieder et al. 2005, supra) or the backbone of the leader-deleted $pA_{24}$LL infectious cDNA clones. Plasmids p $A_{24}WT3D_{YR}$ and $pA_{24}LL3D_{YR}$ were engineered with a substitution in $3D^{pol}$ found in BRV2 at the respective locations that would eliminates an important antigenic epitope in $3D^{pol}$; $His_{27}$ was replaced by Tyr ($H_{27}>Y$) and $Asn_{31}$ was changed to the basic amino acid Arg ($N_{31}>R$) (FIG. 2). Thus, both $A_{24}WT3D_{YR}$ and $A_{24}LL3D_{YR}$ have the $His_{27}$ and $Asn_{31}$ of the WT FMDV replaced by the BRV2 amino acids Tyr and Arg, respectively. The $3D^{pol}$ antigen of WT FMDV has the amino acid sequence of SEQ ID NO:5; the mutant $3D^{pol}$ comprising the substitution of the BRV2 amino acids has the amino acid sequence of SEQ ID NO:6 and is found in $A_{24}WT3D_{YR}$ and $A_{24}LL3D_{YR}$ viruses. Infectious RNA were in vitro transcribed from infectious cDNA clones and virus rescued from BHK-21 transfected cells confirmed that only the mutation at the 3D$^{pol}$ locus encoding the YR epitope was present in the mutant viruses.

The 3D$^{pol}$ region of pA$_{24}$Cru (A$_{24}$WT) was modified by PCR utilizing mutagenic oligonucleotides P1266 (5'-AC-CGTTGCGTACGGTGTGTTCCGTCCTGAGTTCGGG; SEQ ID NO:7) and P1267 (5' CCCGAACTCAGGACG-GAACACACCGTACGCAAC GGT; SEQ ID NO:8) engineered to introduce mutations at codons 27 and 31 of protein 3D$^{pol}$ (see FIG. 2). Deletion of Leader gene and introduction of FseI at the beginning of the coding region for the capsid viral protein VP4 and NheI site in 2A were generated by overlap PCR fusion, created by mixing PCR-amplified fragments, re-amplifying through the product of the fusion of these two fragments. This was accomplished by using oligonucleotide P819 (5'-CGAGCCACAGGAAGGATGGG GGCCGGCCAATCCAG; SEQ ID NO:9) P820 (5'-CTG-GATTGGCCGGCCCCCATCCTTCCTGTGGCTCG; SEQ ID NO:10) containing an FseI site added by silent mutation in VP4 and P/2A-NheI(s) (GACCTGCTTAA GCTAGCCGGAGACGTTGA; SEQ ID NO:11) and P/2A-NheI(a) (5'TCAACGTCTCCGGCTAGCTTAAGCAGGTC; SEQ ID NO:12) containing a silent mutation that introduces NheI in the coding region for 2A. The generated plasmids pA$_{24}$Cru, pA$_{24}$WT3D$_{YR}$, pA$_{24}$LL3D$_{YR}$ and pA$_{24}$LL all contain a T7 promoter sequence in front of a hammerhead ribozyme at the 5' terminus of the S fragment of the FMDV genome, and terminates with a poly(A) tract of 15 residues and they possess a unique restriction site (SwaI) used for linearization.

Figure 6:
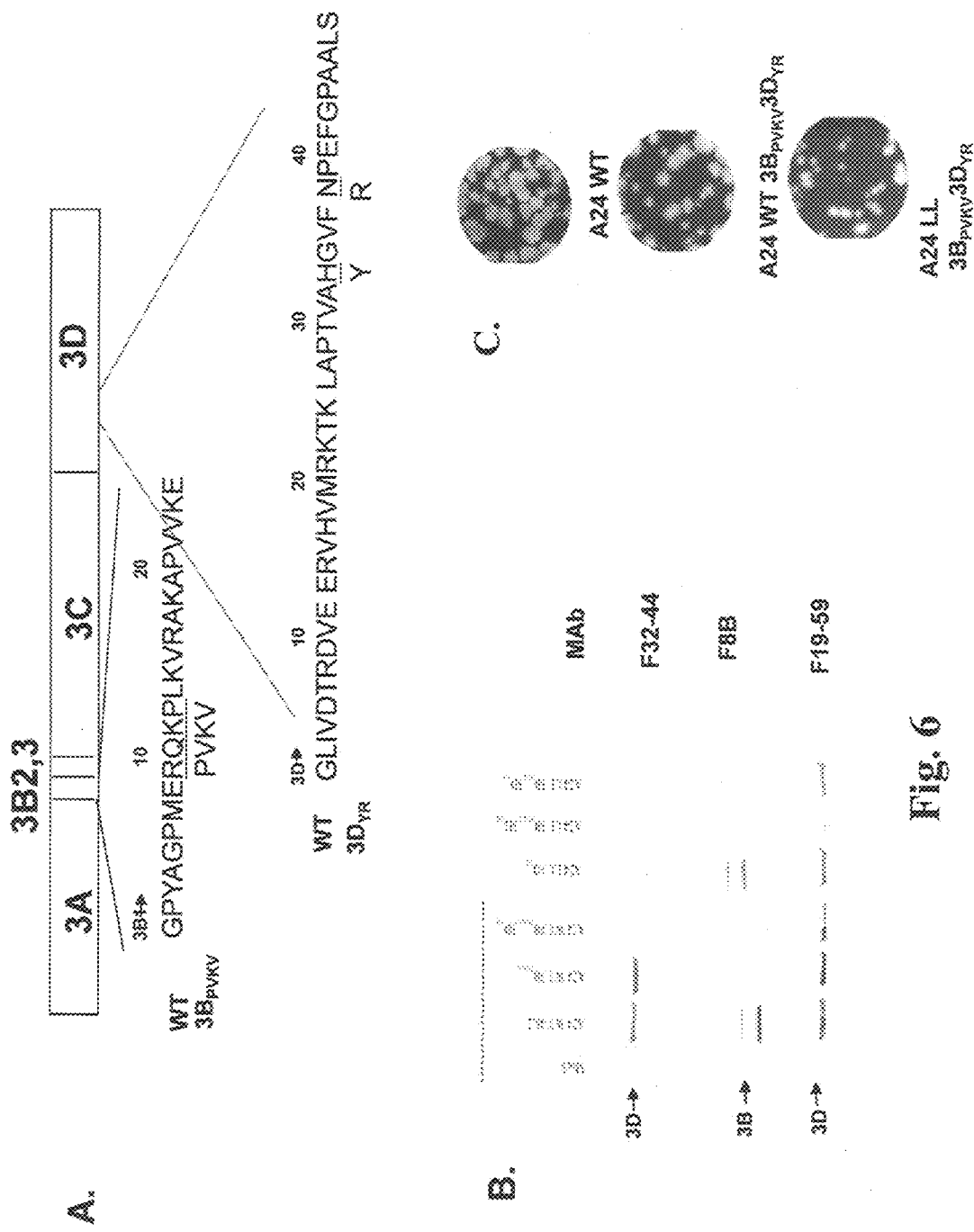
FIG. 6A is a schematic representation of the double negative marker FMD viruses (top panel). The FMDV MAb F8B epitope in 3B and MAb F32-44-epitope in 3D pol are shown along with their modified versions where the MAb reactivities were abolished in the mutant viruses: (wild-type [WT] 3B sequence comprising $R_9Q_{10}K_{11}P_{12}$ [SEQ ID NO:15]; $3B_{PVKV}$ sequence comprising $P_9V_{10}K_{11}V_{12}$ [SEQ ID NO:16]) and WT $3D^{pol}$ comprising $H_{27}$ and $N_{31}$[SEQ ID NO:5]; mutant $3D_{YR}$ sequence comprising $Y_{27}$ and $R_{31}$ [SEQ ID NO:6]).
FIG. 6B depicts the antigenic phenotype of marker FMDVs compared to the parental virus using Western blot analyses.
FIG. 6C shows plaque phenotypes of the double negative antigen mutant viruses in the wild-type and LL backbones in comparison to the WT virus.

A double negative epitope A$_{24}$WT3B$_{PVKV}$3D$_{YR}$ and A$_{24}$LL3B$_{PVKV}$3D$_{YR}$ mutant FMDVs were derived from plasmids pA$_{24}$WT3D$_{YR}$, pA$_{24}$LL3D$_{YR}$ respectively, lacking one of their 3B (3B$_1$ or also known as VPg$_1$) proteins, and containing a substitution in 3B$_2$ that abolished reactivity with MAb F8B (a gift from Alfonso Clavijo, National Centre for Foreign Animal Disease, Winnipeg, Manitoba, Canada). To derive these mutant plasmids, a PCR product spanning sequences between the unique restriction sites SalI and AgeI were produced lacking 3B$_1$ and harboring a substitution of 3B$_2$ sequence RQKP at amino acids 9-12 by PVKV found at similar position in bovine rhinitis-2. The cDNA template for PCR corresponded to a 3B$_1$ deleted mutant virus A$_{24}$WT-5853 that arose from transfection of a RNA that contained a transposon insertion in 3B$_1$ at position 5853 (Pacheco et al., supra). This virus has shown to grow in vitro and produce signs of FMD in cattle similar to WT A$_{24}$WT virus. The sequence encoding 3B$_2$ was modified by PCR utilizing mutagenic oligonucleotides P-PVKVs (5'-GCCCGATGG AGAGACCAGTTAAAGTTAAAGTGAAAG-CAAAAGCC; SEQ ID NO:13) and P-PVKVa (5' GGCTTTTGCTTTCACTTTAACTT-TAACTGGTCTCTCCATCGGGC; SEQ ID NO:14) engineered to introduce mutations at codons 9-12 of protein 3B$_2$ (also known as VPg$_2$, see FIG. 6). Thus, both WT3B$_{PVKV}$ and LL3B$_{PVKV}$ have the RQKP at amino acids 9-12 of the WT FMDV replaced by the BRV2 amino acids PVKV, respectively. The 3B antigen of WT FMDV has the amino acid sequence of SEQ ID NO:15; the mutant 3B comprising the substitution of the BRV2 amino acids has the amino acid sequence of SEQ ID NO:16 and is found in A$_{24}$WT3B$_{PVKV}$3D$_{YR}$ and A$_{24}$LL3B$_{PVKV}$3D$_{YR}$ viruses.

Mutagenic primers were used to introduce two new restriction sites into the full-length cDNA of FMDV as silent mutations. Primer 5'-GAATGGGGGCCGGCCAATCC AGT (SEQ ID NO:19) introduces a unique FseI restriction site at the N-terminal of VP4. Primer 5'-GACCTGCT-TAAGCTAGCCGGAGACGTTGAG (SEQ ID NO:20) was used to introduce a unique NheI restriction site in 2A of the FMDV coding region.

Full-length genomic clones were linearized with SwaI and in vitro transcribed using the T7 Megascripts system (Ambion, Austin, Tex.). Transcript RNAs were transfected into BHK-21 cells by electroporation as previously described (Rieder et al. 1993. J. Virol. 67:5139-5145). The transfected cells were seeded in 6-well plates and incubated for 24-48 h at 37 C and 5% CO$_2$. Virus was serially passed up to 10 times in BHK-21 or up to 4 times in BHK-α$_v$β$_6$. Virus stocks at passage 4 in BHK-α$_v$β$_6$ cells to be used in animal experiments and for the production of inactivated vaccine were entirely sequenced and stored at −70 C. Virus titers were determined by plaque assays as described below.

Figure 3A:
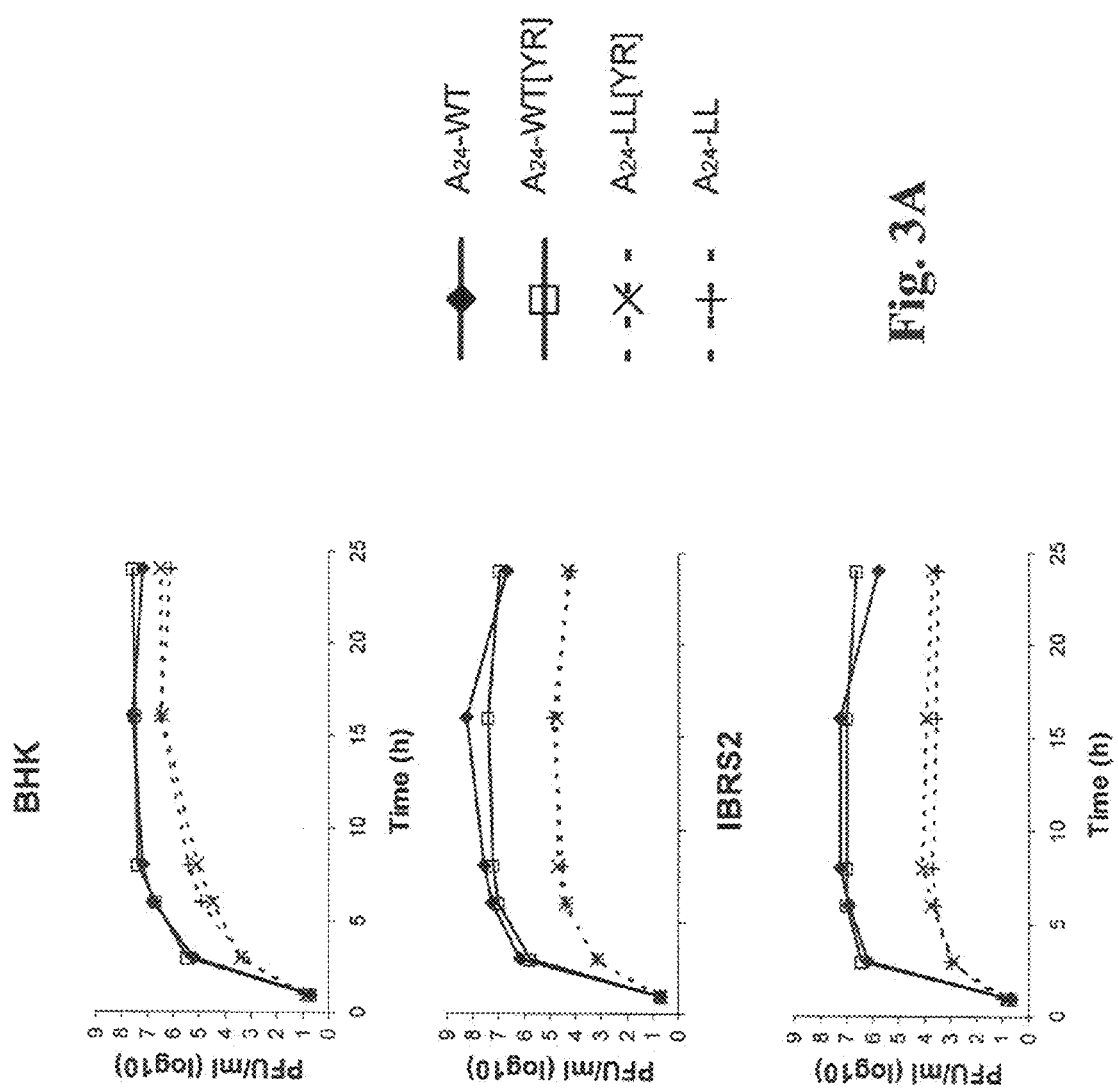
FIG. 3A shows 24 h single growth curves of FMDVs. Cell monolayers were mock- or infected with $A_{24}WT$, $A_{24}WT3D_{YR}$, $A_{24}LL$ or $A_{24}LL3D_{YR}$ viruses at a MOI of 5 PFU/cells. Procedures used for viral infection and titration of infectivity are described in Example 3. Each value represents the mean of triplicate assays.

In vitro growth kinetics of A$_{24}$LL, A$_{24}$WT3D$_{YR}$ and A$_{24}$LL3D$_{YR}$ mutants relative to parental A$_{24}$WT virus were determined using a high multiplicity of infection (MOI of 5) in BHK-21, LFBK cells and IBRS-2 cells (FIG. 3A). While the titers of the parental and A$_{24}$WT3D$_{YR}$ viruses peaked at about 6-8 hours post-inoculation (hpi) and remained the same over 24 h period of time in BHK-21 cells, mutants A$_{24}$LL, A$_{24}$LL3D$_{YR}$ exhibited a 10-fold decrease in the final virus yield. The growth restriction for leader deleted A$_{24}$LL and A$_{24}$LL3D$_{YR}$ viruses was more noticeable in cells of bovine or swine origin (~2.5-3 logs lower titers compared to WT viruses in these cells). As shown in FIG. 3B, the plaque morphologies of A$_{24}$LL and pA$_{24}$LL3D$_{YR}$ viruses were slightly smaller and more homogeneous in size (FIG. 3B) than A$_{24}$WT and A$_{24}$WT3D$_{YR}$ viruses.

Finally, the antigenic profile of mutant and parental viruses were examined by IP assays using MAbs F19-59 and F32-44, as described above (FIG. 3C). While immunoreactivity with MAbs F19-59 and F32-44 were positive with A$_{24}$WT virus, the reactivity was completely abolished in A$_{24}$LL3D$_{YR}$ and A$_{24}$WT3D$_{YR}$ 3D$^{pol}$ mutant viruses for F32-44. These results indicate that mutation of the 3D$^{pol}$ epitope (two amino acids replacement) affected the ability of FMDV to be recognized by MAbs F32-44 but not by F19-59.

Example 4

Rescue of Parental and Mutant Viruses, Viral Growth, and Plaque Assays; In Vitro Characterization of Double Negative Marker A$_{24}$LL3B$_{PVKV}$3D$_{YR}$ FMDV Infectious RNAs were in vitro transcribed from full-length cDNA clones of FMDV strain A$_{24}$WT or double marker mutants A$_{24}$WT3B$_{PVKV}$3D$_{YR}$ and A$_{24}$LL3B$_{PVKV}$3D$_{YR}$ and used to transfect BHK-21 cells. Mutants referred to as 3B$_{PVKV}$3D$_{YR}$ contain nucleotide substitutions within the viral proteins 3B and 3D$^{pol}$ by those sequences found in bovine rhinitis virus type 2 at similar positions (FIG. 6A). These substitutions were designed to produce mutant viruses that no longer react with FMDV-specific MAbs F8B (against 3B) and F32-44 (against 3D$^{pol}$) (FIG. 6B and FIG. 2, respectively). In vitro growth characteristics of mutants A$_{24}$WT3B$_{PVKV}$3D$_{YR}$ and A$_{24}$LL3B$_{PVKV}$3D$_{YR}$ was evaluated relative to the parental virus by plaque assays in BHK-21 cells. A$_{24}$WT3B$_{PVKV}$3D$_{YR}$ and A$_{24}$WT exhibited a mix of predominantly large plaques while A$_{24}$LL3B$_{PVKV}$3D$_{YR}$ exhibited reduced plaque morphologies (FIG. 6C). The identity and stability of 3B and 3D$^{pol}$ epitope mutations were confirmed by nucleotide sequence analysis of virus recovered from up to 15 virus serial passages in BHK-21 cells (data not shown).

For virus growth curves, BHK-21 monolayers were infected with $A_{24}WT$, $A_{24}WT3D_{YR}$, $A_{24}LL3D_{YR}$ or $A_{24}LL$ at a multiplicity of infection (MOI) of 5-10 pfu/cell. After 1 h of adsorption at 37° C., monolayers were rinsed with MES buffer (Morpholine Ethane Sulfonic acid 25 mM, 145 mM NaCl, pH 5.5), then twice with PBS, followed by addition of fresh BME containing no serum. At various times post-infection, viral titers were determined by plaque assays (Rieder et al. 1993, supra) using a 0.6% gum tragacanth overlay and incubated for 48 h at 37° C. Plates were fixed, stained with crystal violet (0.3% in Histochoice; Amresco, Solon, Ohio), and the plaques counted. Titers were expressed as plaque forming units per milliliter (PFU/ml) and performed in triplicates.

Example 5

Derivation of Chimeric Negative Marker FMDV Viruses

Figure 8A:
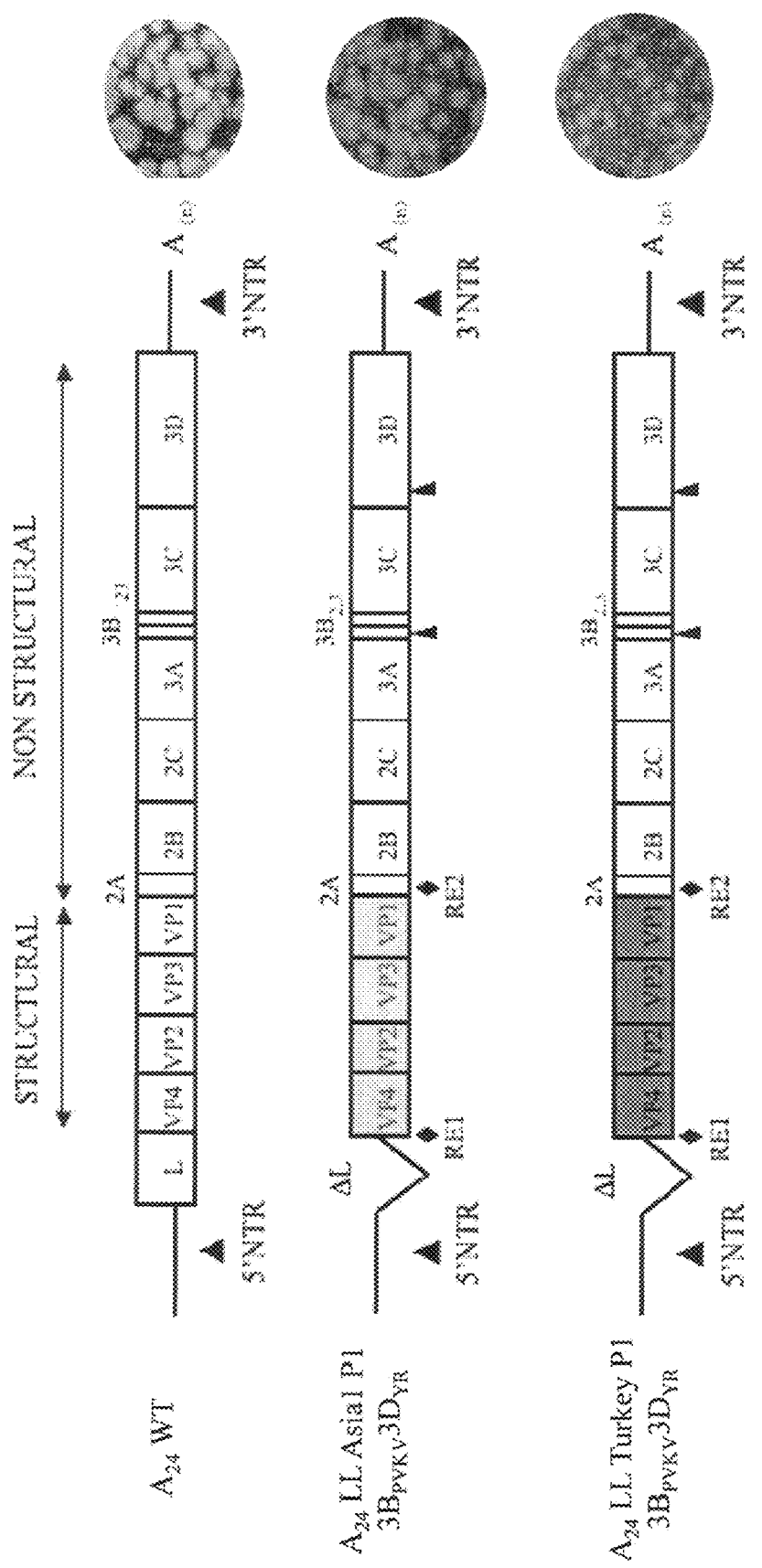
FIG. 8A is a schematic representation of the wild type and chimera FMDV genomes and relative locations of the modifications introduced in the viruses used in this study. $A_{24}LL$ Asia1-$A_{24}LL3B_{PVKV}3D_{YR}$ and A/Turkey/06-$A_{24}LL3B_{PVKV}3D_{YR}$ construct were generated by exchanging the capsid fragments from FMDV Asia1 Shamir and FMDV Turkey06, respectively and inserting into the p $A_{24}LL3B_{PVKV}3D_{YR}$ infectious clone derived from the FMDV outbreak strain $A_{24}$ Cruzeiro. Additional modifications present in the mutant plasmids included: ΔL: deletion of the leader gene; $3B_{23}$: only two copies of 3B genes; $3D^{pol}$: two amino acid substitutions at position $H_{27}Y$ and $N_{31}R$; two unique restriction endonuclease enzyme cloning sites 1 and 2 (♦, RE1, RE2). Titrations of infectivity for $A_{24}WT$ and chimeric FMDVs viruses were performed as stated in Example 6. The plaque phenotypes on BHK-21, LFBK, IBRS2 cell monolayers are shown.

Two mutant plasmids designated, A/Turkey/06-$A_{24}LL3B_{PVKV}3D_{YR}$ or Asia1-$A_{24}LL3B_{PVKV}3D_{YR}$ were derived by the replacement of the $A_{24}$ capsid with the capsid coding regions of Asia1 and Type A Turkey06 FMDV strains, respectively. The capsids were inserted by utilizing the two unique endonuclease sites, FseI and NheI, which were engineered into the backbone of the $pA_{24}LL\ 3B_{PVKV}3D_{YR}$ infectious cDNA clone (FIG. 8A).

The P1 capsid region of FMDV Asia1/Shamir was amplified by PCR using primers P1629 (5'-CCACAGGAATGGG GGCCGGCCAATCCAG; SEQ ID NO:21) containing a FseI site added by silent mutation in VP4 and P1634 (5'-TCTCCG GCTAGCTTAAGCAGGTCAAAATTCAGAAGCTGCTTC TCAGGTGCAATGA; SEQ ID NO:22) containing a silent mutation that introduces NheI site in the coding region in 2A. In addition, an internal NheI site in VP4 region was altered using silent mutations with primers P1690 (5'-GCCTG-GCAAGTTCTGCATTCAGTGG; SEQ ID NO:23) and P1691 (5'-CCACTGAATGCAGAACTTGCCAGGC; SEQ ID NO:24).

The P1 capsid region of FMDV A/Turkey06 was amplified by PCR using primers P1629 (5'-CCACAGGAATGGG GGCCGGCCAATCCAG; SEQ ID NO:21) containing a FseI site added by silent mutation in VP4 and P1622 (5'-TCTCCG GCTAGCTTAAGC AGGTCAAAATTCAGAAGT-TGTTTTGCAGGTGCA; SEQ ID NO:25) containing a silent mutation that introduces NheI site in the coding region in 2A.

The capsids of Asia and Turkey were then ligated into the backbone of $A_{24}LL\ 3B_{PVKV}3D_{YR}$ digested with FseI and NheI to generate Asia1-$A_{24}LL3B_{PVKV}3D_{YR}$ (SEQ ID NO: 26) and A/Turkey/06-$A_{24}LL3B_{PVKV}3D_{YR}$ (SEQ ID NO:27), respectively.

Full-length genomic clones were linearized with SwaI and in vitro-transcribed using the T7 Megascripts system (Ambion, Austin, Tex.). Transcript RNAs were transfected into BHK-21 cells by electroporation. The transfected cells were seeded in T-25 flasks and incubated for 24-48 h at 37 C and 5% $CO_2$. Virus was serially passed up to 4 times in BHK-21. Virus stocks at passages 4 and 5 in BHK-21 cells were used in animal experiments and for the production of inactivated vaccine and stored at −70° C. Virus titers were determined by plaque assays as described below.

Example 6

Rescue of Parental and Mutant Viruses, Viral Growth, and Plaque Assays; In Vitro Characterization of Double Negative Marker Chimeric FMDV BHK-21 cells were mock- or infected with the parent recombinant virus $A_{24}WT$, or chimeric viruses, $A_{24}LL$ Asia1 $3B_{PVKV}3D_{YR}$ and $A_{24}LL$ Turkey $3B_{PVKV}3D_{YR}$ at a MOI of 5 pfu/cell. At 5 hpi, cell lysates were collected and stored at −70° C. until further use. The double negative marker chimeric FMDV viruses $A_{24}LL$ Asia1 $3B_{PVKV}3D_{YR}$ and $A_{24}LL$ Turkey $3B_{PVKV}3D_{YR}$, rescued from BHK-21-transfected cells, confirmed presence of Asia1 and Turkey capsid, respectively by sequence analysis. Positive Asia1-$A_{24}LL3B_{PVKV}3D_{YR}$ clones were screened and identified by PCR using Asia P1-specific sense primer P1679 (5'-GCTGC-CCTCGAAAGAGGGAATAG; SEQ ID NO:28) and $A_{24}$ specific antisense primer R10 (5'-AAACTTTTCTTCTGAGGC-TATCCAT; SEQ ID NO:29) while positive A/Turkey/06-$A_{24}LL3B_{PVKV}3D_{YR}$ were identified by PCR using $A_{24}$ specific primer, L3 (5'-AGCACAGTAGCTTTGTTGT-GAAACT; SEQ ID NO:30) and Turkey06 P1 specific primer 1615 (5'-CGCGCCGCAAGAGGCCCCAGGT; SEQ ID NO:31).

In addition, the presence of the chimera viruses in infected cell culture cells can be easily detected on an agarose gel following RNA extractions and RT-PCR reactions. Viral RNA of $A_{24}LL$ Asia1-$A_{24}LL3B_{PVKV}3D_{YR}$ and A/Turkey/06-$A_{24}LL3B_{PVKV}3D_{YR}$ were extracted from passage 4 using the RNeasy® Mini Kit (Qiagen) according to the manufacturer's instructions. One-Step Reverse Transcriptase Polymerase Chain Reaction (RT-PCR) (Invitrogen) was performed to detect the presence and/or absence of specific mutations in the chimera FMDV viruses. Primers P1457 (5'-TGACT-TCCA CGCAGGCATTTTCC; SEQ ID NO:32) and R8 (5'-TAGTTAAATGAAGCAGGAAGC TGT; SEQ ID NO:33) were used to detect the absence of the leader gene while primers L5 (5'-ACAACTACTACATGCAGCAATACCA; SEQ ID NO:34) and R6 (5'-AGTGAATTT GGAGTT-TAGTCCAGTG; SEQ ID NO:35) were used to show the absence of the $A_{24}$ capsid in the chimera viruses. Likewise, primers P1690 (5'-GCCTGGCAAGTTCTGC ATTCAGTGG; SEQ ID NO:23) and P1634 (5'-TCTCCG-GCTAGCTTAAGCAGGTCAAA ATTCAGAAGCTGCT-TCTCAGGTGCAATGA; SEQ ID NO:22) were used to detect Asia1 capsid while P1590 (5'-GCTCCACTGACAC-TACCTCCAC; SEQ ID NO:36) and P1612 (5'-GCCG-GCGCTGACCGACACGACC; SEQ ID NO:37) were used to detect Turkey06 capsid. In addition, primers L13 (5'-TTTTCAAACAGATCTCAATTCCTTC; SEQ ID NO:38) and R15 (5'-GCAAGCAAACTTGTATTCTCTTTTC; SEQ ID NO:39) were used to detect the two copies of 3B in the chimera viruses.

All positive clones were sequenced to verify the absence of the leader gene and presence of Asia1 or Turkey P1, $3B_{PVKV}$ and $3D_{YR}$ mutations. Complete viral sequences detect no other mutations except for the expected lack of the leader coding region, modified 3B region and mutation at the $3D^{pol}$ locus encoding the YR epitope. FIG. 8B shows RT-PCR results (using $A_{24}$ capsid specific primers for $L^{pro}$) fail to detect that $L^{pro}$ on $A_{24}LL$ Asia1-$A_{24}LL3B_{PVKV}3D_{YR}$ and $A_{24}LL$ A/Turkey/06-$A_{24}LL3B_{PVKV}3D_{YR}$ infected cells extracts, indicating the lack of the two regions on these chimera viruses. As expected RT-PCR reactions using specific primers of Asia1 capsid sequences gave a product for Asia1-

$A_{24}LL3B_{PVKV}3D_{YR}$ virus while primers specific for Turkey06 capsid detected its presence on A/Turkey/06-$A_{24}LL3B_{PVKV}3D_{YR}$ but not on $A_{24}WT$ virus. In addition, the presence of only two copies of 3B peptide-coding sequences can be detected on the chimeric viruses compared to the $A_{24}WT$ virus.

Figure 9:
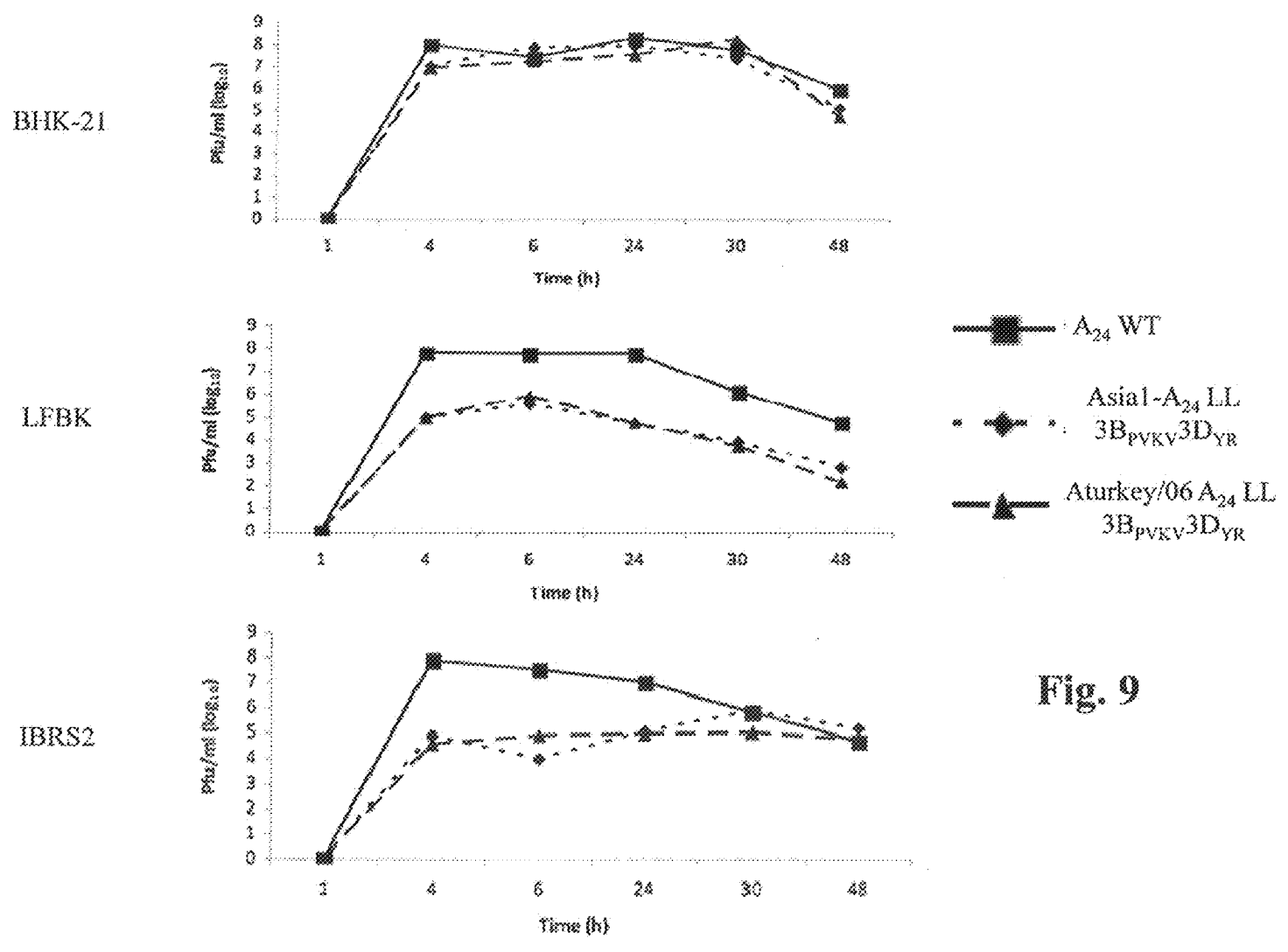

Plaque assays of Asia1-$A_{24}LL3B_{PVKV}3D_{YR}$ and A/Turkey/06-$A_{24}LL3B_{PVKV}3D_{YR}$ viruses show similar viral titers when compared to the parental $A_{24}WT$ virus (FIG. 8A). However, the plaque morphology of the chimera viruses, as expected, is significantly smaller and therefore, requires a 72 h overlay incubation when compared to a 48 h incubation of the $A_{24}WT$ virus. In addition, in vitro growth kinetics of Asia1-$A_{24}LL3B_{PVKV}3D_{YR}$ and A/Turkey/06-$A_{24}LL3B_{PVKV}3D_{YR}$ mutants relative to parental $A_{24}WT$ virus were determined using a high multiplicity of infection (MOI of 5) in BHK-21, LFBK cells and IBRS-2 cells (FIG. 9). Titers of the parental $A_{24}WT$ as well as the chimera viruses, Asia1-$A_{24}LL3B_{PVKV}3D_{YR}$ and A/Turkey/06-$A_{24}LL3B_{PVKV}3D_{YR}$ peaked at 4 hours post infection (hpi) and remained the same over 30 h period in BHK-21 cells. However, the chimera viruses showed significantly restricted growth (~2-3 logs lower titers) in both bovine and swine cells when compared to the $A_{24}WT$ virus.

For Western blot analysis, cell lysates were resuspended in STE buffer (10 mM Tris ph 8, 1 mM EDTA, 0.1 M NaCl) supplemented with 1% Triton-X100 and Benzonase (Novagen). 8 μl of cell lysates were run under denaturing conditions in a 12% SDS-PAGE gel (Invitrogen) and transferred onto nitrocellulose membranes using XCell II™ system (Invitrogen). The blots were blocked with 5% skim milk in PBS-Tween (PBST) for 1 h at room temperature followed by an additional incubation of 1 h with FMDV-specific monoclonal antibodies (mAb F32-44 (1:5), mAb F19-6 (1:100), mAb F8B (1:500) in 1% skim milk and PBST. Blots were then washed twice with PBST for 5 minutes each and incubated for an additional hour with goat anti-mouse IgG antibody conjugated to horse radish peroxide (HRP) (1:20,000) diluted in 1% skim milk and PBST. The blots were subsequently washed three times with PBST and developed with SuperSignal West Dura Extended Duration Substrate (ThermoScientific). Mouse anti-tubulin IgG conjugated to HRP was used at a dilution of 1:500 as a loading control.

The antigenic profiles of the parental as well as chimera viruses were examined by western blots using MAbs F19-6, F32-44 and F8B. FIG. 10 shows that BHK-21 cell lysates infected with the $A_{24}WT$ virus reacted with all three MAbs whereas both Asia1-$A_{24}LL3B_{PVKV}3D_{YR}$ and A/Turkey/06-$A_{24}LL3B_{PVKV}3D_{YR}$ viruses failed to react with MAbs F8B and F32-44. These results indicate that mutations on the 3B region as well as the $3D^{pol}$ epitope (two amino acids replacement) allows differentiation of the chimeric viruses from wild-type virus by their lack of reactivity with MAbs F8B and F32-44.

Example 7

Pathogenicity of $A_{24}WT3D_{YR}$ and $A_{24}LL3D_{YR}$ Viruses in Cattle and Swine To examine the influence of mutations on pathogenicity and the serological response to recombinant $A_{24}WT3D_{YR}$ and $A_{24}LL3D_{YR}$ mutants in comparison with the parental virus $A_{24}WT$ in cattle, we performed aerosol inoculation of these viruses in cattle, followed by measurement of clinical disease and virus shed to the environment.

Two Holstein steers for $A_{24}WT$ and three for each mutant virus were marked and housed in a single room. Prior to infection the animals were moved to separate rooms and each of them were inoculated by aerosol with either $1 \times 10^7$ (for $A_{24}WT$) or $1$-$3 \times 10^6$ $TCID_{50}$ (for $A_{24}WT3D_{YR}$ and $A_{24}LL3D_{YR}$ mutants) using a method previously described (Pacheco et al. 2010. Vet. J. 183:46-53). Sera and oral secretions were collected daily for up to 9 days for $A_{24}WT$ and 21 days for $A_{24}WT3D_{YR}$ and $A_{24}LL3D_{YR}$ mutants, as well as temperature and clinical evaluation for the same period of time. Shedding of virus in the air was also monitored using a Dry Filter Unit (DFU) Model 1000 air pump developed by the Program Executive Office for Chemical Biological Defense (PEO-CBD). Clinical signs were scored as 1 credit for each affected foot and one credit for the affected head (vesicles in mouth, nostrils, tongue or lips). FMDV RNA was measured in sera, swabs and air samples by rRT-PCR as described below.

Following inoculation, several parameters including fever, clinical score, viremia, neutralizing antibodies and the presence of virus in air and oral swabs samples were recorded and analyzed (Table 1). Nine steers allocated into independent rooms were aerosol-inoculated with approximately $1 \times 10^7$ $TCID_{50}$ of $A_{24}WT$ or $1$-$3 \times 10^6$ $TCID_{50}$ total of either $A_{24}WT3D_{YR}$ or $A_{24}LL3D_{YR}$ viruses. Animals inoculated with $A_{24}WT$ virus (bovines #7109, 7110) showed viremia, virus in saliva and fever by 2 dpi. Clinical signs appeared by 2-4 dpi and reaching a high clinical score by 5-7 dpi when neutralizing antibodies were first detectable. Bovines #7199, 1 and 2 inoculated with $A_{24}WT3D_{YR}$ virus showed viremia by 2 dpi reaching a peak at 3-4 dpi. Virus was detectable in saliva starting at 2-3 dpi and reaching a peaking at 2-3 dpi. Fever appeared at 2 dpi and lasted up to 3 or 5 dpi. Clinical signs appeared by 4-6 dpi and virus shed in the air started by 3 dpi. Serum neutralizing antibodies were first detectable by 5-6 dpi in all three cows (Table 1). Vesicular fluid was collected from lesions on the 4 and 6 dpi (bovine #1, 2 and 7199) and each sample was separately processed for RT/PCR and sequencing. These fluids contained viruses that were indistinguishable from the inoculated virus in their genome sequences, further indicating that the $A_{24}WT3D_{YR}$ virus has not changed during growth in bovines. In clear contrast with the pathogenic profile of $A_{24}WT3D_{YR}$ and $A_{24}WT$ viruses, the three animals inoculated with $A_{24}LL3D_{YR}$ (bovine #7201, 3 and 4; Table 1) showed absence of fever, viremia, clinical manifestation, or shedding of virus in saliva or air samples. The level of attenuation was such, that these animals did not develop significant levels of neutralizing antibodies during the course of the experiment (Table 1), even though antibodies against viral structural proteins were demonstrated by 21 dpi by radioimmunoprecipitation assays (data not shown).

TABLE 1

Responses of Cattle to Infection with $A_{24}WT$, $A_{24}WT3D_{YR}$ or $A_{24}LL3D_{YR}$ Viruses

| Bovine #[a] | Virus | Viremia Max Titer[b] (DPI)[c] | Virus in Saliva Max Titer[b] (DPI)[c] | Fever (DPI)[e] | Max Clinical Score/Max Achievable[f] (DPI)[g] | Neutralization TiterMax[h] (Starting DPI)[i] | Shedding In Air TiterMax[j] (DPI)[c] |
|---|---|---|---|---|---|---|---|
| 7109 | $A_{24}WT$ | 7.60 (3) | 8.90 (3) | Yes (2; 3) | 5/5 (7) | 2.4 (5) | 5.57 (5) |
| 7110 | $A_{24}WT$ | 7.31 (4) | 10.18 (2) | Yes (2 to 5) | 5/5 (5) | 2.4 (6) | ND |
| 7199 | $A_{24}WT3D_{YR}$ | 6.73 (3) | 9.58 (6) | Yes (6; 8) | 1/5 (6) | 2.7 (6) | ND |
| 1 | $A_{24}WT3D_{YR}$ | 7.55 (3) | 8.00 (4) | Yes (2; 3) | 5/5 (6) | 3.0 (5) | 3.66 (7) |
| 2 | $A_{24}WT3D_{YR}$ | 7.95 (3) | 9.47 (4) | Yes (2; 3) | 2/5 (7) | 3.0 (5) | 2.55 (4) |
| 7201 | $A_{24}LL3D_{YR}$ | Neg[k] | Neg | No | 0/5 | <0.9 | Neg[l] |
| 3 | $A_{24}LL3D_{YR}$ | Neg | Neg | No | 0/5 | <0.9 | Neg |
| 4 | $A_{24}LL3D_{YR}$ | Neg | Neg | No | 0/5 | <0.9 | Neg |

[a]Bovines were inoculated with $1 \times 10^7$ $TCID_{50}$ of $A_{24}WT$ or $1-3 \times 10^6$ $TCID_{50}$ of $A_{24}WT[YR]$ and $A_{24}LL[YR]$ of virus by aerosolization.
[b]Log 10 RNA copy number/ml.
[c]Indicates the day after inoculation that peak of virus was detected.
[d]Fever defined as rectal temperature ≥ 40.0° C.
[e]Indicates days fever was detected.
[f]Clinical scores were based on the number of feet with vesicular lesions and lesions in the head (mouth, nostrils, lips or tongue), with a maximum of five.
[g]Indicates the day after inoculation that maximum score was reached.
[h]FMDV-specific neutralizing antibody titer (log 10 of reciprocal of the last serum dilution to neutralize 100 $TCID_{50}$ of virus in 50% of the wells.
[i]Indicates the first day after inoculation that neutralizing antibodies were detected.
[j]Log 10 RNA copy number/1000 liters.
[k]RNA copy number minimum detection level = $10^{2.4}$/ml.
[l]RNA copy number minimum detection level = $10^{0.8}$/1000 liters.
ND: Not Determined Mutant ($A_{24}LL3D_{YR}$) virus was tested for its virulence in swine. Briefly, two 20-kg pigs were inoculated intradermally with $10^5 TCID_{50}$ of each of the virus and 48 hours later two naïve pigs were added in direct contact. Sera, nasal and oral secretions were collected daily for up to 21 days post inoculation (dpi), as well as rectal temperature and clinical evaluation. FMDV RNA was measured in sera, swabs and air samples by rRT-PCR as described below.

Experimental inoculation in the heel-bulb of susceptible pigs with $10^5$ $TCID_{50}$ of $A_{24}LL[YR]$ virus was performed in two animals (Table 2, animals #40 and #41), and two contact animals (#43 and #44) were moved to the room 48 hpi and housed together for 19 days. Among the inoculated animals, only one of the directly inoculated pigs (#41) had for one day (1 dpi) detectable RNA in serum ($10^{5.44}$ viral RNA copy numbers per ml) and $10^{5.45}$ viral RNA copy numbers per ml in oral swabs at 2 dpi. This animal also developed low serum neutralizing antibodies titers starting at 4 dpi, but in the absence of any clinical manifestation of FMD. Interestingly, no virus was shed from this pig to the second directly inoculated pig, nor it did to the two in-contact animals (#43 and #44). All pigs were never pirexic (temperatures remained below 40° C.) during the course of this experiment. Furthermore, none of the contact pigs showed clinical signs of FMD or vesicular lesions throughout the experiment.

TABLE 2

Response of Swine: Direct Inoculation (Pigs #40, #41) or Contact Inoculation (Pigs #42; #43) with $10^5$ $TCID_{50}$ of $A_{24}LL3D_{YR}$.

Pig #40

|  | 0 dpi[a] | 1 dpi | 2 dpi | 3 dpi | 4 dpi | 5 dpi | 6 dpi |
|---|---|---|---|---|---|---|---|
| Viremia[b] | Neg[c] | Neg | Neg | Neg | Neg | Neg | Neg |
| Virus in Oral Swab[b] | Neg | Neg | Neg | Neg | Neg | Neg | Neg |
| Virus in Nasal Swab[b] | Neg | Neg | Neg | Neg | Neg | Neg | Neg |
| Neutralization Titer[d] | <0.9 | <0.9 | <0.9 | <0.9 | <0.9 | <0.9 | <0.9 |
| Clinical Score | Neg | Neg | Neg | Neg | Neg | Neg | Neg |

Pig #41

|  | 0 dpi | 1 dpi | 2 dpi | 3 dpi | 4 dpi | 5 dpi | 6 dpi |
|---|---|---|---|---|---|---|---|
| Viremia | Neg | 5.44 | Neg | Neg | Neg | Neg | Neg |
| Virus in Oral Swab | Neg | Neg | 5.45 | Neg | Neg | Neg | Neg |
| Virus in Nasal Swab | Neg | Neg | Neg | Neg | Neg | Neg | Neg |
| Neutralization Titer | <0.9 | <0.9 | <0.9 | <0.9 | <0.9 | 1.2 | 1.2 |
| Clinical Score | Neg | Neg | Neg | Neg | Neg | Neg | Neg |

Pig #42

|  | 0 dpc[e] | 1 dpi | 2 dpi | 3 dpi | 4 dpi | 5 dpi | 6 dpi |
|---|---|---|---|---|---|---|---|
| Viremia | Neg | Neg | Neg | Neg | Neg | Neg | Neg |
| Virus in Oral Swab | Neg | Neg | Neg | Neg | Neg | Neg | Neg |
| Virus in Nasal Swab | Neg | Neg | Neg | Neg | Neg | Neg | Neg |
| Neutralization Titer | <0.9 | <0.9 | <0.9 | <0.9 | <0.9 | <0.9 | <0.9 |
| Clinical Score | Neg | Neg | Neg | Neg | Neg | Neg | Neg |

TABLE 2-continued

Response of Swine: Direct Inoculation (Pigs #40, #41) or Contact Inoculation (Pigs #42; #43) with $10^5$ TCID$_{50}$ of A$_{24}$LL3D$_{YR}$.

| | Pig #43 | | | | | | |
|---|---|---|---|---|---|---|---|
| | 0 dpc | 1 dpi | 2 dpi | 3 dpi | 4 dpi | 5 dpi | 6 dpi |
| Viremia | Neg | Neg | Neg | Neg | Neg | Neg | Neg |
| Virus in Oral Swab | Neg | Neg | Neg | Neg | Neg | Neg | Neg |
| Virus in Nasal Swab | Neg | Neg | Neg | Neg | Neg | Neg | Neg |
| Neutralization Titer | Neg | Neg | Neg | Neg | Neg | Neg | Neg |
| Clinical Score | Neg | Neg | Neg | Neg | Neg | Neg | Neg |

[a]Days Post-inoculation.
[b]Log 10 RNA copy number/ml.
[c]RNA copy number minimum detection level = $10^{2.4}$/ml.
[d]FMDV-specific neutralizing antibody titer (log 10 of reciprocal of the last serum dilution to neutralize 100 TCID$_{50}$ of virus in 50% of the wells).
[e]Days post-contact inoculation Example 8

Figure 7:
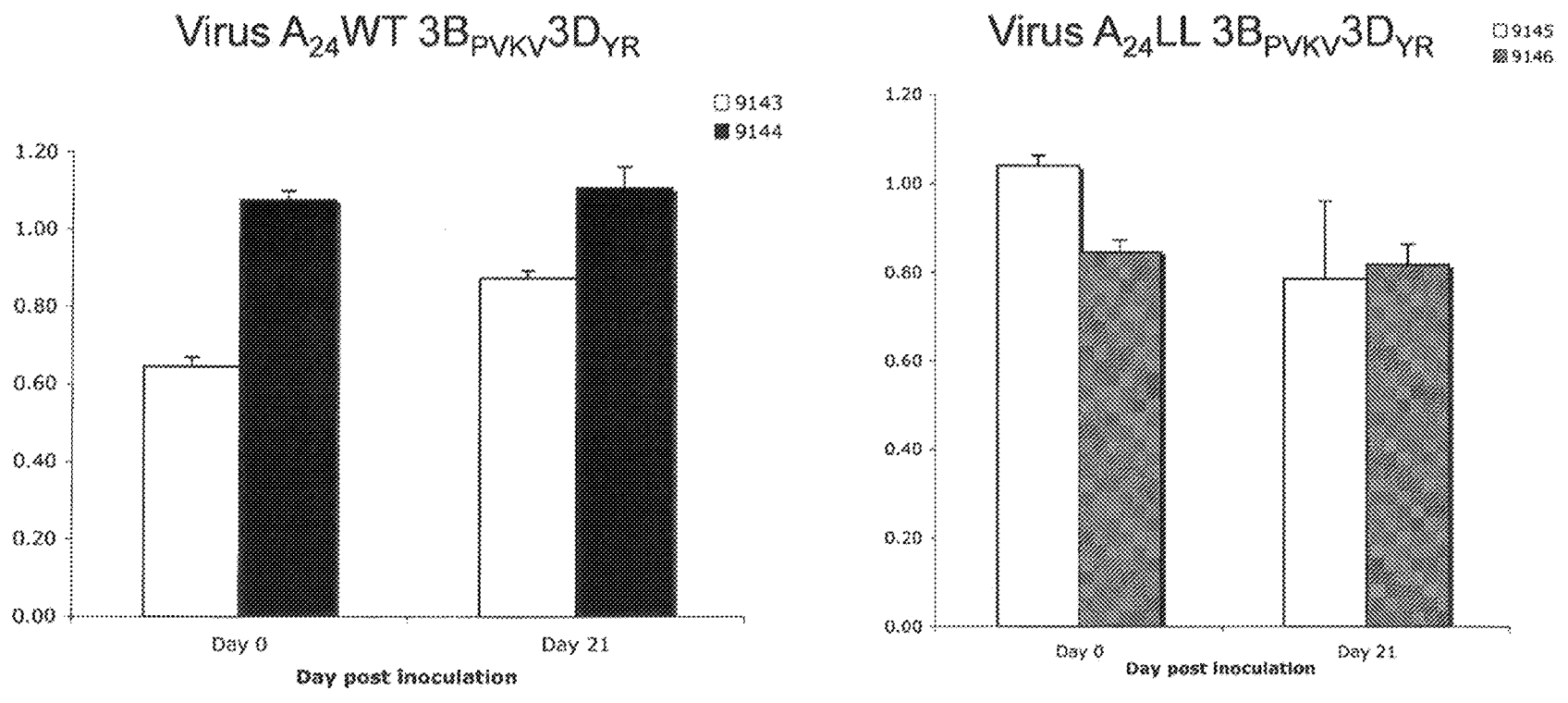

Double FMDV Negative Marker A$_{24}$LL3B$_{PVKV}$3D$_{YR}$: Attenuated in Cattle and Induction of an Immune Response Against the Non-Structural Viral Protein 3B To examine the effect of epitope mutations on FMDV virulence in cattle, A$_{24}$WT3B$_{PVKV}$3D$_{YR}$ and A$_{24}$LL3B$_{PVKV}$3D$_{YR}$ viruses were compared in two groups of bovines inoculated with $10^6$ TCID$_{50}$ of virus and monitored for clinical FMD. Results from this experiment are shown in Table 3. While A$_{24}$WT3B$_{PVKV}$3D$_{YR}$ was highly pathogenic, effectively inducing fever and clinical signs in cattle, double epitope mutant A$_{24}$LL3B$_{PVKV}$3D$_{YR}$ virus failed to induce FMD, neither produced vesicles at the site of inoculation. Attenuation of A$_{24}$LL3B$_{PVKV}$3D$_{YR}$ virus was also reflected in lack of viremia or virus shedding (determined on bovine #9146) consistent with the in vivo results of the single marker A$_{24}$LL3D$_{YR}$ mutant virus (see Tables 1 and 2). Conservation of 3B and 3D$^{pol}$ epitope mutations were confirmed by nucleotide sequence analysis of virus from tissues or vesicular fluid recovered from A$_{24}$WT3B$_{PVKV}$3D$_{YR}$-infected animals (data not shown). Antibody responses to FMDV 3B epitopes were measured by an in house cELISA using MAb F8B as competitor and a 3B peptide (see Material and Methods). Sera collected from animals inoculated with the marker A$_{24}$WT3B$_{PVKV}$3D$_{YR}$ virus by the aerosol route (days 0 and 21) or inoculated with A$_{24}$LL3B$_{PVKV}$3D$_{YR}$ by the intradermolingual (days 0 and 21) route were analyzed against FMDV 3B peptide in a cELISA (FIG. 7). Results showed that the sera from A$_{24}$WT3B$_{PVKV}$3D$_{YR}$ (bovine #9143 and 9144) or A$_{24}$LL3B$_{PVKV}$3D$_{YR}$ (bovine #9145 and 9146) double mutant-infected animals at day 21 post-infection were unable to compete with MAbF8B as the sera obtained from these animals prior to infection (day 0, uninfected animals) were, indicating a lack of anti-3B epitope antibodies (FIG. 7). The presence of neutralizing antibody response measured at day 14 (Table 3) showed titers of 1.5 and 2.5 for bovines #9145 and #9156 (infected with LL double mutant) and of 3.6 and 3.0 for the WT double mutant-infected animals #9143 and #9144.

TABLE 3

Virus titers, clinical samples and virus shedding measurements from cattle following infection with A$_{24}$WT3B$_{PVKV}$3D$_{YR}$ or A$_{24}$LL3B$_{PVKV}$3D$_{YR}$ viruses.

| Bovine #[a] | Virus | Viremia, Maximum Titer.[b] (DPI)[c] | Virus in Saliva, Maximum Titer[b] (DPI)[c] | Fever[d] (DPI)[e] | Maximum Clinical Score/Maximum achievable[f] (DPI)[g] | Neutralization Titer at 14 DPI[h] | Shedding in air. Maximum Titer[i] (DPI)[c] |
|---|---|---|---|---|---|---|---|
| 9143 | A$_{24}$WT3B$_{PVKV}$3D$_{YR}$ | 7.40 (4) | 9.03 (5) | Yes (3) | 1/5 (5) | 3.6 | 6.29 (6) |
| 9144 | A$_{24}$WT3B$_{PVKV}$3D$_{YR}$ | 7.92 (4) | 8.85 (5) | Yes (4) | 4/5 (7) | 3.0 | 5.45 (7) |
| 9145 | A$_{24}$LL3B$_{PVKV}$3D$_{YR}$ | Negative | Negative | No | 0/5 | 1.5 | ND[j] |
| 9146 | A$_{24}$LL3B$_{PVKV}$3D$_{YR}$ | Negative | Negative | No | 0/5 | 2.4 | Negative |

[a]Bovines were inoculated with 7 x 10^6 TCID$_{50}$ of A$_{24}$WT3B$_{PVKV}$3D$_{YR}$ by aerosolation or with 1 x 10^6 TCID$_{50}$ of A$_{24}$LL3B$_{PVKV}$3D$_{YR}$ virus by the intradermolingual route.
[b]Log10 RNA copy number/ml.
[c]Indicates the day after inoculation that peak of virus was detected
[d]Fever defined as rectal temperature ≥ 40.0° C.
[e]Indicates days fever was detected.
[f]Clinical scores were based on the number of feet with vesicular lesions and lesions in the head (mouth, nostrils, lips or tongue), with a maximum of five.
[g]indicates the day after inoculation that maximum score was reached.
[h]FMDV-specific neutralizing antibody titer (log10 of reciprocal of the last serum dilution to neutralize 100 TCID$_{50}$ of virus in 50% of the wells)
[i]Log10 RNA copy number/1000 liters
[j]ND: not determined

Example 9

Antigen Production and Vaccine Formulation

The $A_{24}LL3D_{YR}$ vaccine antigen was harvested from infected BHK-21 monolayers cells and inactivated with 5 mM BEI for 24 h at 25° C. The inactivated antigen was then concentrated and partially purified with 8% polyethylene glycol 8000. The vaccine was prepared as water-in-oil-in-water (WOW) emulsion with Montadine ISA 206 (Seppic, Paris) according to the manufacturer instructions. Briefly, the oil adjuvant was mixed into the aqueous antigen phase (50:50) at 30° C. for 15 minutes and stored at 4° C. for 24 hours, followed by another brief mixing cycle for 10 minutes. The integrity of 146S particles and antigen concentration present in the experimental vaccine was determined by 10-30% sucrose density gradient and 260 nm densitometry.

The commercial vaccine used for comparison was a polyvalent vaccine (Biogenesis-Bagó, Bioaftogen serie 565 composed of $O_1$ Campos, $A_{24}$ Cruzeiro, A Arg 2001 and $C_3$ Indaial.

Example 10

Vaccination with BEI-inactivated $A_{24}LL3D_{YR}$ Virus Protects Cattle Against Challenge with Pathogenic $A_{24}WT$ FMDV.

To determine the efficacy of the marker vaccine in providing immunological protection against challenge with parental $A_{24}WT$ virus, the BEI-inactivated $A_{24}LL3D_{YR}$ vaccine was tested in parallel with a commercial FMDV vaccine in a cattle vaccine trial. Ten Holstein steers, between 250 and 300 kg, were allowed to acclimatize from shipping for 1 week before testing was initiated. Eight steers were vaccinated with either the commercial vaccine (cattle 863, 864, 865 and 866) or with $A_{24}LL3D_{YR}$/water-in-oil-in-water (WOW, cattle 867, 868, 869, 870) vaccine, intramuscularly in the neck. As shown in Table 4, four cattle (#863-866) were each inoculated intramuscularly with 1 dose of a commercial trivalent vaccine and four other steers (#867-870) received the $A_{24}LL3D_{YR}$ BEI-inactivated vaccine. Cattle 871 and 872 were vaccinated with sterile PBS to be used as unvaccinated controls.

TABLE 4

Specific neutralizing antibody response against FMDV $A_{24}WT$ after vaccination with commercial polyvalent or $A_{24}LL3D_{YR}$ vaccine and challenged with FMDV $A_{24}WT$.

| | Bovine # | Days Post Vaccination | | | | | | |
|---|---|---|---|---|---|---|---|---|
| | | $0^a$ | 7 | 14 | $21^b$ | 28 | 35 | 42 |
| Commercial Vaccine | 863 | <$0.9^c$ | 0.9 | 1.2 | 1.5 | 3.9 | 4.2 | 3.9 |
| | 864 | <0.9 | 1.2 | 0.9 | 0.9 | 3.6 | 3.6 | 3.6 |
| | 865 | <0.9 | 0.9 | 0.9 | 1.8 | 3.9 | 3.6 | 3.9 |
| | 866 | <0.9 | 1.2 | 1.5 | 2.1 | ND | ND | ND |
| $A_{24}LL3D_{YR}$ Vaccine | 867 | <0.9 | 2.1 | 2.4 | 2.7 | 3.3 | 3.3 | 3.0 |
| | 868 | <0.9 | 2.4 | 2.1 | 2.7 | 3.3 | 3.6 | 3.9 |
| | 869 | <0.9 | 2.1 | 2.4 | 2.7 | 3.0 | 2.7 | 3.0 |
| | 870 | <0.9 | 2.1 | 1.8 | 2.4 | 3.0 | 3.3 | 3.0 |
| PBS (Controls) | 871 | <0.9 | <0.9 | <0.9 | <0.9 | 2.4 | 3.0 | 3.6 |
| | 872 | <0.9 | <0.9 | <0.9 | <0.9 | 2.7 | 3.3 | 3.6 |

$^a$Day of Vaccination
$^b$Day of Challenge
$^c$Virus neutralizing titers of serum antibodies On day 21 post vaccination all 10 cattle were challenged intradermolingually with $10^4$ $BTID_{50}$ (50% bovine tongue infectious doses; In: Manual of Diagnostic Tests and Vaccines for Terrestrial Animals of 2009, edited and published by OIE—The World Organization for Animal Health, *Foot and mouth disease*, Chapter 2.1.5) of parental $A_{24}WT$. The animals were then monitored at 0, 4, 7 and 10 days post-challenge for the appearance of localized and generalized lesions and rectal temperatures were recorded. Sera, nasal swabs (cotton tip, immersed in 2 ml of minimum essential medium with 25 mM HEPES and 1% FBS) and temperature were collected daily. Clinical signs were scored as 1 credit for each affected foot, presence of vesicles in the head was not considered due to lingual inoculation of challenge. FMDV RNA was measured in sera, swabs and air samples by rRT-PCR as described below.

The 8 immunized cattle, regardless of the vaccine they received, were protected from challenge with parental $A_{24}WT$ virus as observed by the absence of generalized vesicles or high temperatures. All vaccinated animals developed a detectable FMDV-specific neutralizing antibody response by 7 days post-vaccination (dpv), with slightly higher neutralizing titers for our experimental $A_{24}LL3D_{YR}$ vaccine more likely due to a higher content of antigen mass (approximately 23 ug/dose $A_{24}LL3D_{YR}$/dose). By day 21 all animals but one (#864) had increased titers of serum neutralizing antibodies. In contrast, the un-vaccinated naïve animals (bovines #871, 872) that received PBS had no detectable FMDV-specific antibody response (Table 4).

Twenty one days dpv, all animals were challenged by intradermal inoculation at four sites in the tongue with 10,000 bovine infectious doses ($BTID_{50}$) of parental FMDV $A_{24}WT$. Both control animals developed fever within 24-72 h post challenge (dpc) while only one of the commercial vaccine-immunized animals developed fever at 3 and 4 dpc. All other animals showed no fever during the experiment (Table 5). Both naïve animals developed lesions on all four feet. In contrast, none of the vaccinated animals showed signs of FMD during the term of this experiment (up to 10 dpc, Table 6). Both control animals showed viremia at 1 to 5 dpc and no virus was detected in the sera of any of the vaccinated animals (data not shown). Virus was detected from nasal secretions in all animals, either vaccinated or not (data not shown).

TABLE 5

Rectal Temperatures$^b$ of cattle (# 863-872) after challenge with FMDV $A_{24}WT$.

| | # | Days Post Vaccination | | | | | | | | | | | |
|---|---|---|---|---|---|---|---|---|---|---|---|---|---|
| | | $21^a$ | 22 | 23 | 24 | 25 | 26 | 27 | 28 | 29 | 30 | 31 | 32 |
| Commercial Vaccine | 863 | 38.8 | 39.1 | 39.6 | 40.8 | 40.3 | 39.3 | 39.7 | 39.6 | 39.2 | 39.1 | 39.1 | 39.1 |
| | 864 | 39.0 | 38.9 | 39.1 | 39.3 | 39.3 | 39.6 | 39.3 | 39.2 | 39.3 | 39.2 | 39.1 | 38.9 |

TABLE 5-continued

Rectal Temperatures[b] of cattle (# 863-872) after challenge with FMDV $A_{24}$WT.

| | # | 21[a] | 22 | 23 | 24 | 25 | 26 | 27 | 28 | 29 | 30 | 31 | 32 |
|---|---|---|---|---|---|---|---|---|---|---|---|---|---|
| | 865 | 38.9 | 39.4 | 39.7 | 39.9 | 38.9 | 39.4 | 39.8 | 39.4 | 39.6 | 39.2 | 39.3 | 39.0 |
| $A_{24}LL3D_{YR}$ | 867 | 39.1 | 39.9 | 39.8 | 39.9 | 39.7 | 39.8 | 39.7 | 39.4 | 39.3 | 39.6 | 39.1 | 39.0 |
| Vaccine | 868 | 38.7 | 39.7 | 38.9 | 39.0 | 38.9 | 39.3 | 39.2 | 39.3 | 39.4 | 39.2 | 39.3 | 38.9 |
| | 869 | 39.1 | 39.7 | 39.9 | 39.7 | 39.1 | 39.4 | 39.4 | 39.7 | 39.8 | 39.4 | 39.1 | 39.2 |
| | 870 | 39.0 | 39.1 | 38.8 | 39.2 | 39.1 | 39.3 | 39.4 | 39.0 | 39.1 | 39.2 | 39.2 | 38.9 |
| PBS | 871 | 38.6 | 38.9 | 40.1 | 40.7 | 39.3 | 39.3 | 39.1 | 39.1 | 39.2 | 39.3 | 38.9 | 39.0 |
| (Controls) | 872 | 39.1 | 41.1 | 41.2 | 40.6 | 39.9 | 39.9 | 39.4 | 39.3 | 39.8 | 39.0 | 39.1 | 39.2 |

[a]Day of challenge
[b]Temperature (° C.); Considered fever when ≥40.0° C.

TABLE 6

Assessment of Clinical scores[a] of cattle after challenge with FMDV $A_{24}$WT[b].

| | Bovine # | Days Post Vaccination | | | |
|---|---|---|---|---|---|
| | | 21[c] | 25 | 28 | 32 |
| Commercial | 863 | 0 | 0 | 0 | 0 |
| Vaccine | 864 | 0 | 0 | 0 | 0 |
| | 865 | 0 | 0 | 0 | 0 |
| $A_{24}LL3D_{YR}$ | 867 | 0 | 0 | 0 | 0 |
| Vaccine | 868 | 0 | 0 | 0 | 0 |
| | 869 | 0 | 0 | 0 | 0 |
| | 870 | 0 | 0 | 0 | 0 |
| PBS | 871 | 0 | 4 | 4 | 4 |
| (Controls) | 872 | 0 | 4 | 4 | 4 |

[a]Clinical scores were based on the number of feet with vesicular lesions.
[b]Cattle were challenged by intradermolingual inoculation of 4 log 10 bovine infectious doses of FMDV $A_{24}$WT.
[c]Day of challenge Example 11

Pathogenic Characteristics of Double Marker A-Turkey/06-and Asia1/LL3B$_{PVKV}$3D$_{YR}$ Recombinant Viruses in Pigs Experimental direct inoculation in the heel-bulb of susceptible pigs with $10^6$ PFUs of Asia1-$A_{24}$LL3B$_{PVKV}$3D$_{YR}$ virus was performed in three animals (Table 7, animals #199, 200 and #201), and two contact animals (#197 and #198) that were moved into the same pen at 24 hpi and housed together for 20 days. Likewise, pigs #202, 203 and 204 (Table 8) were inoculated in a separate room with $10^6$ PFUs of A-Turkey/06-$A_{24}$LL3B$_{PVKV}$3D$_{YR}$ virus and pigs #205 and 206 were moved into the room as in contact control animals. No clinical signs of FMD were observed in any of the directly inoculated or contact animals during the course of this experiment. Among the Asia1/$A_{24}$LL3B$_{PVKV}$3D$_{YR}$ directly inoculated animals, one of three animals had traces of detectable RNA in serum at 2 dpi and developed antibodies against FMDV at days 7 (Pig 199 neutralizing titer of 1.5). Among the A-Turkey/06-$A_{24}$LL3B$_{PVKV}$3D$_{YR}$ direct inoculated pigs, one pig (#204) had traces of serum and oral swab at 7 dpi but did not developed FMDV-specific antibodies. However, another pig (#202) showed no virus in serum or swabs but had a serum neutralizing titer of 1.8 at 14 dpi, in the absence of any clinical manifestation of FMD. Interestingly, no virus was shed from the three inoculated animals to the two in-contact animals in either group. The pigs were never pirexic (temperatures remained below 40° C.) during the course of this experiment. Furthermore, in postmortem examination of various tissues from two animals in each of the inoculated groups (Table 8), only two pigs inoculated with A-Turkey/06-$A_{24}$LL3B$_{PVKV}$3D$_{YR}$, presented two FMDV-RNA positive tissues, one in each pig, with very low amounts of RNA copy numbers. Shedding of virus was also measured through air sampling and traces of RNA was detected at 3 and 4 dpi in the air filters located in the room that contained the pigs inoculated with Asia1-$A_{24}$LL3B$_{PVKV}$3D$_{YR}$.

TABLE 7

Responses of swine to infection with Asia1/-$A_{24}$LL3B$_{PVKV}$3D$_{YR}$ or ATurkey06/-$A_{24}$LL3B$_{PVKV}$3D$_{YR}$ viruses; virus shedding measurements.

| Swine # | Virus | Inoculation Route | Viremia Max Titer[a] (DPI)[b] | Virus in Saliva - Max Titer[a] (DPI)[b] | Virus in Nasal Swab - Max Titer[a] (DPI)[b] | Fever[c] (DPI) | Clinical Score | Neutralization Titer[d] (DPI)[e] |
|---|---|---|---|---|---|---|---|---|
| 199 | Asia1/$A_{24}$LL3B$_{PVKV}$3D$_{YR}$ | Direct[f] | 4.03 (2)[h] | Negative | Negative | No | Negative | 1.5 (7) |
| 200 | Asia1/$A_{24}$LL3B$_{PVKV}$3D$_{YR}$ | Direct | Negative | Negative | Negative | No | Negative | <0.9 |
| 201 | Asia1/$A_{24}$LL3B$_{PVKV}$3D$_{YR}$ | Direct | Negative | Negative | Negative | No | Negative | <0.9 |
| 197 | Asia1/$A_{24}$LL3B$_{PVKV}$3D$_{YR}$ | Contact[g] | Negative | Negative | Negative | No | Negative | <0.9 |
| 198 | Asia1/$A_{24}$LL3B$_{PVKV}$3D$_{YR}$ | Contact | Negative | Negative | Negative | No | Negative | <0.9 |
| 202 | ATurkey06/$A_{24}$LL3B$_{PVKV}$3D$_{YR}$ | Direct | Negative | Negative | Negative | No | Negative | 1.8 (14) |
| 203 | ATurkey06/$A_{24}$LL3B$_{PVKV}$3D$_{YR}$ | Direct | Negative | Negative | Negative | No | Negative | <0.9 |
| 204 | ATurkey06/$A_{24}$LL3B$_{PVKV}$3D$_{YR}$ | Direct | 3.34 (1) | 3.40 (7) | Negative | No | Negative | <0.9 |

TABLE 7-continued

Responses of swine to infection with Asia1/-$A_{24}LL3B_{PVKV}3D_{YR}$ or ATurkey06/-$A_{24}LL3B_{PVKV}3D_{YR}$ viruses; virus shedding measurements.

| Swine # | Virus | Inoculation Route | Viremia Max Titer[a] (DPI)[b] | Virus in Saliva - Max Titer[a] (DPI)[b] | Virus in Nasal Swab - Max Titer[a] (DPI)[b] | Fever[c] (DPI) | Clinical Score | Neutralization Titer[d] (DPI)[e] |
|---|---|---|---|---|---|---|---|---|
| 205 | ATurkey06/$A_{24}LL3B_{PVKV}3D_{YR}$ | Contact | Negative | Negative | Negative | No | Negative | <0.9 |
| 206 | ATurkey06/$A_{24}LL3B_{PVKV}3D_{YR}$ | Contact | Negative | Negative | Negative | No | Negative | <0.9 |

[a]Expressed in log10 RNA copy number/ml.
[b]Indicates the day after inoculation that peak of virus was detected
[c]Fever defined as rectal temperature ≥ 40.0° C.
[d]FMDV-specific neutralizing antibody titer (log10 of reciprocal of the last serum dilution to neutralize 100 TCID50 of virus in 50% of the wells).
[e]Indicates first day(s) after inoculation that neutralizing antibodies were detected.
[f]Indicates intradermal inoculation in the heel bulb with $10^{\wedge}6$ TCID50
[jg]Direct contact started 24 hours post direct inoculation and lasted until the end of the experiment (21 dpi).
[h]RNA copy number, sensitivity = $10^{\wedge}2.4$/ml

TABLE 8

Real time measurements of viral RNA on postmortem samples from swine inoculated with Asia1-$A_{24}LL3B_{PVKV}3D_{YR}$ or ATurkey06-$A_{24}LL3B_{PVKV}3D_{YR}$.

| | Asia1-$A_{24}LL3B_{PVKV}3D_{YR}$ Animal # | | ATurkey06-$A_{24}LL3B_{PVKV}3D_{YR}$ Animal # | |
|---|---|---|---|---|
| Tissue | 199 | 200 | 203 | 204 |
| Inoculation site | NEG[a] | NEG | NEG | NEG |
| Tongue | NEG | NEG | NEG | NEG |
| Popliteal LN | NEG | NEG | 2.36 | NEG |
| Nasopharynx | NEG | NEG | NEG | 2.34 |
| Lung | NEG | NEG | NEG | NEG |
| Palatine tonsil | NEG | NEG | NEG | NEG |
| Coronary band | NEG | NEG | NEG | NEG |

[a]Indicates FMDV RNA copy number per mg of tissue. Cutoff value is 2.26.

TABLE 9

Vaccination: Clinical scores[a] after challenge with FMDV $A_{24}$WT or Asia1.

| | | Days post vaccination | | | |
|---|---|---|---|---|---|
| | Bovine # | 21[b] | 24 | 28 | 31 |
| $A_{24}LL3B_{PVKV}3D_{YR}$ Vaccine 15 ug/dose | 10-18 | 0 | 0 | 0 | 0 |
| | 10-19 | 0 | 0 | 0 | 0 |
| | 10-20 | 0 | 0 | 0 | 0 |
| | 10-21 | 0 | 0 | 0 | 0 |
| Asia1 $A_{24}LL3B_{PVKV}3D_{YR}$ Vaccine 9 ug/dose | 11-10 | 0 | 3 | 4 | 4 |
| | 11-11 | 0 | 0 | 0 | 0 |
| | 11-12 | 0 | 0 | 0 | 0 |
| | 11-13 | 0 | 0 | 0 | 0 |
| PBS (Controls) | 10-22 | 0 | 4 | 4 | 4 |
| | 10-23 | 0 | 4 | 4 | 4 |
| | 11-14 | 0 | 4 | 4 | 4 |
| | 11-15 | 0 | 4 | 4 | 4 |

[a]Clinical scores were based on the number of feet with vesicular lesions.
[b]Day of challenge. Cattle were challenged by intradermolingual inoculation of 10,000 bovine infections doses of homologous FMDV.

Example 12

BEI-inactivated $A_{24}LL3B_{PVKY}3D_{YR}$ and Asia 1-$LL3B_{PVKY}3D_{YR}$ Viruses Elicit Protective Immune Responses in Cattle To determine the efficacy of the marker BEI-inactivated $A_{24}LL3B_{PVKY}3D_{YR}$ and chimeric Asia 1-$LL3B_{PVKY}3D_{YR}$ vaccines in providing immunological protection against challenge with parental $A_{24}$ and Asia-1 viruses, the BEI-inactivated $A_{24}LL3B_{PVKY}3D_{YR}$ and chimeric Asia 1-$LL3B_{PVKY}3D_{YR}$ vaccines were tested in a cattle vaccine trial. Vaccine antigen was harvested and inactivated as shown in Example 9. Four steers (Cattle #10-18, 10-19, 10-20 and 10-21) received a 15 μg/dose of BEI-inactivated $A_{24}LL3B_{PVKY}3D_{YR}$ vaccine as shown in Table 9. As a control, steers #10-22 and #10-23 received a solution containing PBS/adjuvant. Four steers (Cattle #11-10, 11-11, 11-12 and 11-13) received a 9 μg/dose of BEI-inactivated Asia 1-$LL3B_{PVKY}3D_{YR}$ vaccine; control animals #11-14 and 11-15 were treated as above.

On day 21 post vaccination all animals were challenged by intradermal inoculation at four sites in the tongue with 10,000 bovine infectious doses ($BTID_{50}$) of parental FMDV $A_{24}$Cru or Asia1viruses. The animals were then monitored at 0, 4, 7 and 10 days post-challenge for the appearance of localized and generalized lesions and rectal temperatures were recorded.

All control mock-vaccinated animals developed lesions on their feet (Table 9) and viremia at 1 to 5 dpc (not shown) while only one of the Asia1-$A_{24}LL3B_{PVKY}3D_{YR}$ vaccine-immunized animals (bovine #11-10) developed fever at 48 h dpc and showed vesicles characteristic of FMD in three feet. As shown in Table 9, all vaccinated animals inoculated with the double marker $A_{24}LL3B_{PVKY}3D_{YR}$ vaccine and 3 of 4 animals that received the Asia1-$A_{24}LL3B_{PVKY}3D_{YR}$ inactivated vaccines were fully protected from challenge with the corresponding parental $A_{24}$WT or Asia 1 viruses, as observed by the absence of clinical signs (Table 9) or high temperatures (Table 10).

In the marker virus-vaccinated groups, animals developed detectable FMDV-specific neutralizing antibody responses by 7 or 14 dpv, with slightly higher neutralizing titers at 14 and 21 dpv except for the animal #11-10 that maintained neutralizing titers at 1.5 at 14 and 21 dpv (Table 11). All the control naïve animals (bovines #10-22, 10-23, 11-14 and 11-15) that received PBS/adjuvant had no detectable FMDV-specific antibody response at day of challenge (Table 11). Virus was detected from nasal secretions in all the animals post-challenge (data not shown).

TABLE 10

Vaccination Trial: Rectal temperatures (in ° C.) after challenge with parental FMDV $A_{24}$WT and Asia 1 Viruses.

| | Bovine # | 21[a] | 22 | 23 | 24 | 25 | 26 | 27 | 28 | 29 | 30 | 31 |
|---|---|---|---|---|---|---|---|---|---|---|---|---|
| $A_{24}LL3B_{PVKV}3D_{YR}$ | 10-18 | 38.8[b] | 38.8 | 38.7 | 39.0 | 39.0 | 39.2 | 38.9 | 39.0 | 39.4 | 38.7 | 39.2 |
| Vaccine | 10-19 | 38.3 | 38.8 | 38.8 | 39.0 | 38.6 | 39.4 | 38.7 | 38.4 | 39.0 | 38.9 | 38.7 |
| | 10-20 | 38.4 | 38.8 | 38.2 | 38.7 | 39.0 | 39.7 | 39.1 | 38.7 | ND[c] | ND | ND |
| | 10-21 | 38.6 | 38.4 | 38.8 | 38.9 | 38.4 | 38.8 | 38.8 | 38.7 | 38.8 | 38.4 | 38.9 |
| Asia1 $A_{24}LL3B_{PVKV}3D_{YR}$ | 11-10 | 38.4 | 39.7 | 41.0 | 40.7 | 40.0 | 39.5 | 38.4 | 38.2 | 38.8 | 38.2 | 38.6 |
| Vaccine | 11-11 | 38.7 | 38.8 | 40.3 | 39.1 | 38.6 | 38.6 | 38.9 | 38.8 | 39.2 | 38.8 | 38.8 |
| | 11-12 | 38.3 | 38.8 | 39.0 | 38.7 | 38.3 | 38.6 | 38.6 | 38.8 | 38.9 | 38.7 | 38.4 |
| | 11-13 | 38.1 | 38.7 | 39.3 | 39.3 | 38.7 | 38.8 | 38.7 | 38.6 | 38.8 | 38.6 | 38.6 |
| PBS (Controls) | 10-22 | 38.6 | 39.4 | 39.8 | 40.1 | 39.0 | 38.8 | 38.9 | 38.7 | 39.4 | 40.0 | 38.9 |
| | 10-23 | 38.7 | 39.2 | 40.6 | 39.8 | 39.8 | 38.9 | 39.0 | 39.0 | 39.1 | 38.8 | 38.4 |
| | 11-14 | 38.4 | 38.8 | 40.5 | 40.3 | 40.1 | 39.2 | 38.7 | 39.2 | 39.3 | 39.0 | 39.0 |
| | 11-15 | 38.1 | 41.4 | 41.4 | 40.7 | 39.2 | 39.7 | 38.9 | 38.6 | 39.3 | 38.6 | 38.5 |

[a]Day of challenge
[b]Considered fever when ≥40.0° C.
[c]Not determined

TABLE 11

Vaccination Trial: Specific neutralizing antibody response against FMDV after vaccination with $A_{24}LL3B_{PVKV}3D_{YR}$ or Asia1-$A_{24}LL3B_{PVKV}3D_{YR}$ vaccines and challenged with FMDV $A_{24}$WT or Asia1.

| | Bovine # | 0[a] | 7 | 14 | 21[b] | 28 | 35 | 42 |
|---|---|---|---|---|---|---|---|---|
| $A_{24}LL3B_{PVKV}3D_{YR}$ | 10-18 | <0.9[c] | 1.8 | 2.1 | 2.1 | 3.0 | 3.3 | 3.0 |
| Vaccine | 10-19 | <0.9 | 2.1 | 2.1 | 2.1 | 3.3 | 3.6 | 3.0 |
| 15 ug/dose | 10-20 | <0.9 | <0.9 | 2.1 | 1.8 | 2.7 | ND[d] | ND |
| | 10-21 | <0.9 | 1.5 | 1.8 | 2.1 | 2.1 | 2.7 | 3.6 |
| Asia1 $A_{24}LL3B_{PVKV}3D_{YR}$ | 11-10 | <0.9 | 1.2 | 1.5 | 1.5 | ND | ND | ND |
| Vaccine | 11-11 | <0.9 | 1.8 | 2.1 | 2.1 | ND | ND | ND |
| 9 ug/dose | 11-12 | <0.9 | 1.8 | 2.4 | 2.4 | ND | ND | ND |
| | 11-13 | <0.9 | 2.1 | 2.4 | 1.5 | ND | ND | ND |
| PBS (Controls) | 10-22 | <0.9 | <0.9 | <0.9 | <0.9 | 2.4 | 3.3 | 2.7 |
| | 10-23 | <0.9 | <0.9 | <0.9 | <0.9 | 2.7 | 2.7 | 2.1 |
| | 11-14 | <0.9 | <0.9 | <0.9 | <0.9 | ND | ND | ND |
| | 11-15 | <0.9 | <0.9 | <0.9 | <0.9 | ND | ND | ND |

[a]Day of vaccination.
[b]Day of challenge
[c]Virus neutralizing titers of serum antibodies responses.
[d]Not determined Example 13

Foot and Mouth Disease Virus RNA Detection and DNA Sequence Analysis

Fifty μl of each sample (sera or nasal swab resuspension) for each cow were transferred to 96-well plates (King Fisher number 97002540) containing 150 μl lysis/binding solution. RNA was then extracted using Ambion's MagMax-96 Viral RNA Isolation Kit (Ambion, catalogue number 1836) on a King Fisher-96 Magnetic Particle Processor (Thermo Electron Corp.). Briefly, after the initial 5 min lysis/binding step, the RNA sample underwent a series of four washing steps, a drying step, and a final elution step. RNA was eluted in a final volume of 25 μl. At each of the above steps, RNA was magnetically bound to the beads contained in the lysis/binding solution and was transferred to the different extraction solutions. For filters containing the air samples, ¼ filters were processed with 600 μL RLT/β-mercaptoethanol and 106-micron acid washed glass beads. The sample was then disrupted using a Retsch tissue lyser (model MM400) at 30 beats/sec for 3 minutes and the liquid suspension used for RNA extraction with the standard RNeasy RNA extraction. RNA extracted from all the previous described samples was analyzed by rRT-PCR using 2.5 μl of RNA on the ABI 7000 as previously described (Callahan et al. 2002. J. Am. Vet. Med. Assoc. 220: 1636-1642). The cutoff to consider a positive value for preclinical samples (sera and swabs) was $10^{2.4}$ RNA copy number/ml and for air samples, $10^{0.8}$ RNA copy number/1000 liters of air. When necessary, PCR amplicons were sequenced using gene-specific primers, Big Dye Termination Cycle Sequencing Kits (Applied Biosystems, Foster City, Calif.) and a PRISM 3700 automated sequencer (Applied Biosystems). Primers and probes were designed using Primer Express® software (Applied Biosystems, Foster City, Calif.).

Example 14

Monoclonal Antibodies, Expression of Recombinant FMDV-3D Protein

Sera taken at different times post infection were examined for the presence of antibodies that could compete. Expression vectors for 3D$^{pol}$ were prepared by using standard recombinant DNA methods. Briefly, PCR was used to amplify the 3D$^{pol}$-coding sequence of a type A FMDV. Forward primer P727 (5'-GCGGAATTCCCGCGGTGGA GGGT-TAATCGTTGATAC; SEQ ID NO:17) designed to fuse the carboxi-terminal three amino acids of ubiquitin (Wei et al. 2001. *J. Virol.* 75:1211-1219.) to the coding sequence for 3D$^{pol}$ were designed to include SacII restriction site for cloning purposes. The antisense primer encoded the carboxi-terminal residues also contains a BamHI restriction site P728 (5'-GCGGAATTCGGATCCTGCGTCACCGCA-CACGGCGTTCA CCC; SEQ ID NO:18). The PCR product was cloned into pET26cHis.

Example 15

Serology and Antigen Differentiation Assays

Serum samples from all animals from all trials were tested for the presence of neutralizing antibodies against FMDV in a serum neutralization assay. Neutralizing titers were reported as the reciprocal of the last serum dilution to neutralize 100 TCID$_{50}$ of homologous FMDV in 50% of the wells (Golde et al. 2005. *Vaccine* 23:5775-5782). Sera were also tested for the presence of antibodies against viral proteins by a RIP assay as previously described (Piccone et al., supra).

To study the anti-3D$^{pol}$ response in the animals, we utilized sera collected from cattle inoculated by aerosol with either A$_{24}$WT3D$_{YR}$ (bovines #s 7199, 1, 2), A$_{24}$WT (bovines #7109, 7110), or two A$_{24}$WT introdermolingual inoculated (#871, 872). Competitive Enzyme-Linked Immunosorbent Assay (cELISA) was performed following the protocol by Yang et al. (2007a, supra) with minor modifications. Briefly, recombinant 3D$^{pol}$ was diluted in buffer carbonate-bicarbonate (pH 9.6) to obtain 0.33 ug/ml and 100 μl/well were used to coat Nunc Maxisorp plates (Fisher Scientific). Following 2 hours incubation at 37° C. on a rotary shaker, plates were washed four times with 0.01 PBS, 0.05% Tween20 (PBS-T), and triplicates of 50 μl/well of test sera (1/5 in PBS-T) and 50 μl/well of F32-44 hybridoma culture supernatant (1/5 in PBS-T) were applied to the coated plates and incubated overnight at 4° C. After washing four times, 100 μl/well of peroxidase-labeled goat antibody to mouse-IgG (H+L) (KPL) diluted 1/2000 in 5% skim milk in PBS-T were added and incubated for 1 h at 37° C. After four washes the antigen-antibodies complexes were detected by the addition of 100 μl/well of SureBlue Reserve™ (KPL) and stopped in 10 min with 50 μl/well of TMB BlueSTOP™ solution (KPL). The OD was determined at 630 mm on an automated ELISA plate reader. For cELISA based on MAb F8B a similar protocol was utilized with minor modification. In particular, the antigen applied to the plate consisted of a peptide encoding the 3B sequence GPYAGPLETQKPLK applied at a concentration of 0.05 μg/well. Test sera were assayed at a 1/5 dilution in PBS-T and MAb F8B was used at a 1/125 dilution.

Distinctive antibody responses were identified for mutant A$_{24}$WT3D$_{YR}$ and A$_{24}$LL3D$_{YR}$ against 3D$^{pol}$ using a cELISA assay. Sera collected from animals inoculated with the marker A$_{24}$WT3D$_{YR}$ virus by the aerosol route (days 0 and 21) or inoculated with A$_{24}$WT by the intradermolingual (days 0 and 21) or the aerosol routes (days 0 and 9) were analyzed against FMDV 3D$^{pol}$ protein in a cELISA. A representative assay presented in FIG. 4 allows distinction of the serological responses in cattle to inoculation with either parental virus (A$_{24}$WT) and mutant (A$_{24}$WT3D$_{YR}$) virus. While seroconversion after inoculation with A$_{24}$WT resulted in significant inhibition of the anti-3D$^{pol}$ response in our cELISA format, sera from animals inoculated with A$_{24}$WT3D$_{YR}$ showed restricted inhibition. This assay that utilizes monoclonal F32-44 allowed differentiation of animals infected with A$_{24}$WT from the negative marker virus A$_{24}$WT3D$_{YR}$.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated DNA molecule comprising a sequence encoding a genetically marked Foot and Mouth Disease Virus (FMDV) comprising a deletion of the $L^{pro}$ coding sequence, inclusion of unique restriction endonuclease sites to facilitate the replacement of the FMDV capsid region, and a negative marker mutation introduced in the non-structural viral protein $3D^{pol}$, said mutation being the replacement of amino acids $His_{27}$ and $Asn_{31}$ of FMDV $3D^{pol}$ with the amino acids Tyr and Arg of the $3D^{pol}$ of Bovine Rhinovirus type 2 (BRV2).

2. The isolated DNA molecule of claim 1, where the DNA sequence encodes a genetically modified strain of FMDV $A_{24}$ Cruzeiro.

3. The isolated DNA molecule of claim 2 wherein said DNA sequence comprises SEQ ID NO:1.

4. An isolated DNA molecule comprising a sequence encoding a double marker Foot and Mouth Disease Virus (FMDV) comprising a deletion of the $L^{pro}$ coding sequence, inclusion of unique restriction endonuclease sites to facilitate the replacement of the FMDV capsid region, a negative marker mutation introduced in the non-structural viral protein $3D^{pol}$, said mutation being the replacement of amino acids $His_{27}$ and $Asn_{31}$ of FMDV $3D^{pol}$ with the amino acids Tyr and Arg of the $3D^{pol}$ of Bovine Rhinovirus type 2 (BRV2), and a second negative marker mutation introduced in the non-structural viral protein 3B, said mutation being the replacement of amino acids RQKP of FMDV 3B with the amino acids PVKV of the 3B of BRV2.

5. The isolated DNA molecule of claim 4, where the DNA sequence encodes a genetically modified strain of FMDV $A_{24}$ Cruzeiro.

6. The isolated DNA molecule of claim 5, wherein said DNA sequence comprises SEQ ID NO:3.

7. An isolated DNA molecule according to claim 1 or 4 encoding a chimeric FMDV, wherein the FMDV capsid region between the unique restriction sites has been replaced with an FMDV capsid region from a different strain.

8. The isolated DNA molecule of claim 7, where the DNA sequence encodes a genetically modified strain of FMDV $A_{24}$ Cruzeiro with an FMDV capsid region from a different strain.

9. The isolated DNA molecule of claim 8, wherein the different strain is FMDV Asia 1.

10. The isolated DNA molecule of claim 9, wherein said DNA sequence comprises SEQ ID NO:26.

11. The isolated DNA molecule of claim 7, wherein the different strain is FMDV Type A-Turkey/06.

12. The isolated DNA molecule of claim 11, wherein said DNA sequence comprises SEQ ID NO:27.

13. The genetically marked Foot and Mouth Disease Virus (FMDV) encoded by the DNA of claim 1.

14. The doubly marked Foot and Mouth Disease Virus (FMDV) encoded by the DNA of claim 4.

15. The chimeric Foot and Mouth Disease Virus (FMDV) encoded by the DNA of claim 7.

16. The virus of claim 13, which is chemically inactivated.

17. The virus of claim 14, which is chemically inactivated.

18. The virus of claim 15, which is chemically inactivated.

19. A vaccine comprising the genetically marked virus of claim 13.

20. A vaccine comprising the doubly marked virus of claim 14.

21. A vaccine comprising the chimeric virus of claim 15.

22. A method of protecting an animal against FMDV, comprising administering to said animal an effective amount of the genetically marked vaccine of claim 19.

23. A method of protecting an animal against FMDV, comprising administering to said animal an effective amount of the doubly marked vaccine of claim 20.

24. A method of protecting an animal against FMDV, comprising administering to said animal an effective amount of the chimeric vaccine of claim 21.

25. A method of producing a genetically marked inactivated FMDV vaccine, comprising expressing infectious RNA from the DNA of claim 1, recovering virus from the infectious RNA, and inactivating an effective immunizing amount of the virus.

26. A method of producing a doubly marked inactivated FMDV vaccine, comprising expressing infectious RNA from the DNA of claim 4, recovering virus from the infectious RNA, and inactivating an effective immunizing amount of the virus.

27. A method of producing a chimeric inactivated FMDV vaccine, comprising expressing infectious RNA from the DNA of claim 7, recovering virus from the infectious RNA, and inactivating an effective immunizing amount of the virus.

* * * * *